(12) United States Patent
Bormann Chung et al.

(10) Patent No.: US 12,378,601 B2
(45) Date of Patent: Aug. 5, 2025

(54) MULTIPLEX Y-STR ANALYSIS

(71) Applicant: LIFE TECHNOLOGIES CORPORATION, Carlsbad, CA (US)

(72) Inventors: Christina Bormann Chung, Half Moon Bay, CA (US); Julio Mulero, Carlsbad, CA (US); Lori Hennessy, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 16/799,810

(22) Filed: Feb. 24, 2020

(65) Prior Publication Data

US 2020/0255892 A1    Aug. 13, 2020

Related U.S. Application Data

(62) Division of application No. 14/727,442, filed on Jun. 1, 2015, now Pat. No. 10,597,707, which is a division of application No. 13/828,443, filed on Mar. 14, 2013, now abandoned.

(60) Provisional application No. 61/761,152, filed on Feb. 5, 2013, provisional application No. 61/720,949, filed on Oct. 31, 2012, provisional application No. (Continued)

(51) Int. Cl.
| | |
|---|---|
| C12Q 1/68 | (2018.01) |
| C12Q 1/6858 | (2018.01) |
| C12Q 1/6879 | (2018.01) |
| C12Q 1/6888 | (2018.01) |
| C12Q 1/686 | (2018.01) |

(52) U.S. Cl.
CPC ......... *C12Q 1/6858* (2013.01); *C12Q 1/6879* (2013.01); *C12Q 1/6888* (2013.01); C12Q 1/686 (2013.01); C12Q 2600/156 (2013.01); C12Q 2600/16 (2013.01)

(58) Field of Classification Search
CPC .. C12Q 1/6858; C12Q 1/6879; C12Q 1/6888; C12Q 1/686; C12Q 2600/156; C12Q 2600/16
See application file for complete search history.

(56) References Cited

U.S. PATENT DOCUMENTS

| 10,597,707 B2 | 3/2020 | Bormann Chung et al. |
| 2003/0224372 A1 | 12/2003 | Syndercombe-Court |
(Continued)

FOREIGN PATENT DOCUMENTS

| CN | 101225386 A | 7/2008 |
| EP | 2055787 A1 | 5/2009 |
(Continued)

OTHER PUBLICATIONS

Goedbloed et al. (Int J Legal Med, 2009, (123):471-482) (Year: 2009).*

(Continued)

*Primary Examiner* — Stephanie K Mummert
(74) *Attorney, Agent, or Firm* — Caroline D. Belt

(57) ABSTRACT

Novel Y-STR multiplex analysis designs, primer design, allelic ladders, methods of use and kits are disclosed, including the use of primer sets designed to provide amplicons for at least 11 Y-STR loci having a base pair size of less than about 220 bp, as well as the use of primer sets designed to provide amplicons for at least 22 Y-STR loci including at least 5 rapidly mutating loci.

10 Claims, 30 Drawing Sheets
Specification includes a Sequence Listing.

Related U.S. Application Data

61/697,742, filed on Sep. 6, 2012, provisional application No. 61/765,323, filed on Feb. 15, 2013.

(56) References Cited

U.S. PATENT DOCUMENTS

| | | | |
|---|---|---|---|
| 2006/0088874 | A1 | 4/2006 | Bacher et al. |
| 2009/0117542 | A1 | 5/2009 | Maybruck et al. |
| 2011/0263437 | A1* | 10/2011 | Fang ............ C12Q 1/6888 506/7 |
| 2013/0109579 | A1 | 5/2013 | Fang et al. |
| 2013/0137589 | A2* | 5/2013 | Fang ............ C12Q 1/6888 506/7 |

FOREIGN PATENT DOCUMENTS

| | | |
|---|---|---|
| KR | 20010105503 A | 11/2001 |
| WO | WO-2009059049 A1 | 5/2009 |
| WO | WO-2011032054 A2 | 3/2011 |
| WO | WO-2012067901 A1 | 5/2012 |

OTHER PUBLICATIONS

Mulero et al. (J Forensic Sci, 2006, 51(1):64-75) (Year: 2006).*

Hammer et al. (Forensic Applications of Y Chromosome STRs and SNPs, 2000-IJ-CX-K006 Cumulative Technical Report, Jan. 2006, p. 1-51) (Year: 2006).*

Jacobs et al. (Forensic Science International:Genetics Supplement Series 2, 2009, 57-59) (Year: 2009).*

Butler (Biotechniques, 2007, 43:4, p. ii-v) (Year: 2007).*

Jacobs et al. (Forensic Sci Int:Genetic Suppl Series 2, 2009, 57-59) (Year: 2009).*

Janssen et al. (Forensic Sci Int:Genetic Suppl Series 2, 2009, 124-125) (Year: 2009).*

Elroby, A.M., 2018. Genetics and Molecular studies on linkage patterns of Y chromosome and paternity tests in samples applied in forensic investigations (Doctoral dissertation, Menoufia University) (Year: 2018).*

Aler et al., Population study of eight novel Y-chromosome STRs (DYS460, DYS461, GATAA10, GATA-C4, GATA-H4, DYS434, DYS437, DYS439) in a southeast Iberian population: looking for highly informative Y-chromosome haplotypes. International Journal of Legal Medicine, 2003, vol. 117, No. 2, 2003, pp. 127-131.

Alves et al. Evaluating the informative power of Y-STRs: a comparative study using European and new African haplotype data. Forensic Science International, vol. 134, Nos. 2-3: pp. 126-133.

Arroyo-Pardo et al. Genetic variability of 16 Y-chromosome STRs in a sample from Equatorial Guinea (Central Africa). Forensic Science International, vol. 149, No. 1, 2005, pp. 109-113.

Asamura et al., "Evaluation of MiniY-STR Multiplex PCR Systems for Extended 16 Y-STR Loci", International Journal of Legal Medicine, vol. 122, 2008, pp. 43-49.

Asamura et al., "MiniY-STR Quadruplex Systems with Short Amplicon Lengths for Analysis of Degraded DNA Samples" Forensic Science International, Genetics, vol. 1, 2007, pp. 56-61.

Ballantyne et al. Additional Y-STRs in Forensics: Why, Which, and When. Forensic Science Review, vol. 24, No. 1, 2012, pp. 64-78.

Ballantyne et al., "A new future of forensic Y-chromosome analysis: Rapidly mutating YSTRs for differentiating male relatives and paternal lineages", Forensic Science International: Genetics, vol. 6, No. 2, Mar. 2012, pp. 208-218.

Ballantyne et al., "Mutability of Y-chromosomal microsatellites: rates, characteristics, molecular bases and forensic implications" American Journal of Human Genetics, 2010, pp. 341-353.

Bosch E. et al. High resolution Y chromosome typing: 19 STRs amplified in three multiplex reactions. Forensic Science International, 2002, 125(1):42-51.

Butler et al., "A novel multiplex for simultaneous amplification of 20 Y chromosome STR markers," Forensic Science International, vol. 129, 2002, pp. 10-24.

Butler, J. et al., "Allele Frequencies for 27 Y-STR Loci with U.S. Caucasian, African American, and Hispanic Samples", Forensic Science International, vol. 156, 2006, pp. 250-260.

Butler, J. et al., "Genetics and genomics of core short tandem repeat loci used in human identity testing", Journal of Forensic Sciences, vol. 51, No. 2, 2006, pp. 253-265.

Butler, J.M., "Constructing STR Multiplex Assays", Forensic DNA Typing Protocols, vol. 297, pp. 53-65 (2005).

Coble, M. D. et al., "Characterization of new MiniSTR loci to aid analysis of degraded DNA", Journal of Forensic Sciences, vol. 50(1), Jan. 2005, 43-53 (pp. 1-11 as presented).

D'Amato, M. et al., "Characterization of the highly discriminatory loci DYS449, DYS481, DYS518, DYS612, DYS626, DYS644 and DYS710", Forensic Science International: Genetics, vol. 4, No. 2, 2010, pp. 104-110.

D'Amato, M. et al., "Evaluation of 21 Y-STRs for Population and Forensic Studies", Forensic Science International: Genetics Supplement Series 2, 2009, pp. 446-447.

Decker, A. et al., "Evaluation of Additional Y-STR Loci to Resolve Common Haplotypes", National Institute of Standards and Technology, 2006, p. 1.

Decker, A. et al., "The impact of additional Y-STR loci on resolving common haplotypes and closely related individuals", National Institute of Standards and Technology, Bio Sci Div., Forensic Science International : Genetics 1, 2007, pp. 215-217.

Ehler E. et al. (201 0) Evaluation of 14 Y-chromosomal short tandem repeat haplotype with focus on DYS449, DYS456, and DYS458: Czech population sample. (Translated from eng) Croat Med J, 2010, 51 (1):54-60 (in eng).

Geppert, M. et al., "The Y-chromosomal STRs DYS481, DYS570, DYS576 and DYS643", Institute of legal Medicine, Legal Medicine, vol. 11, 2009, pp. s109-s110.

Giese et al., "Fast Multiplexed Polymerase Chain Reaction for Conventional and Microfluidic Short Tandem Repeat Analysis", Journal of Forensic Sciences, vol. 54, No. 6, Nov. 2009, pp. 1287-1296.

Goedbloed, et al., "Comprehensive mutation analysis of 17 Y-chromosomal short tandem repeat polymorph isms included in the AmpFISTR® Yfiler® PCR amplification kit", International Journal of Legal Medicine, vol. 123, Issue 6, 2009, pp. 471-482.

Goff, P G. et al., "Diagnostic Y-STR Markers In Haplogroup G" Journal of Genetic Genealogy, vol. 2, No. 1, 2006, See Abstract, pp. 12-17.

Hanson, E. et al., "A Highly Discriminating 21 Locus Y-STR "Megaplex" System Designed to Augment the Minimal Haplotype Loci for Forensic Casework", Journal of Forensic Sciences, vol. 49, No. 1, ASTM International, 2004, pp. 1-12.

Hanson, E. et al., "An Ultra-High Discrimination Y Chromosome Short Tandem Repeat Multiplex DNA Typing System", PLoS One, vol. 2, Issue 8, e688, 2007, pp. 1-14.

Hanson, E. et al., "Testing and Evaluation of 43 "Noncore" Y Chromosome Markers for Forensic Casework Applications", Journal of Forensic Sciences, vol. 51, No. 6, 2006, pp. 1298-1314.

Hedman, M. et al., Dissecting the Finnish male uniformity: The value of additional Y-STR loci, Forensic Science International: Genetics, vol. 5, 2011, pp. 199-201.

Jacobs, M. et al., "Development and Evaluation of Multiplex Y-STR Assays for Application in Molecular Genealogy", Forensic Science International: Genetics Supplement Series 2, Elsevier Ireland Ltd., 2009, 57-59.

Kayser, M. et al., "A Comprehensive Survey of Human Y-Chromosomal Microsatellites", The American Journal of Human Genetics, vol. 74, 2004, pp. 1183-1197.

Kayser, M. et al., Appendix to Kayser M et al. "A Comprehensive Survey of Human YChromosomal Microsatellites", downloaded at URL: http://download.cell.com/AJHG/mmcs/journals/0002-9297/PIIS0002929707628444.mmc1.txt. Downloaded Jul. 9, 2012.

Kayser, M. et al., "Relating two deep-rooted pedigrees from Central Germany by high-resolution Y-STR haplotyping", Forensic Science International: Genetics, vol. 1, Issue 2, 2007, pp. 125-128.

(56) References Cited

OTHER PUBLICATIONS

Krenke, B. et al., "Validation of male-specific, 12-locus fluorescent short tandem repeat (STR) multiplex [Forensic Sci. Int. 148 (1) (2005) 1-14]", Forensic Science International, vol. 151, No. 1, 2005, pp. 111-124.

Leat, N. et al., Developments in the use of Y-chromosome markers in forensic genetics, African Journal of Biotechnology, vol. 3, No. 12, See p. 639, 2004, pp. 637-642.

Leat N. et al. Properties of novel and widely studied Y-STR loci in three South African populations. Forensic Science International, 2007, 168(2-3):154-161.

Lim, S. et al., "Variation of 52 New Y-STR Loci in the Y Chromosome Consortium Worldwide Panel of 76 Diverse Individuals", International Journal of Legal Medicine, vol. 121, 2007, pp. 124-127.

Martin, P., et al. A Spanish population study of 17 Y-chromosome STR loci. Forensic Science International, 2004, 139(2-3):231-235.

Maybruck, J. et al., "A Comparative Analysis of Two Different Sets of Y-Chromosome Short Tandem Repeats (Y-STRs) on a Common Population Panel", Forensic Science International: Genetics, vol. 4, 2009, pp. 11-20.

Moreau, "Genetic heterogeneity in regional populations of Quebec-Parental lineages in the Gaspe Peninsula", American Journal of Physical Anthropology, vol. 139, Issue 4, 2009, pp. 512-522.

Mulero, J. et al., "Development and Validation of the AmpFlSTR Yfiler PCR Amplification Kit: A Male Specific, Single Amplificatin 17 Y-STR Multiplex System" J Forensic Sci, vol. 51 (1), 2006, pp. 64-75.

Palha T. et al. Fourteen short tandem repeat loci Y chromosome haplotypes: Genetic analysis in populations from northern Brazil. Forensic Science International: 2011, Genetics, vol. 6, pp. 413-418.

Park, M. et al., "Forensic Evaluation and Haplotypes of 19 Y-Chromosomal STR Loci in Koreans", Forensic Science International, vol. 152, 2005, pp. 133-147.

Promega, "PowerPiex® Y23 System", Technical Manual, Instructions for Use of Product DC2305 and 02320, Jul. 2012, 1-75.

Qi Y. et al. Analysis of genetic polymorphism of four Y-STR loci of Han people in Henan province [Chinese], Journal of Xinxiang Medical College, Apr. 2007 [English Translation of Abstract Only].

Rebala, K., et al. Forensic analysis of polymorphism and regional stratification of Y-chromosomal microsatellites in Belarus. Forensic Science International, 2011, Genetics 5(1):e17-e20.

Rebala K. et al., Polish population study on Y chromosome haplotypes defined by 18 STR loci. International Journal of Legal Medicine, 2005, 119(5):303-305.

Redd, A. et al., "Forensic Value of 14 Novel STRs on the Human Y Chromosome", Forensic Science International, vol. 130, 2002, pp. 97-111.

Rodig, H. et al., "Evaluation of Haplotype Discrimination Capacity of 35 Y-Chromosomal Short Tandem Repeat Loci", Forensic Science International, vol. 174, 2008, pp. 182-188.

Schoske R, et al., High-throughput Y-STR typing of U.S. populations with 27 regions of the Y chromosome using two multiplex PCR assays. Forensic Science International, 2004, 139(2-3):1 07-121.

Shen C. et al., Seven new Y-STRs haplotypes of Chinese Han ethnic group. Forensic Science International, 2005, 154(1):81-84.

Shi M., et al. An Analysis on Genetic Polymorphism and Genetic Relationship of 22 Y-STR loci in the Han People in Guangdong, Hereditas, vol. 30, No. 9, 2008, pp. 1136-1142.

Shi M., et al. Haplotypes of 20 Y-chromosomal STRs in a population sample from southeast China (Chaoshan area). International Journal of Legal Medicine, 2007, 121(6):455-462.

Shin D., et al. Y-Chromosome multiplexes and their potential for the DNA profiling of Koreans. International Journal of Legal Medicine, 2001, 115(2): 109-117.

Stratagene, "Stragagene Cloning Systems: Tools and Technology for Life Sciences", Catalog (1988), Published by Stratgene, 11011 North Torrey Pines Road, La Jolla, CA 92037, USA; p. 39.

Tang J., et al. Characterization of eight Y-STR loci and haplotypes in a Chinese Han population. International Journal of Legal Medicine, 2003, 117(5):263-270.

Vermeulen, et al., "Improving global and regional resolution of male lineage differentiation by simple single-copy Y-chromosomal short tandem repeat polymorph isms", Forensic Science International: Genetics, vol. 3, Issue 4, 2009, pp. 205-213.

Von Wurmb-Schwark, et al., "Possible pitfalls in motherless paternity analysis with related putative fathers", Forensic Science International, vol. 159, No. 2-3, 2006, pp. 92-97.

Wu F., et al. Multiplex DNA typing of short tandem repeat loci on Y chromosome of Chinese population in Taiwan. Forensic Science International, 2001, 120(3):213-222.

Xu Z., et al. Diversity of five novel Y-STR loci and their application in studies of north Chinese populations. Journal of Genetics, 2010, 89(1):29-36.

Zarrabeitia, M., et al. Spanish population data and forensic usefulness of a novel Y-STR set (DYS437, DYS438, DYS439, DYS460, DYS461, GATA A1 0, GATA C4, GATA H4). International Journal of Legal Medicine, 2003, 117(5):306-311.

Zhang, Y. et al., Population genetics for Y-chromosomal STRs haplotypes of Chinese Korean ethnic group in northeastern China. Forensic Science International, 2007, 173(2-3):197-203.

Office Action cited in U.S. Appl. No. 16/840,168 dated Jun. 14, 2021.

\* cited by examiner

FIG.9

| Marker | YHRD.ORG | usystrdatabase.org | Yfiler (including virtual alleles) | Panel 6 (excluding 1 virtual allele on each side) | PPY23 |
|---|---|---|---|---|---|
| DYF387S1ab | NA | NA | NA | 27-41 | NA |
| DYS19 | 9-19 | 6, 11-18 | 10-19 | 9-19 | 9-19 |
| DYS385ab | 6-28 | 7-24 | 7-25 | 6-28 | 7-28 |
| DYS389I | 9-17 | 9-16 | 9-16 | 9-17 | 9-17 |
| DYS389II | 24-36 | 25-34 | 24-34 | 24-35 | 24-35 |
| DYS390 | 17-29 | 18-27 | 17-28 | 17-29 | 17-29 |
| DYS391 | 5-16 | 6-13 | 6-14 | 5-16 | 5-16 |
| DYS392 | 4, 6-20 | 7-19 | 6-18 | 4-20 | 4-20 |
| DYS393 | 7-18 | 9-17 | 8-17 | 7-18 | 7-18 |
| DYS460 | NA | NA | NA | 7-14 | NA |
| DYS437 | 10-18.2 | 13-18.2 | 13-18 | 10-18 | 11-18 |
| DYS438 | 7-16, 18 | 7-15 | 8-13 | 6-16 | 6-16 |
| DYS439 | 5-17, 19 | 8-15 | 8-15 | 6-17 | 6-17 |
| DYS448 | 14-24 | 15-24 | 16-24 | 14-24 | 14-24 |
| DYS449 | NA | NA | NA | 22-40 | NA |
| DYS456 | 5, 10-23 | 11-21 | 13-18 | 11-23 | 11-23 |
| DYS458 | 11-24 | 11-22 | 14-20 | 11-24 | 10-24 |
| DYS481 | NA | NA | NA | 17-32 | 17-32 |
| DYS533 | NA | NA | NA | 7-17 | 7-17 |
| DYS570 | NA | NA | NA | 10-26 | 10-25 |
| DYS576 | NA | NA | NA | 10-25 | 10-23 |
| DYS627 | NA | NA | NA | 9-25 | NA |
| DYS635 | 16-30 | 12, 17-26 | 19-26 | 15-30 | 15-28 |
| DYS643 | NA | NA | NA | 6-17 | 6-17 |
| Y-GATA-H4 | 8-15.1 | 8-15 | 8-13 | 8-15 | 8-18 |

FIG. 12

Allele Ranges for Panel 7:
Compared to databases, AmpFℓSTR® Yfiler and PP Y23

| Marker | YHRD.org | usystrdatabase.org | Yfiler (including virtual alleles) | Panel 7 (excluding 1 virtual allele on each side) | Kit 8 |
|---|---|---|---|---|---|
| DYF387S1ab | NA | NA | NA | 33-44 | NA |
| DYS19 | 9-19 | 6, 11-18 | 10-19 | 9-19 | 9-19 |
| DYS385ab | 6-28 | 7-24 | 7-25 | 6-28 | 7-28 |
| DYS389I | 9-17 | 9-16 | 9-16 | 9-17 | 9-17 |
| DYS389II | 24-36 | 25-34 | 24-34 | 24-35 | 24-35 |
| DYS390 | 17-29 | 18-27 | 17-28 | 17-29 | 17-29 |
| DYS391 | 5-16 | 6-13 | 6-14 | 5-16 | 5-16 |
| DYS392 | 4, 6-20 | 7-19 | 6-18 | 4-20 | 4-20 |
| DYS393 | 7-18 | 9-17 | 8-17 | 7-18 | 7-18 |
| DYS460 | NA | NA | NA | 7-14 | NA |
| DYS437 | 10-18.2 | 13-18.2 | 13-18 | 10-18 | 11-18 |
| DYS438 | 7-16, 18 | 7-15 | 8-13 | 6-16 | 6-16 |
| DYS439 | 5-17, 19 | 8-15 | 8-15 | 6-17 | 6-17 |
| DYS448 | 14-24 | 15-24 | 16-24 | 14-24 | 14-24 |
| DYS449 | NA | NA | NA | 23-41 | NA |
| DYS456 | 5, 10-23 | 11-21 | 13-18 | 10-24 | 11-23 |
| DYS458 | 11-24 | 11-22 | 14-20 | 11-24 | 10-24 |
| DYS481 | NA | NA | NA | 17-32 | 17-32 |
| DYS518 | NA | NA | NA | 32-49 | NA |
| DYS533 | NA | NA | NA | 7-17 | 7-17 |
| DYS570 | NA | NA | NA | 10-26 | 10-25 |
| DYS576 | NA | NA | NA | 10-25 | 11-23 |
| DYS627 | NA | NA | NA | 11-27 | NA |
| DYS635 | 16-30 | 12, 17-26 | 19-26 | 15-30 | 15-28 |
| Y-GATA-H4 | 8-15.1 | 8-15 | 8-13 | 8-15 | 8-18 |

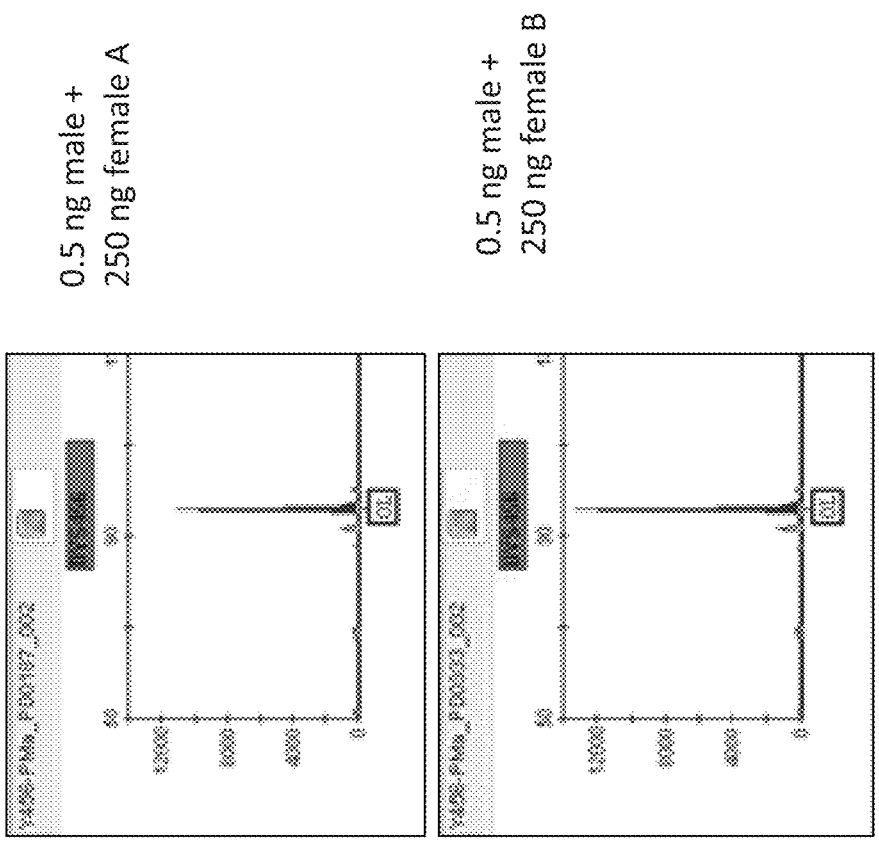
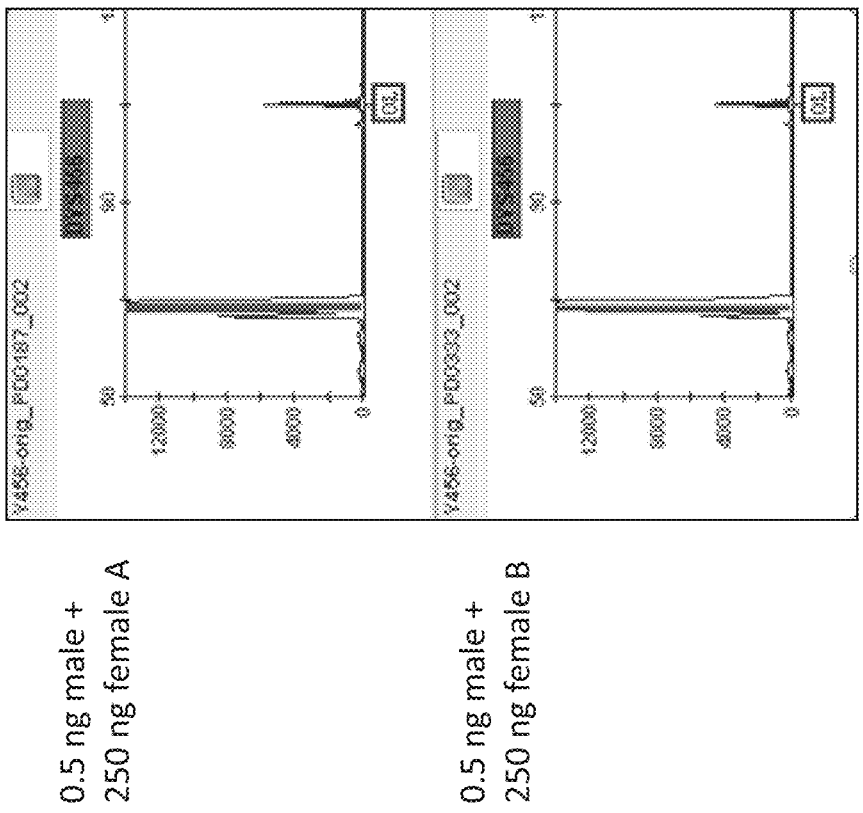
FIG. 14

MULTIPLEX Y-STR ANALYSIS

This application is a divisional under 35 U.S.C. § 120 of pending U.S. application Ser. No. 14/727,442 filed Jun. 1, 2015, which is a divisional of U.S. application Ser. No. 13/828,443 filed Mar. 14, 2013 (now abandoned), which application claims the benefit of under 35 U.S.C. § 119(e) to U.S. Provisional Application No. 61/697,742 filed Sep. 6, 2012; U.S. Provisional Application No. 61/720,949 filed Oct. 31, 2012; U.S. Provisional Application No. 61/761,152 filed Feb. 5, 2013; and U.S. Provisional Application No. 61/765,323 filed Feb. 15, 2013; each of which disclosures is herein incorporated by reference in its entirety.

The section headings used herein are for organizational purposes only and should not be construed as limiting the subject matter described herein in any way.

FIELD

In general, the disclosed invention relates to the determination of the identity of short tandem repeat (STR) alleles on the Y chromosome of a human using a multiplex analysis process. A multiplex analysis that includes increased numbers of loci that can provide increased discrimination and sensitivity may accurately genotype a wider range of individuals.

BACKGROUND

The fields of forensics, paternity testing, cell line ID, and personalized medicine routinely use DNA-based techniques for identity determinations, genotyping, phenotypic prediction, and in the prediction and/or prevention of disease. DNA typing involves the analysis of select regions of genomic DNA, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

In recent years, the discovery and development of polymorphic short tandem repeats (STRs) as genetic markers has played an important role in DNA typing. STRs have become the primary means for human identity and forensic DNA testing.

In particular, Y-STR analysis is a valuable tool in a number of applications. Forensic applications include use in investigation of sexual assault cases where male DNA may be present in a sample that also contains an excess of female DNA. Y-STR analysis can be critical in excluding individuals from further inquiries. In another forensic application, a sample may include DNA from multiple male contributors. Y-STR analysis can be used to trace family relationship among males, either in forensic or other inheritance analyses, and can be used in missing person investigations. Additionally, Y-STR analysis can be used in paternity testing, including scenarios where the alleged father is not available for direct comparison.

One database used to assist investigators is the U.S. Y-STR Database, a searchable listing of 11- to 23-locus Y-STR haplotypes. The database is funded by the National Institute of Justice and managed by the National Center for Forensic Science (NCFS) in conjunction with the University of Central Florida. The U.S. Y-STR Database is a population database only and is intended for use in estimating Y-STR haplotype population frequencies for forensic case work purposes.

Several limitations exist for currently available Y-STR analysis kits. While haplotype databases are used to establish the frequency of a haplotype in specific populations, haplotype resolution (HR) of kits may vary across populations (Vermeulen et al., (2009) FSIG 3:205-213). Secondly, using current kits, a male relative of a suspected individual may not be excluded. Relatives separated by up to 20 generations may have Y-STR profiles indistinguishable from each other, according to current analyses (Ballantyne et al. (2010): Am J Hum Genet 87:341-353). Thirdly, adventitious matches increase as more male profiles are added to Y-STR frequency databases. Therefore, there exists a need in the art, to improve Y-STR multiplex analysis systems, assays, kits, and methods.

SUMMARY OF SOME EMBODIMENTS OF THE INVENTION

In one aspect, the invention provides a set of amplification primers including primers for the amplification of at least 11 Y-STR markers where the primers are configured to provide each set of amplicons of the at least 11 Y-STR markers having a base pair size less than about 220 base pairs. In some embodiments, detection of amplicon base pair size may be performed by a fluorescence detection technique. In some embodiments, detection of amplicon base pair size may be performed by a mobility-dependent analytical technique. The mobility-dependent analytical technique may be capillary electrophoresis. In some other embodiments, detection of the amplicon base pair size may be performed by a sequencing technique using no fluorescent dye labels. In some embodiments, the set of amplification primers may further include primers for the amplification of at least 5 additional Y-STR markers where the primers are configured to provide each set of amplicons of the at least 5 additional Y-STR markers having a base pair size greater than about 220 base pairs. In various embodiments, when the set of amplification primers amplify more than 11 Y-STR markers, then the set of amplification primers may be configured to provide all of the sets of amplicons of the more than 11 Y-STR markers having a base pair size less than about 410 base pairs. In various embodiments, when the set of amplification primers amplify more than 11 Y-STR markers, then the set of amplification primers may be configured to provide all of the sets of amplicons of the more than 11 Y-STR markers having a base pair size less than about 420 base pairs. In some embodiments, when the set of amplification primers amplify more than 11 Y-STR markers, then the amplification primer set may include primers for 25 Y-STR markers. In some embodiments, when the amplification primer set includes primers for 25 Y-STR markers, the set of amplification primers may include primers for at least two double copy markers. In some embodiments, the set of amplification primers may be labeled with one of at least 5 fluorescent dyes. In some embodiments, the set of amplification primers may be configured to provide each set of the amplicons of the at least 11 Y-STR markers labeled with one of at least 5 fluorescent dyes. The at least 5 fluorescent dyes used to label the primers and/or the amplicons may be configured to be spectrally distinct. The set of amplification primers may further include at least one amplification primer that includes a mobility modifier. The set of amplification primers for the amplification of at least 11 Y-STR markers may be configured to provide at least one set of amplicons of the Y-STR markers including a mobility modifier. In some embodiments, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the set of amplification primers amplifying the at least 11 Y-STR markers configured to provide each set of amplicons of the at least 11 Y-STR markers having a base pair size less than about 220 base pairs, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4.

In another aspect of the invention, a kit is provided for co-amplifying a set of loci of at least one DNA sample including primers for the amplification of at least 11 Y-STR markers where the primers are configured to provide each set of amplicons of the at least 11 Y-STR markers having a base pair size less than about 220 base pairs; and optionally, a size standard. In some embodiments, the kit may further include primers for the amplification of at least 5 Y-STR markers where the primers are configured to provide each set of amplicons of the at least 5 Y-STR markers having a base pair size greater than about 220 base pairs. The kit may include an amplification primer set for 25 Y-STR markers. In various embodiments, when the set of amplification primers amplify more than 11 Y-STR markers, then the set of amplification primers may be configured to provide all of the sets of amplicons of the more than 11 Y-STR markers having a base pair size less than about 410 base pairs. In various embodiments, when the set of amplification primers amplify more than 11 Y-STR markers, then the set of amplification primers may be configured to provide all of the sets of amplicons of the more than 11 Y-STR markers having a base pair size less than about 420 base pairs. In some embodiments, the kit may include a set of amplification primers labeled with one of at least 5 fluorescent dyes. The at least 5 fluorescent dyes used to label the primers of the kit may be configured to be spectrally distinct. The kit may further include at least one amplification primer that includes a mobility modifier. In some embodiments, the kit including a set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the kit including a set of amplification primers amplifying the at least 11 Y-STR markers, where the primers are configured to provide each set of amplicons of the at least 11 Y-STR markers having a base pair size less than about 220 base pairs, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments, the kit including a set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the kit including a set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, when the kit includes a size standard, the kit further includes an allelic ladder.

In another aspect of the invention, a method is provided to amplify alleles of Y-STR markers of a human male including the steps of: contacting a sample suspected to contain a DNA sample of a human male with a set of amplification primers including primers for the amplification of the alleles of at least 11 Y-STR markers; and amplifying the sample thereby forming a plurality of sets of amplicons of the at least 11 Y-STR markers where each set of the amplicons has a base pair size less than about 220 base pairs. The method may further include the step of detecting each set of amplicons whereby the alleles of the at least 11 Y-STR markers are identified. In some embodiments, the detecting step is performed by separating the plurality of sets of amplicons using a mobility dependent analysis, where the plurality of sets of amplicons is fluorescently labeled. In other embodiments, the detecting step does not detect fluorescence. In embodiments, when the detecting step does not detect fluorescence, the detecting step may include ion semiconductor detection, pyrophosphate release detection, or mass spectrometry detection. In various embodiments of the method, the set of amplification primers may further include primers for the amplification of at least 5 additional Y-STR markers where the primers may be configured to provide each set of amplicons of the at least 5 additional Y-STR markers having a base pair size greater than about 220 base pairs. In various embodiments of the method, when the set of amplification primers amplifies more than 11 Y-STR markers, then the set of primers may be configured to provide all of the sets of amplicons of the more than 11 Y-STR markers having a base pair size less than about 410 base pairs. In various embodiments of the method, when the set of amplification primers amplifies more than 11 Y-STR markers, then the set of primers may be configured to provide all of the sets of amplicons of the more than 11 Y-STR markers having a base pair size less than about 420 base pairs. In some embodiments of the method, the amplification primer set may include 25 Y-STR markers. In some embodiments, the set of amplification primers may be labeled with one of at least 5 fluorescent dyes. In some other embodiments, each set of the amplicons of the at least 11 Y-STR markers may be labeled with one of at least 5 fluorescent dyes. In various embodiments of the method, the at least 5 fluorescent dyes used to label the primers and/or the amplicons may be configured to be spectrally distinct. The set of amplification primers used in the method may further include at least one amplification primer that includes a mobility modifier. In some embodiments of the method, the at least one set of amplicons may include a mobility modifier. In various embodiments of the methods, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the set of amplification primers amplifying the at least 11 Y-STR markers, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments of the method, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, the method includes a set of amplification primers for the amplification of the alleles of 27 Y-STR markers.

In yet another aspect, the invention provides a set of amplification primers including primers for the amplification of at least 22 Y-STR markers where at least 5 of the Y-STR markers are rapidly mutating loci. In some embodiments, the at least 5 rapidly mutating Y-STR markers include DYF387S1ab, DYS449, DYS570, DYS576, and DYS627. In some embodiments, the at least 5 rapidly mutating Y-STR markers include DYS518. In various embodiments, the set of amplification primers configured to amplify the at least 22 Y-STR markers may be further configured to provide each set of amplicons of at least 11 Y-STR markers having a base pair size less than about 220 base pairs. In other embodiments, the set of amplification primers for the amplification of at least 22 Y-STR markers may be configured to provide sets of amplicons for the at least 22 Y-STR markers each having a base pair size of less than about 410 base pairs. In other embodiments, the set of amplification primers for the amplification of at least 22 Y-STR markers may be configured to provide sets of amplicons for the at least 22 Y-STR markers each having a base pair size of less than about 420 base pairs. In some embodiments, detection of amplicon base pair size may be performed by fluorescence detection. In some embodiments, detection of amplicon base pair size may be performed by a mobility-dependent analytical technique. The mobility-dependent analytical technique may be capillary electrophoresis. In some other embodiments, detection of the amplicon base pair size may be performed by a sequencing technique using no detection of fluorescent dye labels. The amplification primer set may include 25 Y-STR markers. In some embodiments, the set of amplification primers is labeled with one of at least 5 fluorescent dyes. In some embodiments, each set of the amplicons of the at least 22 Y-STR markers is labeled with one of at least 5 fluorescent dyes. The at least 5 fluorescent dyes used to label the primers and/or the amplicons may be configured to be spectrally distinct. The set of amplification primers may further include at least one amplification primer that includes a mobility modifier. The set of amplification primers for the amplification of at least 22 Y-STR markers may be configured to provide at least one set of amplicons of the Y-STR markers where the at least one set of amplicons includes a mobility modifier. In some embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS570, DYS576, DYS627, DYS635, and Y-GATA-H4. In other embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS518, DYS570, DYS576, DYS627, DYS635, and Y-GATA-H4. A kit for co-amplifying a set of loci of at least one DNA sample may be provided, including a set of amplification primers for the amplification of at least 22 Y-STR markers where at least 5 of the Y-STR markers are rapidly mutating loci; and optionally, a size standard. In some embodiments, the size standard is an allelic ladder.

In yet another aspect, a method is provided to amplify alleles of Y-STR markers of a human male including the steps of: contacting a sample which may contain a DNA sample of a human male with a set of amplification primers including primers for the amplification of the alleles of at least 22 Y-STR markers, wherein at least 5 of the Y-STR markers are rapidly mutating loci; and amplifying the sample thereby forming a plurality of sets of amplicons of the at least 22 Y-STR markers. In some embodiments of the method, a set of amplification primers of the alleles of at least 23 Y-STR markers are provided, wherein at least 5 of the Y-STR markers are rapidly mutating loci. In yet other embodiments, a set of amplification primers of the alleles of 27 Y-STR markers are provided, wherein at least 5 of the Y-STR markers are rapidly mutating loci. In some embodiments, the 27 Y-STR markers include 2 Y-STR markers having double copy markers contributing to the total number of Y-STR markers. In some embodiments, each set of the amplicons of at least 11 of the at least 22 Y-STR markers has a base pair size less than about 220 base pairs. In other embodiments, each set of the amplicons of at least 11 of at least 23 Y-STR markers has a base pair size less than about 220 base pairs. In yet other embodiments, each set of the amplicons of at least 11 of 27 Y-STR markers has a base pair size less than about 220 base pairs. In various embodiments of the method, a set of amplification primers including primers for the amplification of the alleles of at least 22 Y-STR markers are provided, wherein at least 6 of the Y-STR markers are rapidly mutating loci. In various embodiments of the method, a set of amplification primers including primers for the amplification of the alleles of at least 22 Y-STR markers are provided, wherein at least 7 of the Y-STR markers are rapidly mutating loci. The method may further include the step of detecting each set of amplicons whereby the alleles of at least 22 Y-STR markers are identified. In some embodiments, the alleles of at least 23 Y-STR markers are identified. In yet other embodiments, the alleles of 27 Y-STR markers are identified. In some embodiments, the detecting step is a fluorescence detection step. In some embodiments, the detecting step is performed by separating the plurality of sets of amplicons using a mobility dependent analysis, where the plurality of sets of amplicons is fluorescently labeled. In other embodiments, the detecting step does not detect fluorescence. In embodiments, when detecting steps do not detect fluorescence, the detecting step may include ion semiconductor detection, pyrophosphate release detection, or mass spectrometry detection. In some embodiments, the at least 11 Y-STR markers having amplicons having a base pair size of less than about 220 base pairs are DYS576, DYS389I, DYS460, DYS458, DYS19, DYS456, DYS390, DYS570, DYS437, DYS393, and DYS439. In some the embodiments, the at least 5 rapidly mutating Y-STR markers are selected from the group consisting of DYF387S1ab, DYS449, DYS518, DYS570, DYS576, and DYS627. In other embodiments, the at least 5 rapidly mutating Y-STR markers are 6 rapidly mutating Y-STR markers.

In another aspect, a method of male individual identification is provided, including the steps of: contacting a sample containing a nucleic acid of a human male with a set of amplification primers including primers for the amplification of the alleles of at least 11 Y-STR markers; and amplifying the sample thereby forming a plurality of sets of amplicons of the at least 11 Y-STR markers where each set of the amplicons has a base pair size less than about 220 base pairs; and detecting each set of amplicons whereby the alleles of the male individual are identified. In various embodiments of the methods, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the step of amplifying the at least 11 Y-STR markers, may include amplifying at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments of the method, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, the method includes a set of amplification primers for the amplification of the alleles of more than 11 Y-STR markers. In other embodiments, the plurality of sets of amplicons of the more than 11 Y-STR markers where the plurality of sets of the amplicons has a base pair size less than about 410 base pairs. In some embodiments, the detecting step is a fluorescence detection step. In some embodiments, the method further includes the step of comparing the alleles identified for a first male individual to the alleles identified for a second male individual, whereby the first male individual is differentiable from the second male individual. In some embodiments, the first male individual has a similar paternal genetic lineage as the second male individual.

These embodiments and other features of the present teachings will become more apparent from the description herein.

BRIEF DESCRIPTION OF THE DRAWINGS

FIG. 9 is a table comparing selected Y-STR marker panels from various sources to Panel 6 and includes the number of alleles for each panel.

FIG. 12 is a table comparing selected Y-STR marker panels from various sources to Panel 7 and includes the number of alleles for each panel.

FIG. 14 is a graphical representation of the effect of primer length for DYS456 marker when amplifying selected male/female DNA mixtures.

DESCRIPTION OF EXEMPLARY EMBODIMENTS

Figure 1:
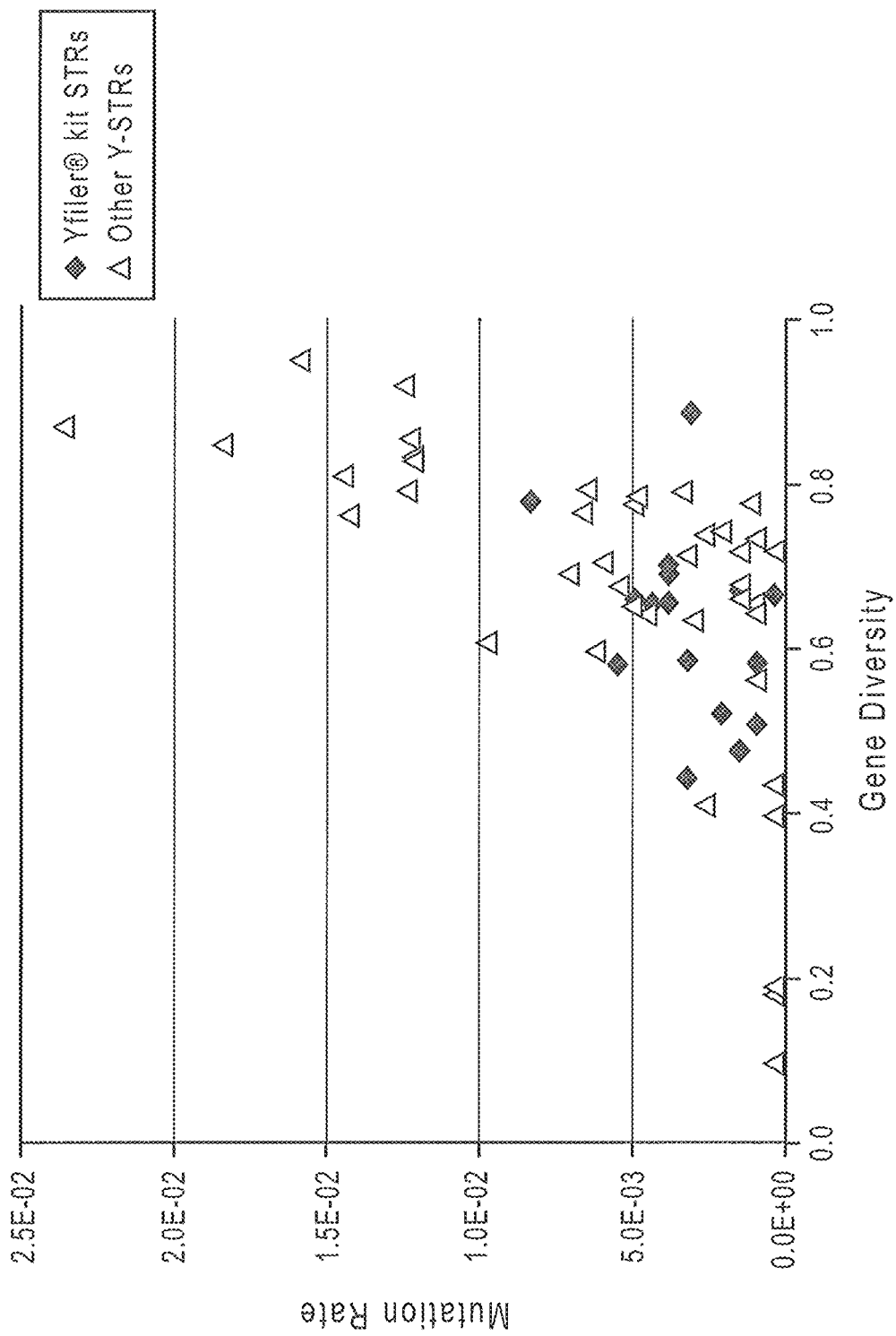
FIG. 1 is a graphical representation of selected Y-STR markers, where Gene Diversity values are graphed on the x axis and mutation rate is mapped along the y axis.

For the purposes interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

The term "allele" as used herein refers to a genetic variation associated with a gene or a segment of DNA, i.e., one of two or more alternate forms of a DNA sequence occupying the same locus. In some embodiments, an allele within a locus encompasses a nucleic acid molecule having a polymorphic tandemly repeated base pair motif. It is the variation in the number of repeat units in tandem that distinguish alleles within a locus.

The term "wild type allele" or "predominant allele" are used interchangeably herein and as used herein refer to the most frequently occurring allele found in a given species, genus, family, segment, tribe, ethnicity, or racial population. The wild type allele can be considered the most common allele.

The term "variant allele" as used herein refers to a variation from the most frequently occurring allele. It can also refer to, at one or more nucleic acid positions, a change in the nucleic acid sequence at one or more positions resulting in one or more differences when compared to the most common allele at one or more nucleic acid positions as found in the allele for a given species, genus, family, segment, tribe, ethnicity, or racial population.

The term "allelic ladder" as used herein refers to a nucleic acid size standard that encompasses size standards for one or more alleles for a particular STR marker. The allelic ladder serves as a reference standard and nucleic acid size marker for the amplified allele(s) from the STR marker.

As used herein, the terms "amplification primer" and "oligonucleotide primer" are used interchangeably and refer to an oligonucleotide, capable of annealing to an RNA or DNA region adjacent a target sequence, and serving as an initiation primer for DNA synthesis under suitable conditions well known in the art. Typically, a PCR reaction employs an "amplification primer pair" also referred to as an "oligonucleotide primer pair" including an "upstream" or "forward" primer and a "downstream" or "reverse" primer, which delimit a region of the RNA or DNA to be amplified. A first primer and a second primer may be either a forward or reverse primer and are used interchangeably herein and are not to be limiting.

As used herein, "amplify" refers to the process of enzymatically increasing the amount of a specific nucleotide sequence. This amplification is not limited to but is generally accomplished by PCR. As used herein, "denaturation" refers to the separation of two complementary nucleotide strands from an annealed state. Denaturation can be induced by a number of factors, such as, for example, ionic strength of the buffer, temperature, or chemicals that disrupt base pairing interactions. As used herein, "annealing" refers to the specific interaction between strands of nucleotides wherein the strands bind to one another substantially based on complementarity between the strands as determined by Watson-Crick base pairing. It is not necessary that complementarity be 100% for annealing to occur. As used herein, "extension" refers to the amplification cycle after the primer oligonucleotide and target nucleic acid have annealed to one another, wherein the polymerase enzyme catalyzes primer extension, thereby enabling amplification, using the target nucleic acid as a replication template.

The terms "amplicon," "amplification product" and "amplified sequence" are used interchangeably herein and refer to a broad range of techniques for increasing polynucleotide sequences, either linearly or exponentially and can be the product of an amplification reaction. An amplicon can be double-stranded or single-stranded, and can include the separated component strands obtained by denaturing a double-stranded amplification product. In certain embodiments, the amplicon of one amplification cycle can serve as a template in a subsequent amplification cycle. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods can include thermal-cycling or can be performed isothermally. In various embodiments, the term "amplification product" and "amplified sequence" includes products from any number of cycles of amplification reactions.

As used herein, the term "base pair motif" refers to the nucleobase sequence configuration including, but not limited to, a repetitive sequence, a sequence with a biological significance, a tandem repeat sequence, and so on.

As used herein, the term "comparing" broadly refers to differences between two or more nucleic acid sequences. The similarity or differences can be determined by a variety of methods, including but not limited to: nucleic acid sequencing, alignment of sequencing reads, gel electrophoresis, restriction enzyme digests, single strand conformational polymorphism, and so on.

The terms "detecting" and "detection" are used in a broad sense herein and encompass any technique by which one can determine the presence of or identify a nucleic acid sequence. In some embodiments, detecting may include quantitating a detectable signal from the nucleic acid, including without limitation, a real-time detection method, such as quantitative PCR ("Q-PCR"). In some embodiments, detecting may include determining the sequence of a sequencing product or a family of sequencing products generated using an amplification product as the template; in some embodiments, such detecting may include obtaining the sequence of a family of sequencing products. In other embodiments detecting can be achieved through measuring the size of a nucleic acid amplification product.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to DNA or RNA in any form. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA molecules. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, is generally substantially free of other cellular material or culture medium when produced by recombinant techniques, or free of chemical precursors or other chemicals when chemically synthesized.

As used herein, the term "flanking sequence" broadly refers to nucleic acid sequence 5' and/or 3' of a target nucleic acid sequence, including, but not limited to, a short tandem repeat sequence. The flanking sequence can be within an amplification product or outside, i.e., flanking, the amplification product. Amplification primers can be selected to hybridize to sequences flanking the variable portion of an STR marker so as to produce amplicons of a size indicative of a specific allele of the STR marker.

As used herein, the term "short tandem repeat (STR) loci" refers to regions of a genome which contains short, repetitive sequence elements of 2 to 7 base pairs in length. Each sequence element is repeated at least once within an STR and is referred to herein as a "repeat unit." The term STR also encompasses a region of genomic DNA wherein more than a single repeat unit is repeated in tandem or with intervening bases, provided that at least one of the sequences is repeated at least two times in tandem. Examples of STRs, include but are not limited to, a triplet repeat, e.g., ATC in tandem, e.g., ATCATCATCATCAACATCATC (SEQ ID NO: 1); a 4-peat (tetra-repeat), e.g., GATA in tandem, e.g., GATAGATAGATACATAGATA (SEQ ID NO: 2); and a 5-peat (penta-repeat), e.g., ATTGC in tandem, e.g., ATTG-CATTGCATTGC (SEQ ID NO: 3) and so on. Information about specific STRs that can be used as genetic markers can be found in, among other places, the STRbase.

As used herein, the terms "imperfect repeat", "incomplete repeat", and "variant repeat" refer to a tandem repeat within which the repeat unit, though in tandem, has sequence interruptions (additions or deletions) between one or more repeat units, e.g., ATCG ATCG AACG ATCG ATCG (SEQ ID NO:4), where the third repeat unit is not identical to the other repeat units and so an imperfect repeat; an incomplete repeat can be seen as a tandem repeat in which the number of base pairs in a repeat unit is an incomplete repeat, e.g., allele 9 of the TH01 locus contains nine 4-peat repeat units ([AATG]$_9$ for the complete repeat "AATG" for the TH01 locus), but the 9.3 allele contains the nine "AATG" repeats and one incomplete repeat, "ATG" of three nucleotides, an incomplete repeat, i.e., [AATG]$_6$ATG[AATG]$_3$; while a variant repeat has variation(s) within the repeat unit, e.g., ATCC ATCG ATCC ATCG ATCG ATCC ATCC (SEQ ID NO:5), where the 4-peat repeat unit has a variant base pair at the fourth position of the repeat unit, either a "C" or a "G" nucleotide.

As used herein, the term "polymorphic short tandem repeat loci" refers to STR loci in which the number of repetitive sequence elements (and net length of the sequence) in a particular region of genomic DNA varies from allele to allele, and from individual to individual.

"Genetic markers" are generally alleles of genomic DNA loci with characteristics of interest for analysis, such as DNA typing, in which individuals are differentiated based on variations in their DNA. Most DNA typing methods are designed to detect and analyze differences in the length and/or sequence of one or more regions of DNA markers known to appear in at least two different forms, or alleles, in a population. Such variation is referred to as "polymorphism," and any region of DNA in which such a variation occurs is referred to as a "polymorphic locus." One possible method of performing DNA typing involves the joining of PCR amplification technology (K B Mullis, U.S. Pat. No. 4,683,202) with the analysis of length variation polymorphisms. PCR traditionally could only be used to amplify relatively small DNA segments reliably; i.e., only amplifying DNA segments under 3,000 bases in length (M. Ponce and L. Micol (1992), NAR 20(3):623; R. Decorte et al. (1990), DNA CELL BIOL. 9(6):461 469). Short tandem repeats (STRs), minisatellites and variable number of tandem repeats (VNTRs) are some examples of length variation polymorphisms. DNA segments containing minisatellites or VNTRs are generally too long to be amplified reliably by PCR. By contrast STRs, containing repeat units of approximately three to seven nucleotides, are short enough to be useful as genetic markers in PCR applications, because amplification protocols can be designed to produce smaller products than are possible from the other variable length regions of DNA.

As used herein, the term "haplotype" is a selected group of alleles on a Y-chromosome that are transmitted together.

The term "locus" as used herein refers to a specific physical position on a chromosome or a nucleic acid molecule. Alleles of a locus are located at identical sites on homologous chromosomes. "Loci" the plural of "locus" as used herein refers to a specific physical position on either the same or a different chromosome as well as either the same or a different specific physical position on the nucleic acid molecule.

As used herein, the term "nucleic acid sample" refers to nucleic acid found in biological samples according to the present invention including, but not limited to, for example, hair, feces, blood, tissue, urine, saliva, cheek cells, vaginal cells, skin, for example skin cells contained in fingerprints, bone, tooth, buccal sample, amniotic fluid containing placental cells, and amniotic fluid containing fetal cells and semen. It is contemplated that samples may be collected invasively or noninvasively. The sample can be on, in, within, from or found in conjunction with a fiber, fabric, cigarette, chewing gum, adhesive material, soil or inanimate objects. "Sample" as used herein, is used in its broadest sense and refers to a sample suspected of containing a nucleic acid and may entail a cell, chromosomes isolated from a cell (e.g., a spread of metaphase chromosomes), genomic DNA, RNA, cDNA and the like. Samples can be of animal or vegetable origins encompassing any organism containing nucleic acid, including, but not limited to, bacteria, viruses, plants, livestock, household pets, and human samples.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, CA.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used herein, the terms "polynucleotide", "oligonucleotide", and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may include any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

The term "primer" refers to a polynucleotide (oligonucleotide) and analogs thereof that is capable of selectively hybridizing to a target nucleic acid or "template," a target region flanking sequence or to a corresponding primer-binding site of an amplification product; and allows the synthesis of a sequence complementary to the corresponding polynucleotide template, flanking sequence or amplification product from the primer's 3' end. Typically a primer can be between about 10 to 100 nucleotides in length and can provide a point of initiation for template-directed synthesis of a polynucleotide complementary to the template, which can take place in the presence of appropriate enzyme(s), cofactors, substrates such as nucleotides (dNTPs) and the like.

As used herein, the term "primer-binding site" refers to a region of a polynucleotide sequence, typically a sequence flanking a target region and/or an amplicon that can serve directly, or by virtue of its complement, as the template upon which a primer can anneal for any suitable primer extension reaction known in the art, for example, but not limited to, PCR. It will be appreciated by those of skill in the art that when two primer-binding sites are present on a double-stranded polynucleotide, the orientation of the two primer-binding sites is generally different. For example, one primer of a primer pair is complementary to and can hybridize with the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not, encompass the same sequence as or at least some of the sequence of the target flanking sequence or its complement.

Those in the art understand that as a target region is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "tandem repeat" refers to a repetitive sequence occurring in sequential succession.

As used herein, the term "tandem repeat locus" refers to a locus containing tandem repeats.

As used herein, the terms "target polynucleotide," "nucleic acid target" and "target nucleic acid" are used interchangeably herein and refer to a particular nucleic acid sequence of interest. The "target" can be a polynucleotide sequence that is sought to be amplified and can exist in the presence of other nucleic acid molecules or within a larger nucleic acid molecule. The target polynucleotide can be obtained from any source, and can include any number of different compositional components. For example, the target can be nucleic acid (e.g. DNA or RNA). The target can be methylated, non-methylated, or both. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in, for example, but not limited to, forensics samples (see for example Butler, 2001, Forensic DNA Typing: Biology and Technology Behind STR Markers). The target polynucleotides of the present teachings can be derived from any of a number of sources. These sources may include, but are not limited to, whole blood, a tissue biopsy, lymph, bone, bone marrow, tooth, amniotic fluid, hair, skin, semen, anal secretions, vaginal secretions, perspiration, saliva, buccal swabs, various environmental samples (for example, agricultural, water, and soil), research samples generally, purified samples generally, and lysed cells. It will be appreciated that target polynucleotides can be isolated from samples using any of a variety of procedures known in the art, for example the PrepSEQ™ Kits (from Applied Biosystems), Boom et al., and U.S. Pat. No. 5,234,809, etc. It will be appreciated that target polynucleotides can be cut or sheared prior to analysis, including the use of such procedures as mechanical force, sonication, restriction endonuclease cleavage, or any method known in the art.

The nomenclature for the particular STR loci as used herein refer to the names assigned to these loci as they are known in the art. The loci are identified, for example, in the various references and by the various accession numbers in the list that follows, all of which are incorporated herein by reference in their entirety. The list of references that follows is merely intended to be exemplary of sources of locus information. Where appropriate, the current Accession Number as of time of filing is presented, as provided by GenBank® (National Center for Biotechnology Information, Bethesda, MD).

New Y-STR multiplex analysis panels are described here, which provide surprising improvements in the ability to provide haplotype resolution (HR) variation across more diverse populations, ability to exclude a male relative of a suspected individual, and/or ability to resolve adventitious matches in more highly populated Y-STR frequency databases. There is a need in the field for such improvements, as currently, the AmpFlSTR® Yfiler® multiplex analysis has a HR in European populations of 0.989, but only a HR of 0.905 globally (Vermeulen, Forensic Science International Genetics 3(2009) 205-213). Additionally, the Y-STR multiplex panels described here provide better overall balance of the multiplex analysis identifying more robustly minor contributor alleles in a mixture, thus providing either better male/male resolution and/or better identification of male alleles in male/female mixtures with high female background, compared to commercially available kits. Further, the Y-STR multiplex panels provide: improved resistance to inhibitors of PCR providing higher recovery of alleles; higher sensitivity, providing higher number of alleles identified when amplifying small amounts of input DNA; and shorter analysis times compared to the currently available commercial kits.

In the Y-STR multiplex assay panels described here, the Y-STR markers currently used in the Yfiler® multiplex panel have also been included because existing Y-STR databases are already populated with profiles containing this information. The use of additional Y-STR markers has been evaluated. A large number of Y-STR loci have been identified but not all Y-STR loci are necessarily suitable for inclusion in a multiplex panel for a number of reasons. Multicopy markers may be challenging when interpreting data, especially in samples having several DNA sources or potential contaminants. For example, markers with more than two copies (non-limiting examples include DYF399S1abs and DYF403S1 1abc/II) may not be considered for inclusion in some embodiments of the invention.

Use of loci having higher gene diversity has been investigated to decrease the incidence of adventitious matches. For exclusion of close patrilineal relatives of an individual, markers with a high mutation rate may be beneficial. On the other hand, in kinship analysis markers with high mutation rates may complicate analysis; including additional markers with lower mutation rates may aid in lineage differentiation. Balancing those factors may provide a multiplex panel with the broadest applicability.

Newly added Y-STR markers provide improvements beyond the capability of currently commercialized Y-STR multiplex assays, including features such as (1) the use of mini-STRs which can facilitate analysis of degraded DNA, (2) the inclusion of highly discriminating markers which may better differentiate paternal lineages in populations with low Y-chromosome diversity and (3) the use of rapidly mutating markers to increase the ability to distinguish between close relatives. Additionally selecting markers having a maximum of two copies per marker (e.g. DYS385ab) may simplify analysis.

Other factors contributing to selection of Y-STR loci for improved multiplex analysis include primer compatibility within the multiplex, strict male specificity for the associated primers, and potential for use as a mini-STR. Another advantage of including mini-STRs is the potential for shortening the time for the electrophoretic separations used to identify the alleles that are amplified in the multiplex, as greater numbers of STR markers may be included in an electrophoretic separation of about 410 bp. Adding a sixth dye channel also permits an increase in the number of Y-STR loci examined while maintaining a shorter electrophoretic separation.

Gene Diversity. Average gene diversity (GD) values were gathered from available population studies as listed in TABLE 1 for a candidate list of 39 loci. These 39 loci were further evaluated for the possibility of inclusion in the improved Y-STR multiplex panels, as these loci offer the potential for greater discrimination, particularly in non-European populations, as shown in the key to TABLE 1.

TABLE 1

| No. Marker | Ave. GD | Gene Diversity (GD) | Mutation Rate(3) |
|---|---|---|---|
| 1 DYF387S1 ab | 0.950 | 0.950[W3] | 0.0159 |
| 2 DYF404S1 ab | 0.920 | 0.920[w3] | 0.0125 |
| 3 DYF406S1 | 0.741 | 0.741[EU1] | 0.0038 |
| 4 DYS19 | 0.655 | 0.747[W1], 0.676[US2], 0.457[Cau3], 0.718[AA3], 0.688[CN1], 0.700[KR1], 0.683[KR2], 0.717[KR3], 0.688[JP1], 0.758[PL1], 0.700[BY1], 0.516[ES1], 0.563[ES4], 0.688[EU1], 0.535[NL], 0.638[CZ1], 0.694[CA1], 0.691[MZ1], 0.480[ZA-E1], 0.700[ZA-I1], 0.72[ZA-X1] | 0.0044 |
| 5 DYS385 ab | 0.887 | 0.973[W1], 0.912[US2], 0.541[Cau3], 0.553[AA3], 0.793[CN1], 0.963[KR1], 0.961[KR2], 0.948[JP1], 0.875[PL1], 0.845[BY1], 0.800[ES1], 0.840[ES4], 0.875[EU1], 0.843[NL1], 0.820[CZ1], 0.933[CA1], 0.922[MZ1] | 0.0031 |
| 6 DYS388 | 0.435 | 0.360[W1], 0.365[US2], 0.330[US3], 0.437[CN1], 0.536[KR1], 0.509[KR2], 0.5083[KR3], 0.400[PL1], 0.449[BY1], 0.334[ES1], 0.553[NL1] | 0.0004 |
| 7 DYS389 I | 0.581 | 0.669[W1], 0.549[US2], 0.541[Cau3], 0.553[AA3], 0.582[CN1], , 0.718[KR1], 0.667[KR2], 0.666[KR3], 0.646[JP1], 0.460[BY1], 0.563[ES1], 0.575[ES4], 0.5498[EU1], 0.544[NL1], 0.546[CZ1], 0.555[CA1], 0.495[MZ1] | 0.0055 |
| 8 DYS389 II | 0.691 | 0.724[W1], 0.736[US2], 0.590[Cau3], 0.701[AA3], 0.767[CN1], 0.690[KR1], 0.735[KR2], 0.726[KR3], 0.769[JP1], 0.799[PL1], 0.676[BY1], 0.507[ES1], 0.563[ES4], 0.764[[EU1], 0.53[NL1], 0.780[CZ1], 0.669[CA1], 0.714[MZ1] | 0.0038 |
| 9 DYS390 | 0.672 | 0.789[W1], 0.764[US2], 0.704[Cau3], 0.659[AA3], 0.696[CN1], 0.673[KR1], 0.626[KR2], 0.669[KR3], 0.765[JP1], 0.654[PL1], 0.687[ES1], 0.573[ES2], 0.606[ES4], 0.752[EU1], 0.681[NL1], 0.691[CZ1], 0.497[CA1], 0.528[MZ1], 0.680[ZA-E1], 0.830[ZA-I1], 0.580[ZA-X1] | 0.0015 |
| 10 DYS391 | 0.444 | 0.532[W1], 0.534[US2], 0.522[Cau3], 0.417[AA3], 0.393[CN1], 0.616[KR1], 0.403[KR2], 0.292[KR3], 0.209[JP1], 0.504[PL1], 0517[BY1], 0594[ES1], 0561[ES4, 0.509[EU1], 0.527[NL1], 0.541[CZ1], 0.399[CA1], 0.305[MZ1], 0.540[ZA-E1], 0.280[ZA-I1], 0.12[ZA-X1] | 0.0032 |
| 11 DYS392 | 0.509 | 0.768[W1], 0.609[US2], 0.602[Cau3], 0.416[AA3], 0.642[CN1], 0.691[KR1], 0.684[KR2], 0.693[KR3], 0.651[JP1], 0.321[PL1], 0.346[BY1], 0.501[ES1], 0.565[ES4], 0.5782[EU1], 0.618[CZ1], 0.391[CA1], 0.018[MZ1], 0.580[ZA-E1], 0.450[ZA-I1], 0.050 [ZA-X1] | 0.0010 |
| 12 DYS393 | 0.522 | 0.664[W1], 0.485[US2], 0.322[Cau3], 0.608[AA3], 0.616[CN1], 0.659[KR1], 0.638[KR2], 0.634[KR3], 0.556[JP1], 0.342[PL1], 0.381[ES1], 0.463[ES4], 0.457[EU1], 0.410[NL1], 0.503[CZ1], 0.670[CA1], 0.310[ZA-E1], 0.690[ZA-I1], 0.580[ZA-X1] | 0.0021 |
| 13 DYS437 | 0.477 | 0.565[W1], 0.637[US2], 0.610[US3], 0.415[KR1], 0.255[JP1], 0.457[PL1], 0.464[BY1], 0.543[ES1], 0.575[ES2], 0.602[ES3], 0.574[ES4], 0.644[EU1], 0.581[NL1], 0.584[BR1], 0.312[CA1], 0.053[MZ1], 0.546[ZA-I2], 0.551[ZA-E2], 0.090[ZA-X2] | 0.0015 |

TABLE 1-continued

| No. | Marker | Ave. GD | Gene Diversity (GD) | Mutation Rate(3) |
|---|---|---|---|---|
| 14 | DYS438 | 0.583 | 0.598[W1], 0.691[US2], 0.617[Cau3], 0.498[AA3] 0.467[CN3], 0.527[CN5], 0.640[KR1], 0.607[JP1], 0.584[PL1], 0.578[BY1], 0.540[ES2], 0.554[ES3], 0.589[ES4], 0.694[EU1], 0.584[NL1], 0.703[CZ1], 0.690[BR1], 0.520[CA1], 0.401[MZ1] | 0.0010 |
| 15 | DYS439 | 0.656 | 0.694[W1], 0.656[US2], 0.666[Cau3], 0.652[AA3], 0.715[CN3], 0.666[CN5], 0.600[KR1], 0.592[JP1], 0.688[PL1], 0.703[BY1], 0.668[ES1], 0.628[ES2], 0.684[ES3], 0.655[ES4], 0.708[EU1], 0.636[NL1], 0.678[CZ1], 0.679[BR1], 0.603[CA1], 0.612[MZ1], 0.620[ZA-E1], 0.720[ZA-I1], 0.570[ZA-X1] | 0.0038 |
| 16 | DYS444 | 0.666 | 0.592[US1], 0.620[Cau1], 0.650[AA1], 0.610[US3], 0.767[CN1], 0.756[CN5] | 0.0055 |
| 17 | DYS447 | 0.742 | 0.781[W1], 0.747[US2], 0.580[Cau1], 0.770[AA1], 0.640[Cau2], 0.780[AA2], 0.770[US3], 0.803[CN5], 0.776[EU1], 0.702[NL1], 0.719[BR1], 0.871[ZA-I2], 0.679[ZA-E2], 0.774[ZA-X2] | 0.0021 |
| 18 | DYS448 | 0.666 | 0.782[W1], 0.721[US2], 0.550[Cau2], 0.710[AA2], 0.73[US3], 0.602[Cau3], 0.699[AA3], 0.745[CN2], 0.767[CN4], 0.704[CN5], 0.725[JP1], 0.462[BY1], 0.585[EU1], 0556[NL1], 0.722[CZ1], 0.669[BR1], 0.588[ZA-I2], 0.643[ZA-E2], 0.689[ZA-X2] | 0.0004 |
| 19 | DYS449 | 0.831 | 0.874[W1], 0.832[US1], 0.740[Cau1], 0.860[AA1], 0.770[Cau2], 0.870[AA2], 0.840[US3], 0.843[KR3], 0.857[EU1], 0.809[NL1], 0.877[CZ1], 0.831[BR1], 0.780[ZA-E1], 0.880[ZA-I1], 0.780[ZA-X1], 0.867[ZA-I2], 0.787[ZA-E2], 0.821[ZA-X2], 0.864[ZA1] | 0.0122 |
| 20 | DYS456 | 0.660 | 0.706[W1], 0.700[US2], 0.820[Cau2], 0.520[AA2], 0.670[US3], 0699[CN2], 0.716[CN3], 0.644[CN5], 0.474[JP1], 0.731[ES1], 0717[NL1], 0.796[Cz1], 0.691[BR1], 0.622[ZA-I2], 0.728[ZA-E2], 0.434[ZA-X2] | 0.0049 |
| 21 | DYS458 | 0.775 | 0.748[W1], 0.765[US2], 0.810[Cau2], 0.750[AA2], 0.821[CN2], 0.786[CN5], 0.821[JP1], 0.748[BY1], 0.787[NL1], 0.791[BR1], 0.780[ZA-E1], 0.780[ZA-I1], 0.690[ZA-X1] | 0.0084 |
| 22 | DYS459 ab | 0.694 | 0.647[US1], 0.67[Cau2], 0.75[AA2], 0.75[US3], 0.641[CN3], 0.704[NL1] | 0.0027 |
| 23 | DYS460 | 0.589 | 0.544[W1], 0.570[US2], 0.734[CN3], 0.699[CN5], 0.563[PL1], 0.607[BY1], 0.547[ES1], 0.624[ES2], 0.522[ES3], 0.577[ES4], 0.588[NL1], 0.550[BR1], 0.560[CA1], 0.555[MZ1] | 0.0062 |
| 24 | DYS471DYS610 | 0.873 | 0.844[Cau3], 0.902[AA3] | NA |
| 25 | DYS481 | 0.774 | 0.900[W2], 0.840[US3], 0.851[CN6], 0.776[CN7], 0.674[CN8], 0.752[CN9], 0.637[CN10], 0.860[JP1], 0.840[EU1], 0.700[ZA-E1], 0.680[ZA-I1], 0.800[ZA-X1], 0.689[ZA-I2], 0.712[ZA-E2], 0.816[ZA-X2], 0.851[ZA1] | 0.0050 |
| 26 | DYS487 | 0.455 | 0.62[W2]0.444[Cau3], 0.301[AA3] | 0.0018 |
| 27 | DYS488 | 0.239 | 0.58[W2], 0.28[Cau2], 0.05[AA2], 0.23[US3], 0.252[Cau3], 0.138[AA3], 0.242[CN6], 0.283[CN7], 0.22[CN8], 0.081[CN9], 0.271[CN10] | 0.0004 |
| 28 | DYS504 | 0.717 | 0.810[US1], , 0.752[Cau3], 0.718[AA3], 0.735[JP1], 0.672[ZA-I2], 0.674[ZA-E2], 0.661 [ZA-X2] | 0.0032 |
| 29 | DYS505 | 0.680 | 0.710[W2], 0.667[US1], 0.680[US3], 0.744[JP1], 0.599[EU1] | 0.0015 |
| 30 | DYS508 | 0.627 | 0.71[W2], 0.688[US1], 0.73[US3], 0.406[JP1], 0.602[EU1] | 0.0030 |
| 31 | DYS518 | 0.848 | 0.870[W3], 0.800[ZA-E1], 0.850[ZA-I1], 0.870[ZA-X1], 0.850[ZA-I2], 0.815[ZA-E2], 0.866[ZA-X2], 0.862[ZA1] | 0.0184 |

TABLE 1-continued

| No. Marker | Ave. GD | Gene Diversity (GD) | Mutation Rate(3) |
|---|---|---|---|
| 32 DYS522 | 0.641 | 0.740[W2], 0.659[US1], 0.600[Cau1], 0.630[AA1], 0.64[Cau2], 0.590[AA2], 0.640[US3], 0.691[CN4], 0.582[JP1], 0.641[EU1], | 0.0010 |
| 33 DYS526 I* | 0.780 | 0.780[W3] | 0.0027 |
| 34 DYS526 II* | 0.880 | 0.880[W3] | 0.0125 |
| 35 DYS527ab | 0.838 | 0.850[Cau1], 0.790[AA1], 0.850[Cau2], 0.780[AA2], 0.920[US3] | NA |
| 36 DYS532 | 0.760 | 0.777[US1], 0.815[ZA-I2], 0.764[ZA-E2], 0.686[ZA-X2] | 0.0032 |
| 37 DYS533 | 0.636 | 0.720[W2], 0.639[US1], 0.620[US3], 0.566[EU1] | 0.0050 |
| 38 DYS534 | 0.756 | 0.756[US1] | 0.0065 |
| 39 DYS540 | 0.467 | 0.62[W2], 0.441[US1], 0.340[JP1] | 0.0033 |
| 40 DYS547 | 0.870 | 0.870[W3] | 0.0236 |
| 41 DYS549 | 0.644 | 0.720[W2], 0.604[JP1], 0.608[EU1] | 0.0046 |
| 42 DYS552 | 0.621 | 0.729[ZA-I2], 0.630[ZA-E2], 0.503[ZA-X2 | 0.0027 |
| 43 DYS557 | 0.737 | 0.774[US1], 0.60[Cau1], 0.78[AA1], 0.66[Cau2], 0.78[AA2], 0.79[US3], 0.734[CN5], 0.72[ZA-E1], 0.86[ZA-I1], 0.67[ZA-X1] | 0.0038 |
| 44 DYS570 | 0.792 | 0.830[W3], 0.860[W2], 0.784[US1], 0.780[Cau2], 0.810[AA2], 0.790[US3], 0.822[JP1], 0.804[EU1], 0.770[NL1], 0.773[BR1], 0.750[ZA-E1], 0.820[ZA-I1], 0.700[ZA-X1] | |
| 45 DYS576 | 0.764 | 0.830[W3], 0.820[W2], 0.797[US1], 0.790[Cau2], 0.820[AA2], 0.830[US3], 0.802[CN6], 0.544[CN7], 0.537[CN8], 0.770[CN9], 0.766[CN10], 0.771[JP1], 0.772[EU1], 0.740[[NL1], 0.820[BR1], 0.778[ZA-I2], 0.752[ZA-E2], 0.746[ZA-X2] | 0.0143 |
| 46 DYS607 | 0.701 | 0.63[Cau2], 0.72[AA2], 0.77[US3], 0.684[NL1], 0.71[ZA-E1], 0.81[ZA-I1], 0.58[ZA-X1] | NA |
| 47 DYS612 | 0.810 | 0.850[W3], 0.770[ZA-E1], 0.800[ZA-I1], 0.810[ZA-X1], 0.809[ZA-I2], 0.764[ZA-E2], 0.829[ZA-X2], 0.849[ZA1] | |
| 48 DYS626 | 0.827 | 0.850[W3], 0.850[ZA-E1], 0.800[ZA-I1], 0.790[ZA-X1], 0.819[ZA-I2], 0.835[ZA-E2], 0.819[ZA-X2], 0.854[ZA1] | |
| 49 DYS627 | 0.860 | 0.860[US3] | 0.0123 |
| 50 DYS635 | 0.702 | 0.739[US1], 0.718[CN5], 0.656[JP1], 0.677[BY1], 0.758[BR1], 0.600[ZA-E1], 0.820[ZA-I1], 0.650[ZA-X1] | |
| 51 DYS643 | 0.745 | 0.820[W2], 0.755[US1], 0.780[US3], 0.718[JP1], 0.650[EU1] | 0.0015 |
| 52 DYS644 | 0.823 | .91[ZA-E1], 0.91[ZA-I1], 0.80[ZA-X1], 0.783[ZA-I2], 0.718[ZA-E2], 0.763[ZA-X2], 0.875[ZA1] | 0.0032 |
| 53 DYS685 | 0.823 | 0.786[Cau3], 0.859[AA3] | NA |
| 54 DYS688 | 0.895 | 0.89[Cau3], 0899[AA3] | NA |
| 55 DYS703 | 0.543 | .537[Cau3], 0.549[AA3] | NA |
| 56 DYS707 | 0.599 | 0.553[Cau3], 0.644[AA3] | NA |
| 57 DYS710 | 0.831 | 0.71[ZA-E1], 0.75[ZA-I1], 0.75[ZA-X1], 0.937[ZA-I2], 0.925[ZA-E2], 0.830[ZA-X2], 0.916[ZA1] | NA |
| 39 Y GATA H4 | 0.586 | 0.599[W1], 0.611[US2], 0.590[US3], 0.603[CN5], 0.572[JP1], 0.558[PL1], 0.656[BY1], 0.412[ES2], 0.604[ES3], 0.573[ES4], 0.623[NL1], 0.581[BR1], 0.549[MZ1], 0.656[ZA-I2], 0.588[ZA-E2], 0.598[ZA1] | |

*DYS526I/II is a multicopy marker similar to DYS389I/II, and not included in the list of potential new markers.

TABLE 1A

Population Background Key

| | | | |
|---|---|---|---|
| W1: World, N = 73, Ref. (3) | W2: World, N = 74, Ref. (4) | W3: World, N = 604, Ref. (1) | US1: USA, N = 660, Ref. (5) |
| US2: USA, N = 647, Ref. (6) | Cau1: USA-Caucasian, N = 50, Ref. (7) | AA1: USA-African American, N = 100, Ref. (7) | Cau2: USA-Caucasian, N = 98, Ref. (8) |
| AA2: USA-African American, N = 51, Ref. (8) | Cau3: USA-Caucasian, N = 114, Ref. (9) | AA3: USA-African American, N = 110, Ref. (9) | US3: USA, N = 572, Ref. (10) |
| CN1: China, N = 582, Ref. (11) | CN2: China, N = 108, Ref. (12) | CN3: China, N = 105, Ref. (13) | CN4: China-Han, N = 106, Ref. (14) |

TABLE 1A-continued

| Population Background Key | | | |
|---|---|---|---|
| CN5: China, N = 158, Ref. (15) | CN6: China-Daur, N = 38, Ref. (16) | CN7: China-Kazak, N = 39, Ref. (16) | CN8: China-Uighur, N = 37, Ref. (16) |
| CN9: China-Xibe, N = 34, Ref. (16) | CN10: China-Kirgiz, N = 26, Ref. (16) | KR1: Chinese-Korean, N = 201, Ref. (17) | KR2: Korea, N = 316, Ref. (18) |
| KR3: Korea, N = 301, Ref. (19) | JP1: Japan, N = 238, Ref. (20, 21) | PL1: Poland, N = 208, Ref. (22) | BY1: Belarus, N = 328, Ref. (23) |
| ES1: Spain, N = 768, Ref. (24) | ES2: Spain, N = 76, Ref. (25) | ES3: Spain, N = 134, Ref. (26) | ES4: Spain, N = 148, Ref. (27) |
| EU1: Europe (German, Dutch, Turkish), N = 391, Ref. (28) | NL1: Dutch & Belgian, N = 245, Ref. (29) | CZ1: Czech-Caucasian, N = 50, Ref. (30) | BR1: Brazil, N = 873, Ref. (31) |
| CA1: Central Africa, N = 101, (32) | MZ1: Mozambique, N = 112, Ref. (33) | ZA-E1 : South Africa-English, N = 101, Ref. (34) | ZA-I1 : South Africa-Indian, N = 77, Ref. (34) |
| ZA-X1: South Africa-Xhosa, N = 88, Ref. (34) | ZA-I2: South Africa-Indian, N = ?, Ref. (35) | ZA-E2: South Africa-English, N = ?, Ref. (35) | ZA-X1: South Africa-Xhosa, N = ?, Ref. (35) |
| ZA1: South Africa, N = 279, Ref. (36) | | | |

Mutation Rate. Inclusion of a selection of one or more highly mutating Y-STR markers is also considered. The individual mutation rates (MR) of Y-STR markers has been described in US Application Publication 2011/0263437 A1, and Ballantyne, et al, Forensic Sci Int. Genet. (2011), doi:10.1016/j.fsigen.2011.04.017). A rapidly mutating Y-STR marker may have a mutation rate greater than about $10^{-2}$. TABLE 1 shows the mutation rate for each of the Y-STR markers considered for inclusion in the multiplex panels.

FIG. 1 shows Y-STR markers mapped for Gene Diversity on the x axis vs. mutation rate on the y axis. Diamonds represent Y-STR marker loci presently in the commercially Yfiler® multiplex analysis kit. Triangles represent Y-STR markers not part of the Yfiler® kit. Y-STR markers to be considered for inclusion in the multiplex panel described here may be selected for a combination of gene diversity and mutation rate properties, amongst other characteristics.

In devising a Y-STR multiplex assay panel that is separated and detected using electrophoresis, multiplex design can take advantage of a number of differentiable fluorescent dye channels, and differing fragment size to place detection of each individual allele region for a marker at a selected portion of the electrophoretic run, permitting the detection of labeled amplicons for all of the multiplexed loci without overlapping signals. Available "space" within the multiplex, when incorporating all the Yfiler® markers, can result in severe constraint in adding additional Y-STR markers to the panel. This constraint may be reflected in primer design consideration. In another aspect, the primer design and placement may also need to provide for a separation of 1 or 2 base pairs between alleles of different Y-STR markers. In some embodiments, alleles of different Y-STR markers are separated by a 2 base pair "space" in the electrophoretic analysis, permitting more accurate allele and marker identification.

The use of mini-STRs, which produce amplicons of less than about 220 bp, also permit increased plexy while also permitting amplification and thus detection of degraded DNA. However, not every STR marker can be adapted for use as a mini-STR. If the repeat sequence plus necessary flanking bases add up to too many bases or if the flanking sequence doesn't allow for specific primer design, the STR marker may be unsuitable for mini-STR use. The Y-STR markers that are unsuitable as mini-STR markers are limited in placement within the assay panel to a region reserved for larger amplicon fragment detection. For example, some primers designed to place DYF404S1 and DYF387S1 at about 200 base pairs did not provide satisfactory results, and those markers may be more successfully placed in a multiplex panel at a larger amplicon size range.

Additional considerations when selecting Y-STR markers for inclusion within the multiplex panels described here are discussed further in the section describing primer design, and include evaluation for specificity (i.e., only the target nucleic acid is amplified); sensitivity (i.e., even a small amount of a target nucleic acid within a mixed forensic sample can be accurately amplified), and for potential undesirable interactions within the multiplex.

Some Y-STR markers may not yield the highest probability of successful incorporation into a multiplex assay panel, based upon initial studies. For example, 3 different primer pairs were tested for DYS626. Two of the primer pairs showed additional peaks in samples with 1:500 male/female DNA, while the third primer pair showed interactions with Yfiler® markers DYS392 and DYS439. In another example, two different primer pairs for DYF404S1 were tested. Both had only ⅓ of their original peak height when used in 1:500 male/female DNA samples. This may lead to a drop out problem in casework samples. In a third example, two different primers were tested for DYS547, but both displayed undesirable amplification of female DNA when tested in a 1:500 male:female mixture. All of these markers may be successfully used in multiplex panels if forensic samples including male:female mixtures were not used for source DNA. For instance, if the Y-STR multiplex panel is used to discriminate between male relatives, any of these markers may be successful additions to an improved Y-STR multiplex panel compared to currently commercially available kits.

Another complication may arise when evaluating markers such as DYS612, which due to the nature of its trinucleotide repeat, may provide amplified products which include significant percentages of stutter. Stutter is an artifact seen when amplifying short tandem repeats and may occur at one repeat unit shorter in length than the parent allele. In forensic analysis, stutter complicates the analysis of DNA profiles from multiple contributors, so a marker with pronounced tendency for stutter may not be as desirable for use in multiplex forensic panels used for samples having mixed sources, potentially at significantly varying ratios. It may be used successfully, however, in analysis for resolution of individual male identity/relatedness.

In some cases, the primers for the current Y-filer® markers may be altered to remove interactions with the newly added Y-STR markers of the various panels.

Several different multiplex panels are shown here, which include the current Y-filer® markers plus additional Y-STR markers to maximize haplotype resolution.

Figure 2:
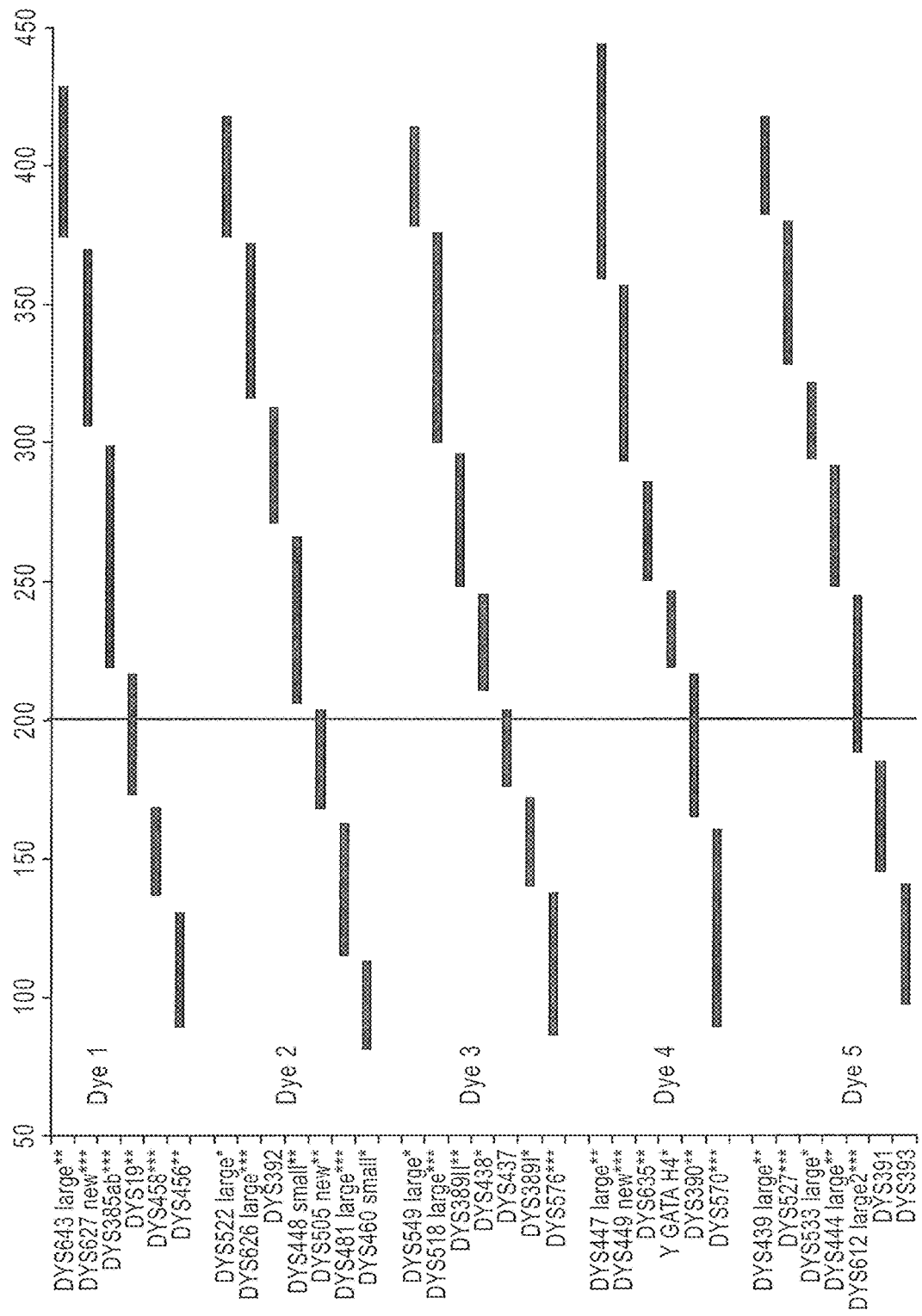
FIG. 2 is a schematic representation of one embodiment of a Y-STR multiplex assay panel, Panel 1.

FIG. 2 shows a schematic representation of Panel 1, a 35 plex Y-STR multiplex assay panel. Six dyes are used, including a size standard/allelic ladder labeled with a sixth differentiable fluorescent dye (not shown). Thirteen markers are mini-STRs and the entire panel is captured in an electrophoretic run of about 450 base pairs.

Figure 3:
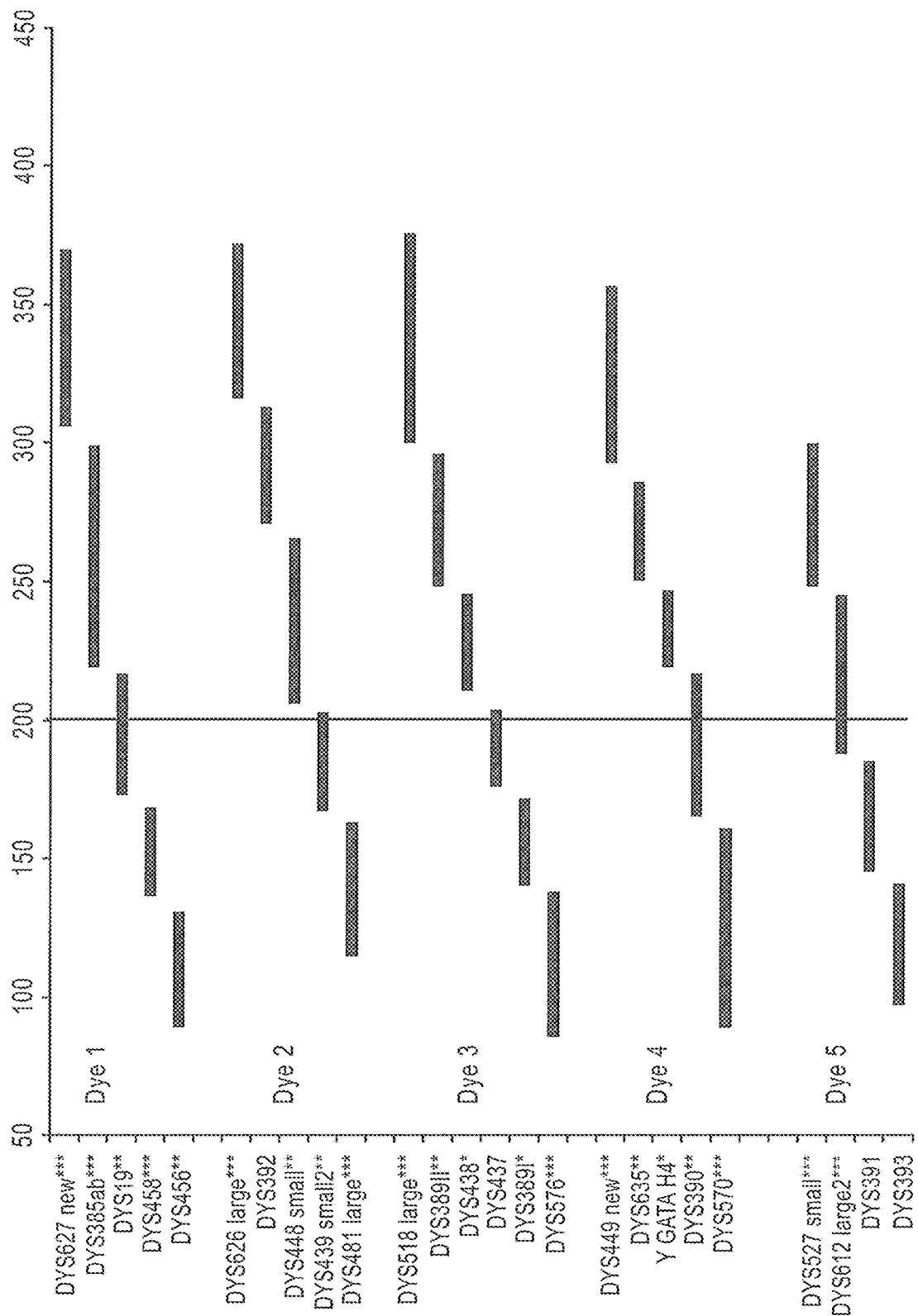
FIG. 3 is a schematic representation of an embodiment of a Y-STR multiplex assay panel, Panel 2.

FIG. 3 shows a schematic representation of Panel 2, a 27-plex Y-STR multiplex assay panel that includes all Yfiler® STR markers and 10 additional Y-STR markers (including a double copy marker) having a Gene Diversity value greater than 0.75, where the multiplex includes 7 rapidly mutating Y-STR markers. Six dyes are used, including a size standard/allelic ladder labeled with a sixth differentiable fluorescent dye (not shown). Twelve markers are mini Y-STR markers, and the entire panel is captured in an electrophoretic run of about 370 base pairs.

Figure 4:
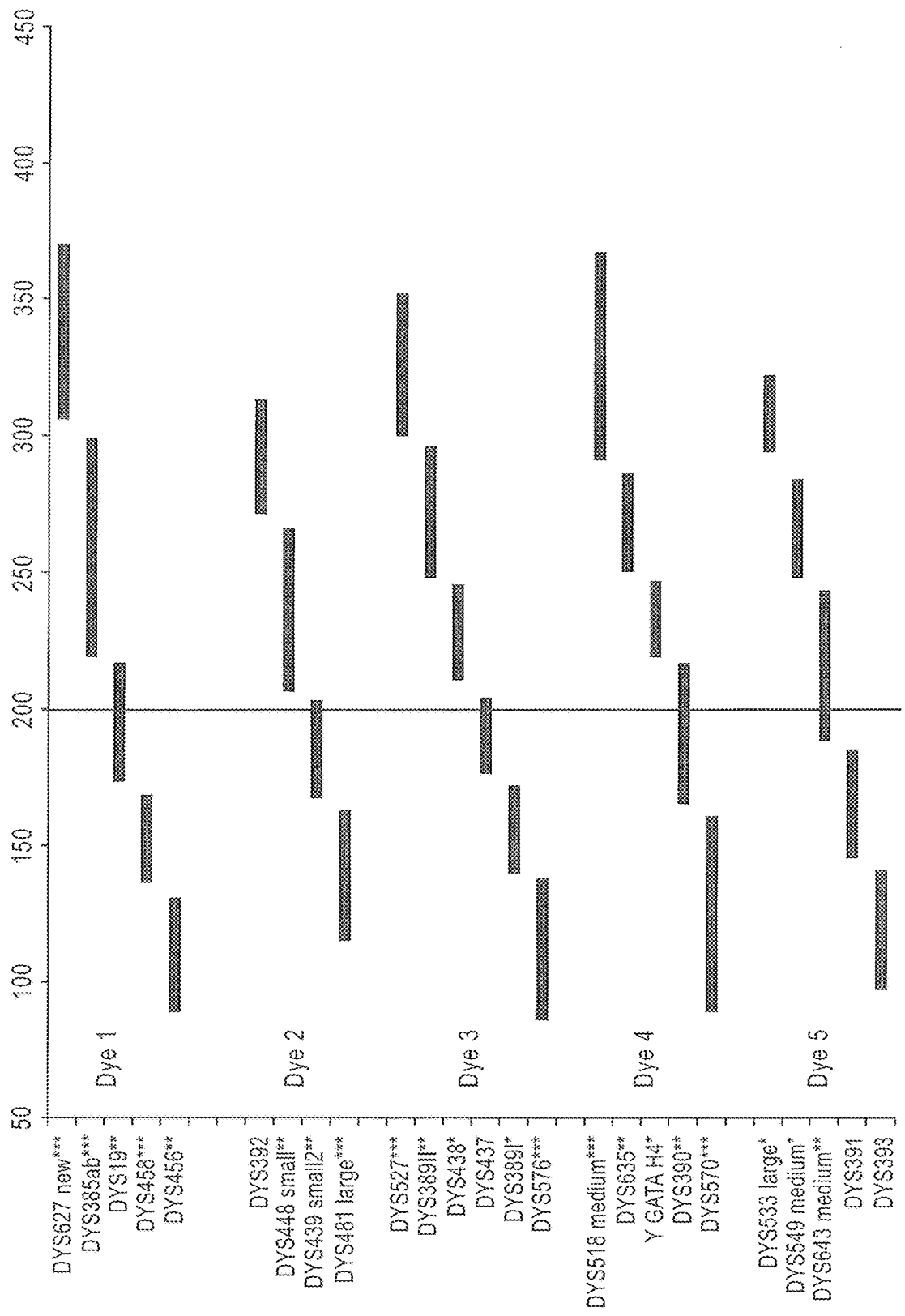
FIG. 4 is a schematic representation of another embodiment of a Y-STR multiplex assay panel, Panel 3.

FIG. 4 shows a schematic representation of Panel 3, a 30-plex Y-STR multiplex assay panel that includes all Yfiler® STR markers, and 9 additional (10, including the double marker) Y-STR markers having a Gene Diversity value greater than 0.75. Six dyes are used, including a size standard/allelic ladder labeled with a sixth differentiable fluorescent dye (not shown). Twelve markers are mini-STR markers, and the entire panel is captured in an electrophoretic run of about 420 base pairs.

Figure 5:
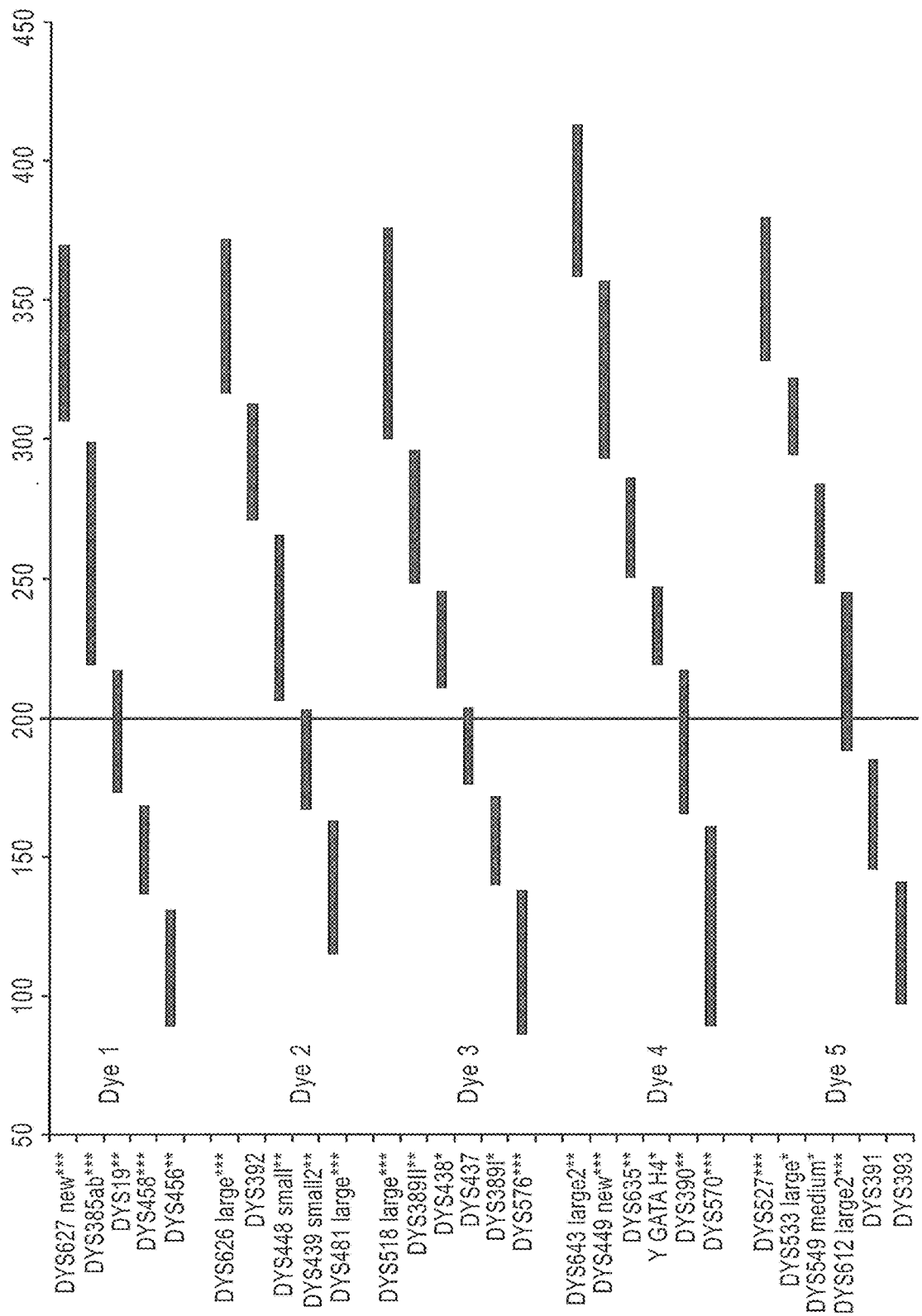
FIG. 5 is a schematic representation of a further embodiment of a Y-STR multiplex assay panel, Panel 4.

FIG. 5 shows a schematic representation of Panel 4, a 27-plex Y-STR multiplex containing all Yfiler® Y-STR markers, the three best markers based on average Gene Diversity value, and six additional markers. Six dyes are used, including a size standard/allelic ladder labeled with a sixth differentiable fluorescent dye (not shown). Twelve markers are mini-STR markers, and the entire panel is captured in an electrophoretic run of about 370 base pairs.

Figure 6:
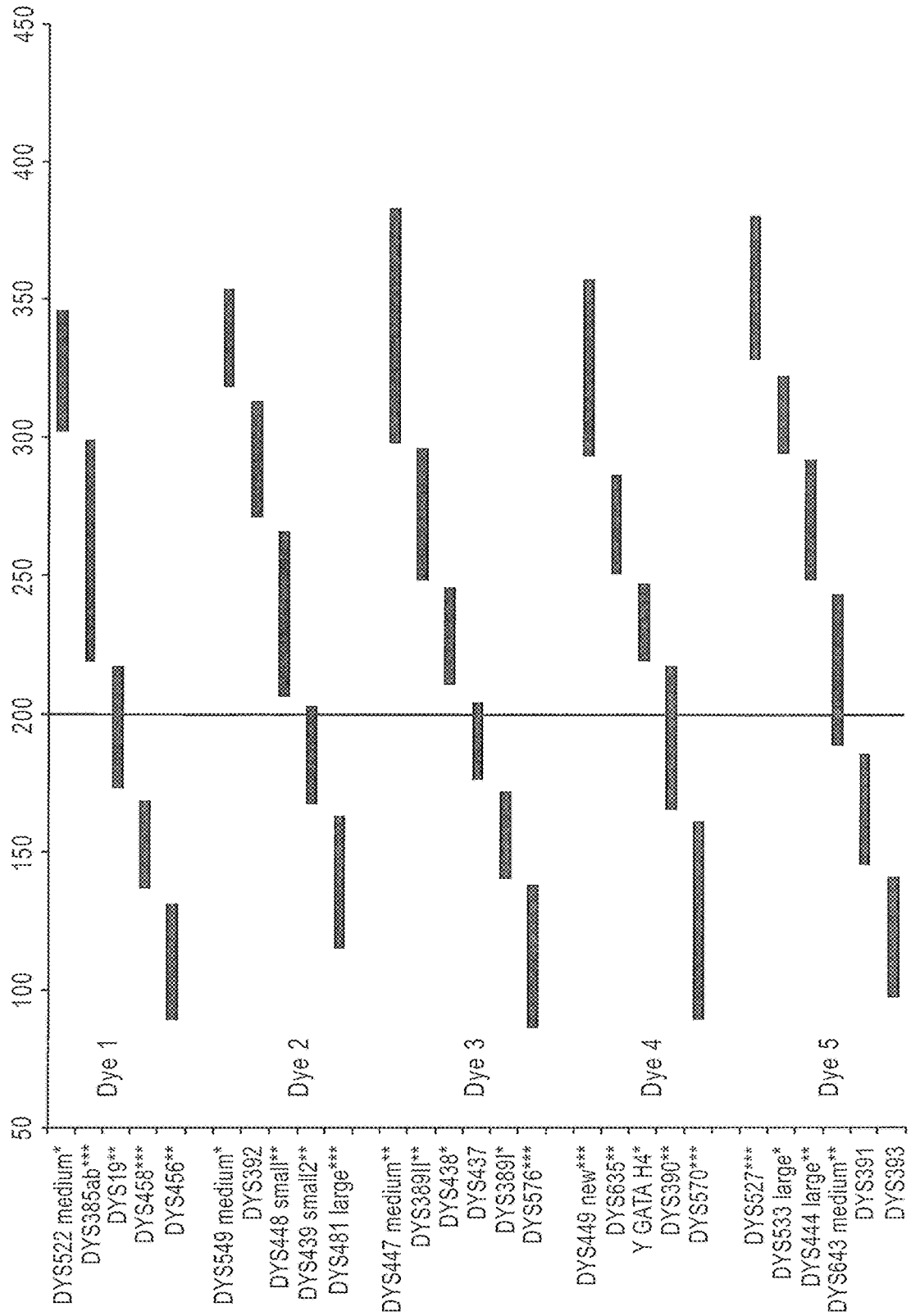
FIG. 6 is a schematic representation of yet another embodiment of a Y-STR multiplex assay panel, Panel 5.

FIG. 6 shows a schematic representation of Panel 5, a 27-plex Y-STR multiplex containing all Yfiler® Y-STR markers, and 12 other Y-STR markers. Six dyes are used, including a size standard/allelic ladder labeled with a sixth differentiable fluorescent dye (not shown). Twelve markers are mini-STR markers, and the entire panel is captured in an electrophoretic run of about 410 base pairs.

For the Y-STR multiplex assay panels of FIGS. 3-6, an additional marker, DYS460, which has a moderate Gene Diversity value, could be included in Dye 2 channel, to obtain a total of 13 mini-STR markers.

Figure 7:
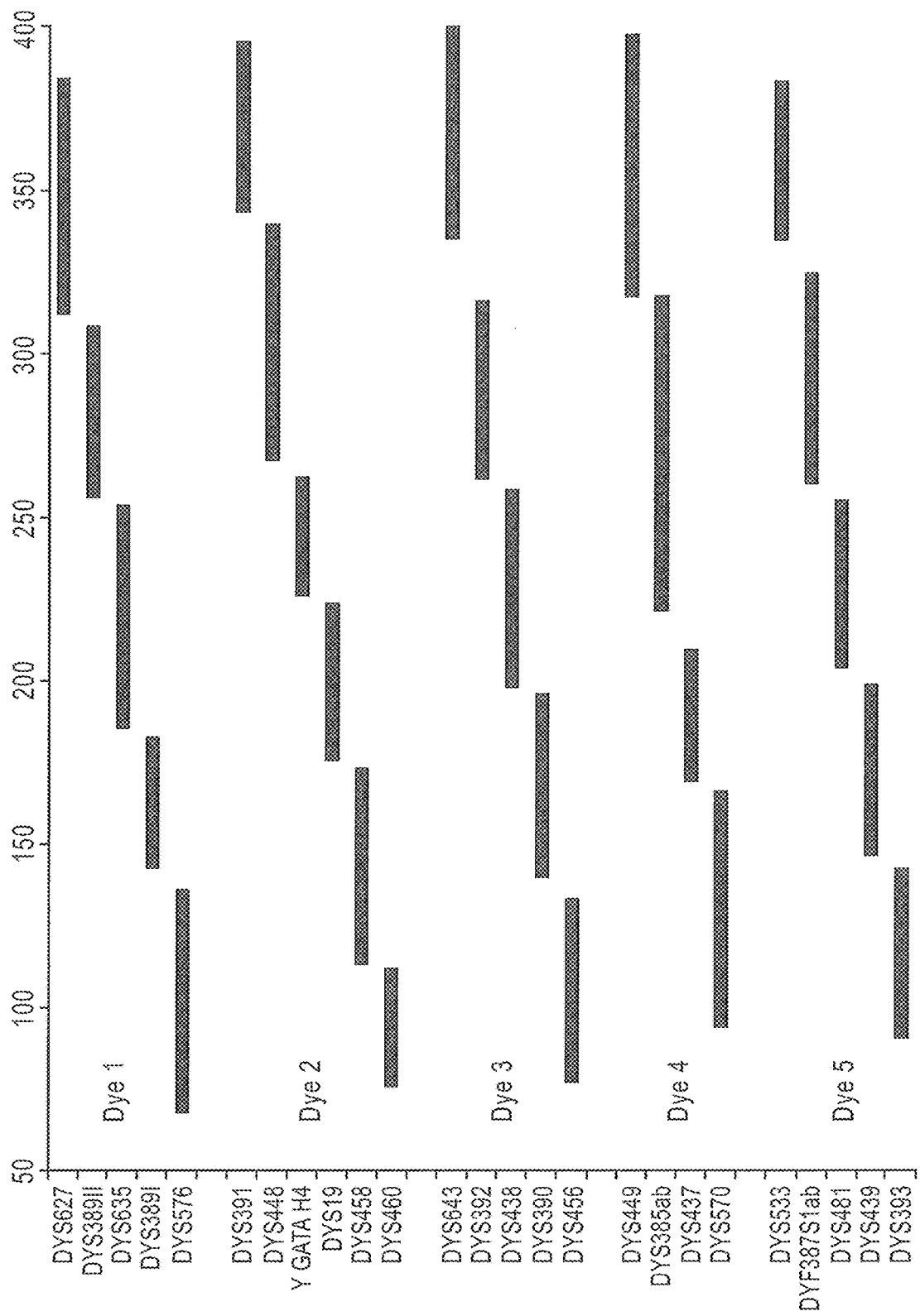
FIG. 7 is a schematic representation of yet another embodiment of a Y-STR multiplex assay panel, Panel 6.

FIG. 7 shows a schematic representation of Panel 6, a 27-plex Y-STR multiplex containing all Yfiler® Y-STR markers and ten additional markers. Two of the twenty seven markers are double copy markers (DYS385 ab and DYF387S1ab), and eleven markers are mini-markers of less than about 220 base pairs. The at least 11 Y-STR markers having a size of less than about 220 base pairs may be DYS576, DYS389I, DYS460, DYS458, DYS19, DYS456, DYS390, DYS570, DYS437, DYS393, and DYS439. Six dyes are used, including a size standard/allelic ladder labeled with a sixth differentiable fluorescent dye (not shown). At least five markers are rapidly mutating markers (see TABLE 1), and represent six total rapidly mutating markers in the panel because DYF387S1ab is a double copy marker. The rapidly mutating Y-STR markers may be DYF387S1ab, DYS449, DYS570, DYS576, and DYS627. DYS446 was not included in this panel because its proximity to the DYS393 marker (present in the Yfiler® multiplex) may cause artifacts from amplification through both markers. The entire panel is captured in a range of about 76-400 base pairs upon electrophoretic separation. FIG. 9 shows allele ranges for Panel 6 in comparison to database and other Y-STR panels.

Figure 8:
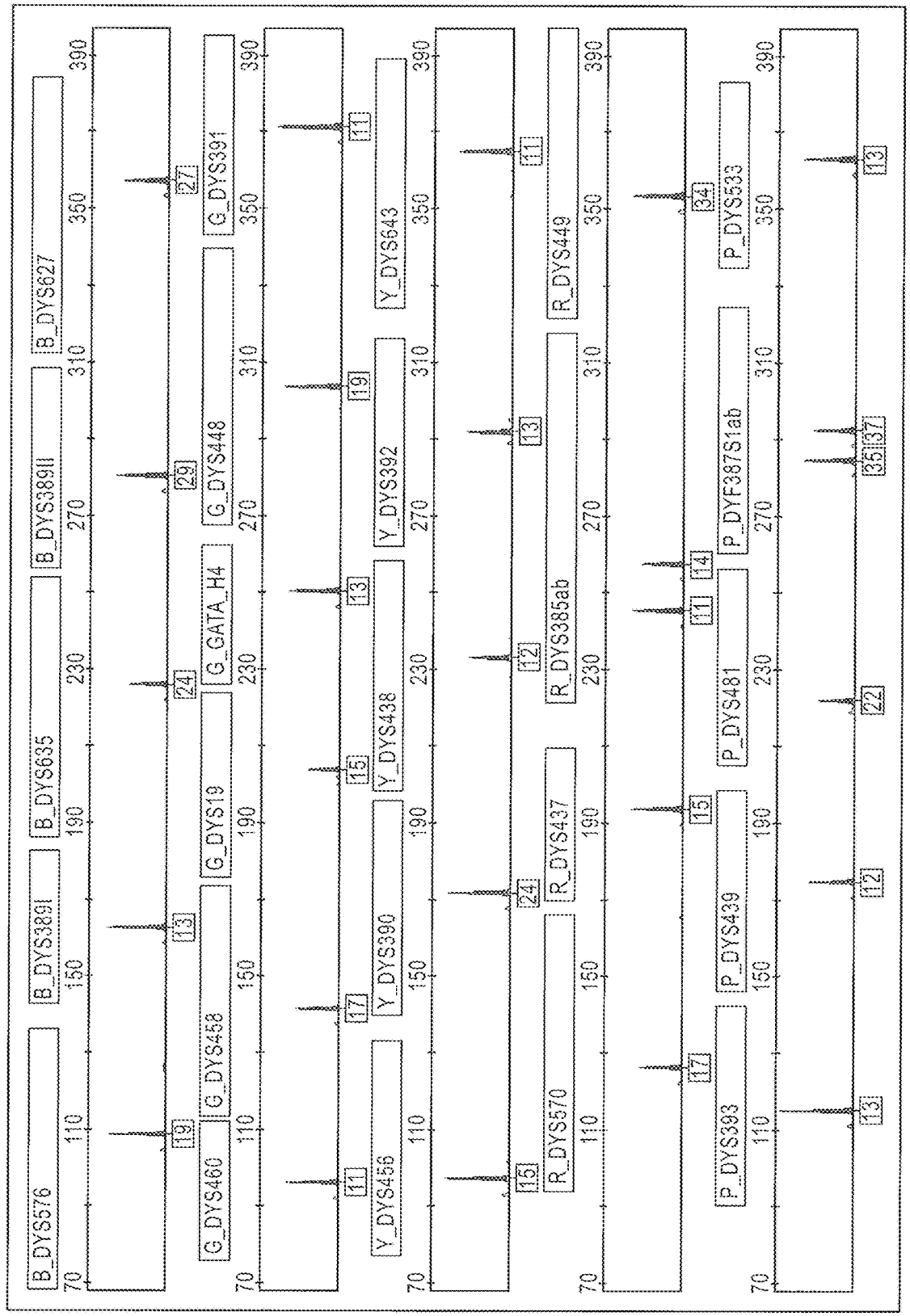
FIG. 8 is a graphical representation of an electrophoretic run for the Y-STR panel of FIG. 7 (Panel 6), color separated. The $6^{th}$ dye standard channel is not shown.

FIG. 8 shows a graphical representation of an electrophoretic separation using the 27-plex Y-STR marker panel of FIG. 7 (Panel 6), showing each differentiable dye channel in a separate lane and not showing the size standard dye channel using the sixth dye. In TABLE 2, entries 1-18 and 20-26 describe the individual markers, the repeat sequences, the repeat types, and the chromosomal location of the Y-STR markers of Panel 6. Panel 6 is a multiplex assay for the amplification of a set of primers for the amplification of DYF387S1ab, DYS19, DYS385ab, DYS389I, DYS389II, DYS390, DYS391, DYS392, DYS393, and DYS460, DYS437, DYS438, DYS439, DYS448, DYS449, DYS456, DYS458, DYS481, DYS533, DYS570, DYS576, DYS627, DYS635, DYS643, and Y-GATA-H4.

Figure 10:
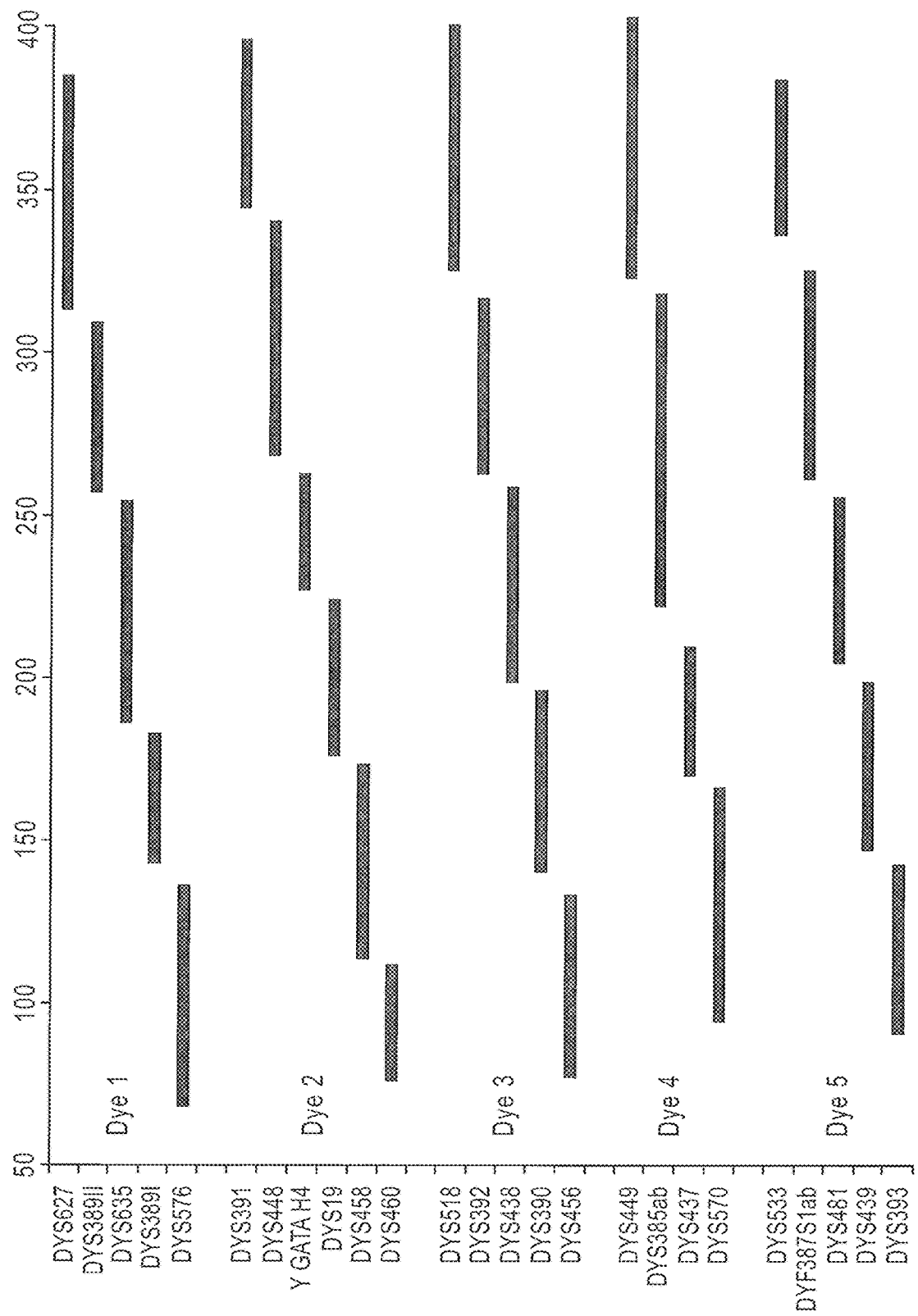
FIG. 10 is a schematic representation of another embodiment of a Y-STR multiplex assay panel, Panel 7.

FIG. 10 shows a schematic representation of Panel 7, a 27-plex Y-STR multiplex containing all Yfiler® Y-STR markers and ten additional markers. Two of the twenty seven markers are double copy markers (DYS385ab and DYF387S1ab), and eleven markers are mini-markers of less than about 220 base pairs. The at least 11 Y-STR markers having a size of less than about 220 base pairs may be DYS576, DYS389I, DYS460, DYS458, DYS19, DYS456, DYS390, DYS570, DYS437, DYS393, and DYS439. Six dyes are used, including a size standard/allelic ladder labeled with a sixth differentiable fluorescent dye (not shown). At least five markers are rapidly mutating markers (see Table 1), and represent a total of seven rapidly mutating markers in the panel because DYF387S1ab is a double copy marker. The rapidly mutating Y-STR markers may be DYF387S1ab, DYS449, DYS518, DYS570, DYS576, and DYS627. The entire panel may be captured in a range of about 68 to about 406 base pairs upon electrophoretic separation. FIG. 12 shows allele ranges for Panel 7 in comparison to database and other Y-STR panels.

Figure 11:
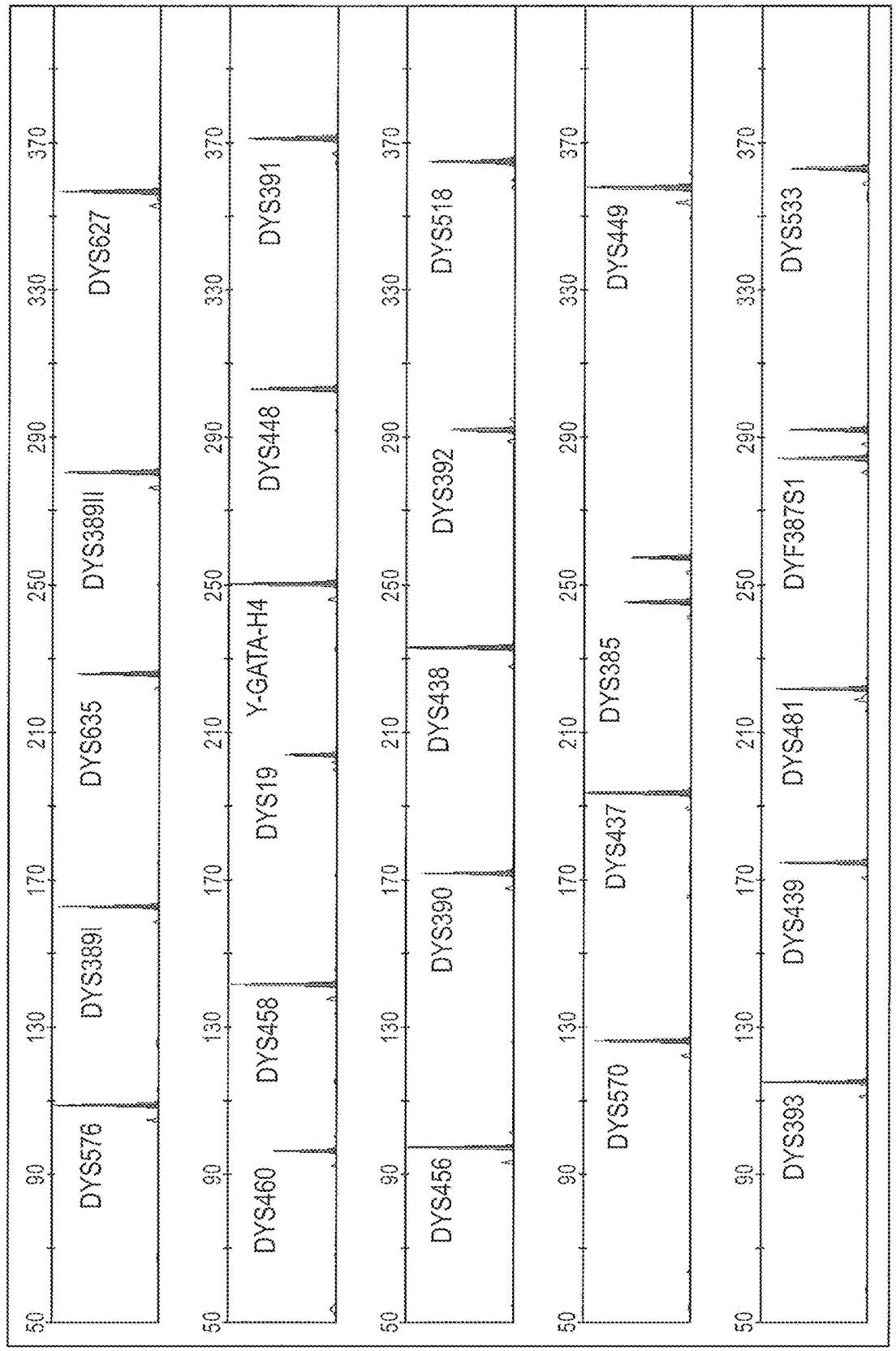
FIG. 11 is a graphical representation of an electrophoretic run for the Y-STR panel of FIG. 10 (Panel 7), color separated. The $6^{th}$ dye standard channel is not shown

FIG. 11 shows a graphical representation of an electrophoretic separation using the 27-plex Y-STR marker panel of FIG. 10 (Panel 7), showing each differentiable dye channel in a separate lane and not showing the size standard dye channel using the sixth dye. In TABLE 2, entries 1-24 and 26 describe the individual markers, the repeat sequences, the repeat types, and the chromosomal location of the Y-STR markers of Panel 7. Panel 7 is a multiplex assay for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4.

TABLE 2

Y-STR markers, including repeat sequence, type, and chromosomal location.

| | Marker | Repeat Sequence | Repeat type | Chr. Location | Notes |
|---|---|---|---|---|---|
| 1 | DYF387S1ab | [AAAG]3[GTAG]1[GAAG]4-[AAAG]2[GAAG]1-[AAAG]2[GAAG]m[AAAG]n (SEQ ID NO: 8) | 4 | Yq12 Yq11.23 | a. |
| 2 | DYS19 | [TAGA]3TAGG[TAGA]n (SEQ ID NO: 9) | 4 | Yp11.2 | |
| 3 | DYS385ab | [GAAA]n | 4 | Yq11.222 | |
| 4 | DYS389I | [TCTG]3[TCTA]n (SEQ ID NO: 10) | 4 | Yq11.221 | |
| 5 | DYS389II | [TCTG]m[TCTA]o-[TCTG]3[TCTA]n (SEQ ID NO: 11) | 4 | Yq11.221 | |
| 6 | DYS390 | [TCTG]8[TCTA]n--[TCTG]1[TCTA]4 (SEQ ID NO: 12) | 4 | Yq11.221 | |
| 7 | DYS391 | [TCTA]n | 4 | Yq11.21 | |
| 8 | DYS392 | [TAT]n | 3 | Yq11.223 | |
| 9 | DYS393 | [AGAT]n | 4 | Yq12 | |
| 10 | DYS437 | [TCTA]n[TCTG]2[TCTA]4 (SEQ ID NO: 13) | 4 | Yq11.221 | |
| 11 | DYS438 | [TTTTC]n | 5 | Yq11.221 | |
| 12 | DYS439 | [GATA]n | 4 | Yq11.221 | |
| 13 | DYS448 | [AGAGAT]nN42-[AGAGAT]m (SEQ ID NO: 14) | 6 | Yq11.223 | |
| 14 | DYS449 | [TTCT]nN22[TTCT]3--N12[TTCT]m (SEQ ID NO: 15) | 4 | Yp11.2 | b. |
| 15 | DYS456 | [AGAT]n | 4 | Yp11.2 | |
| 16 | DYS458 | [GAAA]n | 4 | Yp11.2 | |
| 17 | DYS460 | [ATAG]n | 4 | Yq11.222 | b. |
| 18 | DYS481 | [CTT]n | 3 | Yp11.2 | b. |
| 19 | DYS518 | [AAAG]3[GAAG]1[AAAG]n-[GGAG]1-[AAAG]4N6[AAAG]m-N27[AAGG]4 (SEQ ID NO: 16) | 4 | Yq11.221 | b. |
| 20 | DYS533 | [ATCT]n | 4 | Yq11.221 | b. |
| 21 | DYS570 | [TTTC]n | 4 | Yp11.2 | b. |
| 22 | DYS576 | [AAAG]n | 4 | Yp11.2 | b. |
| 23 | DYS627 | [AGAA]3N16[AGAG]3-[AAAG]n*N82*[AAGG]3 (SEQ ID NO: 17) | 4 | Yp11.2 | c. |
| 24 | DYS635 | [TCTA]4[TGTA]2-[TCTA]2[TGTA]2-[TCTA]2[TGTA]0,2[TCTA]n | 4 | Yq11.221 | |
| 25 | DYS643 | [CTTTT]n (SEQ ID NO: 18) | 5 | Yq11.221 | b. |

TABLE 2-continued

Y-STR markers, including repeat sequence, type, and chromosomal location.

| | Marker | Repeat Sequence | Repeat type | Chr. Location | Notes |
|---|---|---|---|---|---|
| 26 | GATA-H4 | [TAGA]nN12[GAT*C*]2-AA[TAGA]4 (SEQ ID NO: 19) | 4 | Yq11.221 | d. |
| ii | DYS549 | [GATA]n | 4 | Yq11.223 | b. |

TABLE LEGEND:
variable repeats in BOLD, Different Sequence listed in Italics and underlined.
a. Sequence Repeat confirmed through in-house sequencing. Ballantyne et al. 2011 published different repeat structure: AAAG]3[GTAG][GAAG]4N16-[GAAG]9[AAAG]n, and different chromosomal location: Yq11.2 Yq11.23.
b. Sequence Repeat confirmed through in-house sequencing.
c. Sequence Repeat confirmed through in-house sequencing. Ballantyne et al. 2011 published different repeat structure: AGAA]3N16[AGAG]3[AAAG]n*N81*[AAGG]3
d. Sequence differs in NCBI RefSeq NC000024 from STRbase: [TAGA]12N12[GAT*G*]2AA[TAGA)4.

Figure 13:
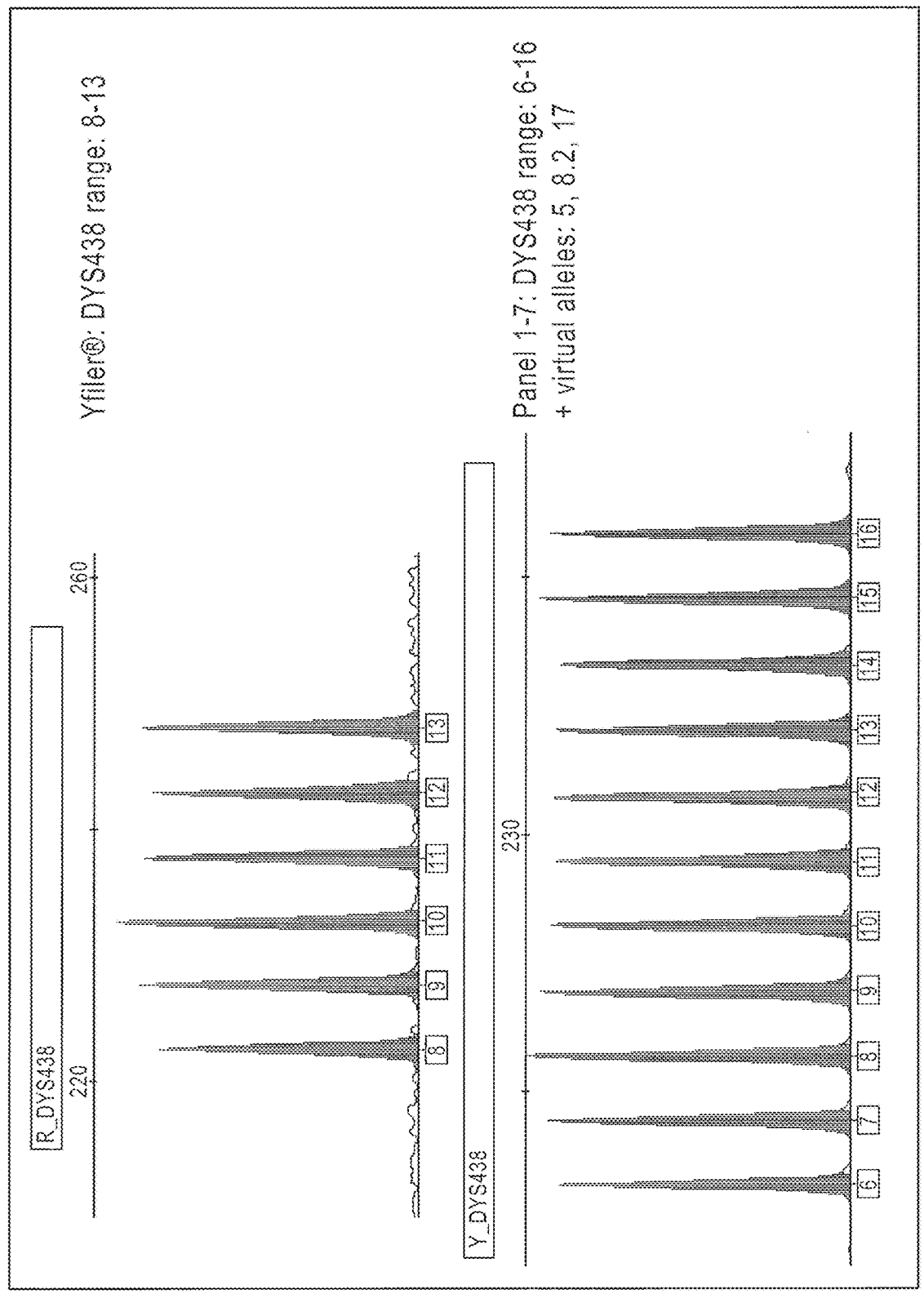
FIG. 13 is a graphical representation comparing the alleles of the Yfiler® multiplex assay and the expanded alleles of Panels 1-7 for DYS438 marker.

Alleles. Numerous new alleles have been reported, and may be incorporated into the Y-STR marker analysis. FIG. 9 shows the alleles for each marker for Panel 6, in comparison to other panels. FIG. 12 shows the alleles for each marker of Panel 7. Both panels contain expanded allele ranges for selected markers. The allelic ladder for Panels 6 and 7 incorporate these new alleles. For example the expanded allele ranges are shown in FIG. 13 for marker DYS438. The upper lane shows the alleles from the Yfiler® kit (8-13 for a total of 6) while the lower lane shows the expanded 6-16 repeat range for the Y-STR Panels 1-7, which also includes virtual alleles 5, 8.2 (identified in the schematic as 8), and 17.

Primer design. Once a set of loci for co-amplification in a single multiplex reaction is identified, one can determine primers suitable for co-amplifying each locus in the set. Oligonucleotide primers may be added to the reaction mix and serve to demarcate the 5' and 3' ends of an amplified DNA fragment. One oligonucleotide primer anneals to the sense (+) strand of the denatured template DNA, and the other oligonucleotide primer anneals to the antisense (-) strand of the denatured template DNA. Typically, oligonucleotide primers may be approximately 12-25 nucleotides in length, but their size may vary considerably depending on such parameters as, for example, the base composition of the template sequence to be amplified, amplification reaction conditions, etc. Oligonucleotide primers can be designed to anneal to specific portions of DNA that flank a locus of interest, to specifically amplify the portion of DNA between the primer-complementary sites. The length of the primer may need to be modified in order to be more specific and prevent amplification of non-target nucleic acid. For example, it was discovered that lengthening the primer for DYS456 marker resolved a problem with unwanted amplification of female DNA for a subset of female DNA samples when amplifying a mixed male:female sample. On the left hand side of FIG. 14, two partial electrophoretic separation segments showing the DYS456 marker demonstrate inappropriate amplification of female DNA (off-scale peak at left side of the separation segment) when the select female A and female B samples were present in a 0.5 ng male/250 ng female sample and using standard length (25 nucleotides or less) primers. In contrast, using lengthened primers (28 nucleotides long) to amplify DYS456, when analyzing these two problematic male/female mixtures, as shown in the right hand panels of FIG. 14, appropriately amplified male alleles are seen for this Y-STR marker (on-scale solo peak with no evidence of inappropriate female DNA amplification).

Oligonucleotide primers may include adenosine, thymidine, guanosine, and cytidine, as well as uracil, nucleoside analogs (for example, but not limited to, inosine, locked nucleic acids (LNA), non-nucleotide linkers, peptide nucleic acids (PNA) and phosporamidites) and nucleosides containing or conjugated to chemical moieties such as radionuclides (e.g., $^{32}P$ and $^{31}S$), fluorescent molecules, minor groove binders (MGBs), or any other nucleoside conjugates known in the art.

Generally, oligonucleotide primers can be chemically synthesized. Care should be taken in selecting the primer sequences used in the multiplex reaction. Inappropriate selection of primers may produce undesirable effects such as a lack of amplification, amplification at one site or multiple sites besides the intended target locus, primer-dimer formation, undesirable interactions between primers for different loci, production of amplicons from alleles of one locus which overlap (e.g., in size) with alleles from another locus, or the need for amplification conditions or protocols particularly suited for each of the different loci, which conditions/protocols are incompatible in a single multiplex system. Primers can be developed and selected for use in the multiplex systems of this teaching by, for example, employing a re-iterative process of multiplex optimization that is well familiar to one of ordinary skill in the art: selecting primer sequences, mixing the primers for co-amplification of the selected loci, co-amplifying the loci, then separating and detecting the amplified products to determine effectiveness of the primers in amplification.

Primers can be selected by the use of any of various software programs available and known in the art for developing amplification and/or multiplex systems. See, e.g., Primer Express® software (Applied Biosystems, Foster City, Calif.). In the example of the use of software programs, sequence information from the region of the locus of interest can be imported into the software. The software then uses various algorithms to select primers that best meet the user's specifications.

Initially, this primer selection process may produce any of the undesirable effects in amplification described above, or an imbalance of amplification product, with greater product yield for some loci than for others because of greater binding strength between some primers and their respective targets than other primers, for example resulting in preferred annealing and amplification for some loci. Or, the primers may generate amplification products which do not represent the target loci alleles themselves; i.e., non-specific amplification product may be generated. These extraneous products resulting from poor primer design may be due, for example, to annealing of the primer with non-target regions of sample DNA, or even with other primers, followed by amplification subsequent to annealing.

When imbalanced or non-specific amplification products are present in the multiplex systems during primer selection, individual primers can be taken from the total multiplex set and used in amplification with primers from the same or other loci to identify which primers contribute to the amplification imbalance or artifacts. Once two primers which generate one or more of the artifacts or imbalance are identified, one or both contributors can be modified and retested, either alone in a pair, or in the multiplex system (or a subset of the multiplex system). This process may be repeated until product evaluation results in amplified alleles with no amplification artifacts or an acceptable level of amplification artifacts in the multiplex system.

The optimization of primer concentration can be performed either before or after determination of the final primer sequences, but most often may be performed after primer selection. Generally, increasing the concentration of primers for any particular locus increases the amount of product generated for that locus. However, primer concentration optimization is also a re-iterative process because, for example, increasing product yield from one locus may decrease the yield from another locus or other loci. Furthermore, primers may interact with each other, which may directly affect the yield of amplification product from various loci. In sum, a linear increase in concentration of a specific primer set may not necessarily equate with a linear increase in amplification product yield for the corresponding locus. Reference is made to Simons, U.S. Pat. No. 5,192,659, for a more detailed description of locus-specific primers, the teaching of which is incorporated herein by reference in its entirety.

Locus-to-locus amplification product balance in a multiplex reaction may also be affected by a number of parameters of the amplification protocol, such as, for example, the amount of template (sample DNA) input, the number of amplification cycles used, the annealing temperature of the thermal cycling protocol, and the inclusion or exclusion of an extra extension step at the end of the cycling process. An absolutely even balance in amplification product yield across all alleles and loci, although theoretically desirable, is generally not achieved in practice.

Mobility Modifiers. In some embodiments the electrophoretic mobility of the amplification product, i.e., amplicon containing the STR for a given locus, can be adjusted to avoid overlapping with the electrophoretic mobility range of another, different STR locus amplicon. This can be done in at least two different approaches that may be used in isolation or in combination with one another. In one approach, the position of the primers is adjusted to create either a smaller or larger amplification product to avoid overlapping the molecular weight size of another locus during electrophoresis. In another approach, mobility modifier moieties including, but not limited to, for example, polyethyleneoxide repeat subunits optionally interrupted by phosphodiester or phosphotriester subunits may be incorporated as a non-nucleotide linker between a fluorescent dye at the 5'-end of the primer and the primer sequence. The polyethyleneoxide repeat subunits may be triethyleneoxide, tetraethyleneoxide, pentaethyleneoxide, hexaethyleneoxide (HEO), heptaethyleneoxide, or octaethyleneoxide subunits.

The polyethylene repeat subunit may be repeated once, twice, three, four, five, six, seven, eight, nine, ten, eleven or twelve times. The mobility modifier moiety may be attached to the 5'-end of the primer sequence via a phosphodiester moiety. See, for example, U.S. Pat. Nos. 5,470,705; 5,514,543; 5,580,732; 5,624,800; 5,703,222; 5,777,096; 5,807,682; 5,989,871; 6,395,486; 6,734,296; 6,756,204; 6,743,905; 7,074,569; 7,115,376; 7,129,050; and 7,897,338, each of which is incorporated by reference herein in its entirety. Similarly, the amplification primers may contain additional nucleotides (at the 5' end) that do not hybridize to the locus, but are added to create the desired mobility of the amplicon for the detection method employed, e.g., electrophoresis or mass spectroscopy. The resulting PCR amplification product (of the larger of the two PCR products) contains the mobility modifier molecules, increasing the molecular weight of the PCR product and thus a perceived shift in the molecular weight of the larger PCR product to an even larger size. The molecular weight range, which is correlated to the size of an amplicon, therefore is apparently higher when the amplicon includes a mobility modifier moiety.

When amplicons of a Y-STR marker have a base pair size of less than about 220 base pairs, it may be referred to herein as a mini-Y-STR marker. In some embodiments, each of the amplicons of at least 11 Y-STR markers has a base pair size of less than about 220 base pairs. In some embodiments, each of the amplicons of at least one of at least 11 Y-STR markers having an effective base pair size of less than about 220 base pairs also includes a mobility modifier moiety. When the size for each of the amplicons of the mini Y-STR markers is stated to be less than about 220 base pairs, then the size range of less than about 220 base pairs includes 80-90% of the alleles for the mini Y-STR marker. In some embodiments, the at least 11 mini Y-STR markers may include DYS576, DYS389I, DYS460, DYS458, DYS19, DYS456, DYS390, DYS570, DYS437, DYS393, and DYS439. In other embodiments, the at least 11 mini Y-STR markers may include DYS19, DYS458, DYS456, DYS505, DYS481, DYS460, DYS437, DYS389I, DYS576, DYS390, DYS570, DYS391, and DYS393. In yet other embodiments, the at least 11 mini Y-STR markers may include DYS19, DYS458, DYS456, DYS439, DYS481, DYS437, DYS389I, DYS576, DYS390, DYS570, DYS391, and DYS393. In some other embodiments, at least 11 mini Y-STR markers may include DYS19, DYS458, DYS456, DYS439, DYS481, DYS437, DYS389I, DYS576, DYS390, DYS570, DYS391, and DYS393. In some embodiments, the at least 11 mini Y-STR markers are selected from DYS576, DYS389I, DYS460, DYS458, DYS19, DYS456, DYS390, DYS570, DYS437, DYS393, DYS439, DYS505, DYS481, and DYS391. In some embodiments, more than 11 mini-STR markers are selected from DYS576, DYS389I, DYS460, DYS458, DYS19, DYS456, DYS390, DYS570, DYS437, DYS393, DYS439, DYS505, DYS481, and DYS391. In some embodiments, the amplification primer for more than one Y-STR marker has a mobility modifier moiety incorporated therein. When the amplification primers for more than one Y-STR marker have mobility modifier moieties, then the structure of the mobility modifier moiety of the amplification primer for each different Y-STR marker may be selected independently. In some embodiments, more than 5, 6, 7, 8, 9, 10, 11, 12, 13, 14, or 15 Y-STR markers have mobility modified amplification primers. In some embodiments, mobility modified amplification primers may be selected for amplifying Y-STR markers from the group including DYS627, DYS389II, DYS635, DYS389I, DYS391, DYS448, Y-GATA-H4, DYS19, DYS438, DYS390, and DYS449, in any combination or subcombination.

In some embodiments, a set of amplification primers including primers for the amplification of at least 11 Y-STR markers is provided where the primers are configured to provide each set of amplicons of the at least 11 Y-STR markers having a base pair size less than about 220 base pairs. In some embodiments, detection of amplicon base pair size may be performed by a fluorescence detection technique. In some embodiments, detection of amplicon base pair size may be performed by a mobility-dependent analytical technique. The mobility-dependent analytical technique may be capillary electrophoresis. In some other embodiments, detection of the amplicon base pair size may be performed by a sequencing technique using no fluorescent dye labels. In some embodiments, the set of amplification primers may further include primers for the amplification of at least 5 additional Y-STR markers where the primers are configured to provide each set of amplicons of the at least 5 additional Y-STR markers having a base pair size greater than about 220 base pairs. In various embodiments, when the set of amplification primers amplify more than 11 Y-STR markers, then the set of amplification primers may be configured to provide all of the sets of amplicons of the more than 11 Y-STR markers having a base pair size less than about 410 base pairs. In various embodiments, when the set of amplification primers amplify more than 11 Y-STR markers, then the set of amplification primers may be configured to provide all of the sets of amplicons of the more than 11 Y-STR markers having a base pair size less than about 420 base pairs. The amplification primer set may include 25 Y-STR markers. In some embodiments, the set of amplification primers is labeled with one of at least 5 fluorescent dyes. In some embodiments, the set of amplification primers may be configured to provide each set of the amplicons of the at least 11 Y-STR markers labeled with one of at least 5 fluorescent dyes. The at least 5 fluorescent dyes used to label the primers and/or the amplicons may be configured to be spectrally distinct. The set of amplification primers may further include at least one amplification primer that includes a mobility modifier. The set of amplification primers for the amplification of at least 11 Y-STR markers may be configured to provide at least one set of amplicons of the Y-STR markers including a mobility modifier. In some embodiments, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the set of amplification primers amplifying the at least 11 Y-STR markers configured to provide each set of amplicons of the at least 11 Y-STR markers having a base pair size less than about 220 base pairs, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments, the set of primers for the amplification of at least 1I Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4.

In some embodiments, when primers for the amplification of more than the 11 Y-STR markers are provided, then the primers are configured to provide sets of amplicons of the more than 11 Y-STR markers having a base pair size less than about 400 base pairs. In some embodiments, when primers for the amplification of more than the 11 Y-STR markers are provided, then the primers are configured to provide sets of amplicons of the more than 11 Y-STR markers having a base pair size less than about 405 base pairs. In some embodiments, when primers for the amplification of more than the 11 Y-STR markers are provided, then the primers are configured to provide sets of amplicons of the more than 11 Y-STR markers having a base pair size less than about 410 base pairs. In some embodiments, when primers for the amplification of more than the 11 Y-STR markers are provided, then the primers are configured to provide sets of amplicons of the more than 11 Y-STR markers having a base pair size less than about 415 base pairs. In some embodiments, when primers for the amplification of more than the 11 Y-STR markers are provided, then the primers are configured to provide sets of amplicons of the more than 11 Y-STR markers having a base pair size less than about 420 base pairs. In some embodiments, when primers for the amplification of more than the 11 Y-STR markers are provided, then the primers are configured to provide all sets of amplicons of the more than 11 Y-STR markers having a base pair size less than about 405 base pairs. In some embodiments, when primers for the amplification of more than the 11 Y-STR markers are provided, then the primers are configured to provide all sets of amplicons of the more than 11 Y-STR markers having a base pair size less than about 410 base pairs. In some embodiments, when primers for the amplification of more than the 11 Y-STR markers are provided, then the primers are configured to provide all sets of amplicons of the more than 11 Y-STR markers having a base pair size less than about 415 base pairs. In some embodiments, when primers for the amplification of more than the 11 Y-STR markers are provided, then the primers are configured to provide all sets of amplicons of the more than 11 Y-STR markers having a base pair size less than about 425 base pairs.

In some embodiments, primers for the amplification of more than the 11 Y-STR markers are provided wherein each of the amplicons of at least 11 Y-STR markers has a base pair size of less than about 220 base pairs, and wherein the primers are configured to provide all sets of amplicons of the more than 11 Y-STR markers having a base pair size less than about 400 base pairs. In some embodiments, primers for the amplification of more than the 11 Y-STR markers are provided wherein each of the amplicons of at least 11 Y-STR markers has a base pair size of less than about 220 base pairs, and wherein the primers are configured to provide all sets of amplicons of the more than 11 Y-STR markers having a base pair size less than about 410 base pairs. In some embodiments, primers for the amplification of more than the 11 Y-STR markers are provided wherein each of the amplicons of at least 11 Y-STR markers has a base pair size of less than about 220 base pairs, and wherein the primers are configured to provide all sets of amplicons of the more than 11 Y-STR markers having a base pair size less than about 415 base pairs. In some embodiments, primers for the amplification of more than the 11 Y-STR markers are provided wherein each of the amplicons of at least 11 Y-STR markers has a base pair size of less than about 220 base pairs, and wherein the primers are configured to provide all sets of amplicons of the more than 11 Y-STR markers having a base pair size less than about 420 base pairs.

In yet another aspect, a set of amplification primers including primers for the amplification of at least 22 Y-STR markers is provided, where at least 5 of the Y-STR markers are rapidly mutating loci. In some embodiments, the at least 5 rapidly mutating Y-STR markers include DYF387S1ab, DYS449, DYS570, DYS576, and DYS627. In some embodiments, the at least 5 rapidly mutating Y-STR markers include DYS518. In various embodiments, the set of amplification primers configured to amplify the at least 22 Y-STR markers may be further configured to provide each set of amplicons of at least 11 Y-STR markers having a base pair size less than about 220 base pairs. In other embodiments, the set of amplification primers for the amplification of at least 22 Y-STR markers may be configured to provide sets of amplicons for the at least 22 Y-STR markers each having a base pair size of less than about 410 base pairs. In other embodiments, the set of amplification primers for the amplification of at least 22 Y-STR markers may be configured to provide sets of amplicons for the at least 22 Y-STR markers each having a base pair size of less than about 420 base pairs. In some embodiments, detection of amplicon base pair size may be performed by fluorescence detection. In some embodiments, detection of amplicon base pair size may be performed by a mobility-dependent analytical technique. The mobility-dependent analytical technique may be capillary electrophoresis. In some other embodiments, detection of the amplicon base pair size may be performed by a sequencing technique using no detection of fluorescent dye labels. The amplification primer set may include 25 Y-STR markers. In some embodiments, the set of amplification primers is labeled with one of at least 5 fluorescent dyes. In some embodiments, each set of the amplicons of the at least 22 Y-STR markers is labeled with one of at least 5 fluorescent dyes. The at least 5 fluorescent dyes used to label the primers and/or the amplicons may be configured to be spectrally distinct. The set of amplification primers may further include at least one amplification primer that includes a mobility modifier. The set of amplification primers for the amplification of at least 22 Y-STR markers may be configured to provide at least one set of amplicons of the Y-STR markers where the at least one set of amplicons includes a mobility modifier. In some embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS570, DYS576, DYS627, DYS635, and Y-GATA-H4. In other embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS518, DYS570, DYS576, DYS627, DYS635, and Y-GATA-H4.

Fluorophore labeling. In some embodiments of the present teaching, a fluorophore can be used to label at least one primer of the multiplex amplification, e.g. by being covalently bound to the primer, thus creating a fluorescent labeled primer. In some embodiments, primers for different target loci in a multiplex can be labeled with different fluorophores, each fluorophore producing a different colored product depending on the emission wavelength of the fluorophore. These variously labeled primers can be used in the same multiplex reaction, and their respective amplification products subsequently analyzed together. Either the forward or reverse primer of the pair that amplifies a specific locus can be labeled, although the forward may more often be labeled. In some embodiments, the 5' end of the forward primer may be labeled with a fluorophore. When the primer is labeled at the 5' end, it may be fluorescently labeled through a linker to the 5' phosphate. In other embodiments, when is labeled at the 5' end, it may be fluorescently labeled via a linker to the nucleobase.

The following are some examples of fluorophores well known in the art and suitable for use in the present teachings. The list is intended to be exemplary and is by no means exhaustive. Some possible fluorophores include: fluorescein (FL), which absorbs maximally at 492 nm and emits maximally at 520 nm; N,N,N',N'-tetramethyl-6-carboxyrhodamine (TAMRA™), which absorbs maximally at 555 nm and emits maximally at 580 nm; 5-carboxyfluorescein (5-FAM™), which absorbs maximally at 495 nm and emits maximally at 525 nm; 2',7'-dimethoxy-4',5'-dichloro-6-carboxyfluorescein (JOE™), which absorbs maximally at 525 nm and emits maximally at 555 nm; 6-carboxy-X-rhodamine (ROX™), which absorbs maximally at 585 nm and emits maximally at 605 nm; CY3™, which absorbs maximally at 552 nm and emits maximally at 570 nm; CY5™, which absorbs maximally at 643 nm and emits maximally at 667 nm; tetrachloro-fluorescein (TET™), which absorbs maximally at 521 nm and emits maximally at 536 nm; and hexachloro-fluorescein (HEX™), which absorbs maximally at 535 nm and emits maximally at 556 nm; NED™, which absorbs maximally at 546 nm and emits maximally at 575 nm; 6-FAM™, which emits maximally at approximately 520 nm; VIC® which emits maximally at approximately 550 nm; PET® which emits maximally at approximately 590 nm; and LIZ™, which emits maximally at approximately 650 nm. See SR Coticone et al., U.S. Pat. No. 6,780,588; AmpFlSTR® Identifiler™ PCR Amplification Kit User's Manual, pp. 1-3, Applied Biosystems (2001). Note that the above listed emission and/or absorption wavelengths are typical and can be used for general guidance purposes only; actual peak wavelengths may vary for different applications and under different conditions. Additional fluorophores can be selected for the desired absorbance and emission spectra as well as color as is known to one of skill in the art and are provided in TABLE 3.

TABLE 3

Commercially Available Dyes.

| Fluorophore | Abs (nm) | Em (nm) | Fluorophore | Abs (nm) | Em (nm) |
| --- | --- | --- | --- | --- | --- |
| Methoxycoumarin | 340 | 405 | Dansyl | 340 | 520 |
| Pyrene | 345 | 378 | Alexa Fluor ® 350 | 346 | 442 |
| CF ™ 350 | 347 | 448 | AMCA | 349 | 448 |
| DyLight 350 | 353 | 432 | Marina Blue ® dye | 365 | 460 |
| Dapoxyl ® dye | 373 | 551 | Dialkylamino-coumarin | 375 435 | 470-475 |

TABLE 3-continued

Commercially Available Dyes.

| Fluorophore | Abs (nm) | Em (nm) | Fluorophore | Abs (nm) | Em (nm) |
|---|---|---|---|---|---|
| Bimane | 380 | 458 | SeTau 380 | 381 | 480 |
| Hydroxycoumarin | 385 | 445 | ATTO 390 | 390 | 479 |
| Cascade Blue ® dye | 400 | 420 | Pacific Orange ® dye | 400 | 551 |
| DyLight ® 405 | 400 | 420 | Alexa Fluor ® 405 | 402 | 421 |
| SeTau 404 | 402 | 518 | Cascade Yellow ® dye | 402 | 545 |
| CF ™ 405S | 404 | 431 | CF ™ 405M | 408 | 452 |
| Pacific Blue ™ dye | 410 | 455 | PyMPO | 415 | 570 |
| DY-415 | 415 | 467 | SeTau 425 | 425 | 545 |
| Alexa Fluor ® 430 | 434 | 539 | ATTO 425 | 436 | 484 |
| ATTO 465 | 453 | 508 | NBD | 465 | 535 |
| Seta 470 | 469 | 521 | CF ™ 485 | 470-488 | 513 |
| DY-485XL | 485 | 560 | CF ™ 488A | 490 | 515 |
| DyLight ® 488 | 493 | 518 | DY 496 | 493 | 521 |
| Fluorescein | 494 | 518 | ATTO 495 | 495 | 527 |
| Alexa Fluor ® 488 | 495 | 519 | Oregon Green ® 488 | 496 | 524 |
| BODIPY ® 493/503 | 500 | 506 | CAL Fluor ® Green 520 | 500 | 522 |
| DY-480XL | 500 | 630 | ATTO 488 | 501 | 523 |
| Rhodamine Green dye | 502 | 527 | BODIPY ® FL | 505 | 513 |
| DY 505 | 505 | 530 | DY 510XL | 509 | 590 |
| 2',7'-Dichlorofluorescein | 510 | 532 | Oregon Green ® 514 | 511 | 530 |
| DY-481XL | 515 | 650 | ATTO 520 | 516 | 538 |
| Alexa Fluor ® 514 | 518 | 540 | CAL Fluor ® Gold 540 | 519 | 537 |
| DY 520XL | 520 | 664 | 4',5'-Dichloro- 2',7'-dimethoxy-fluorescein (JOE) | 522 | 550 |
| DY-521XL | 523 | 668 | Eosin | 524 | 544 |
| Rhodamine 6G | 525 | 555 | BODIPY ® R6G | 528 | 550 |
| Alexa Fluor ® 532 | 531 | 554 | ATTO 532 | 532 | 553 |
| BODIPY ® 530/550 | 534 | 554 | CAL Fluor ® Orange 560 | 534 | 556 |
| DY-530 | 539 | 561 | BODIPY ® TMR | 542 | 574 |
| DY-555 | 547 | 572 | DY556 | 548 | 573 |
| Quasar ® 570 | 548 | 570 | Cy 3 | 550 | 570 |
| CF ™555 | 550 | 570 | DY-554 | 551 | 572 |
| DY 550 | 553 | 578 | ATTO 550 | 554 | 576 |
| Tetramethyl-rhodamine (TMR) | 555 | 580 | Alexa Fluor ® 555 | 555 | 565 |
| Seta 555 | 556 | 570 | Alexa Fluor ® 546 | 556 | 575 |
| DY-547 | 557 | 574 | DY-548 | 558 | 572 |
| BODIPY ® 558/568 | 558 | 569 | DY-560 | 559 | 578 |
| DY 549 | 560 | 575 | DyLight ® 549 | 562 | 618 |
| CF ™ 568 | 562 | 583 | ATTO 565 | 563 | 592 |
| BODIPY ® 564/570 | 565 | 571 | CAL Fluor ® Red 590 | 566 | 588 |
| Lissamine rhodamine B | 570 | 590 | Rhodamine Red dye | 570 | 590 |
| BODIPY ® 576/589 | 576 | 590 | Alexa Fluor ® 568 | 578 | 603 |
| X-rhodamine | 580 | 605 | DY-590 | 580 | 599 |
| BODIPY ® 581/591 | 584 | 592 | CAL Fluor ® Red 610 | 587 | 608 |
| BODIPY ® TR | 589 | 617 | Alexa Fluor ® 594 | 590 | 617 |
| ATTO 590 | 594 | 624 | CF ™ 594 | 594 | 614 |
| CAL Fluor ® Red 615 | 595 | 615 | Texas Red ® dye | 595 | 615 |
| Naphthofluorescein | 605 | 675 | DY-682 | 609 | 709 |
| DY-610 | 610 | 630 | CAL Fluor ® Red 635 | 611 | 631 |
| ATTO 611x | 611 | 681 | Alexa Fluor ® 610 | 612 | 628 |
| ATTO 610 | 615 | 634 | CF ™ 620R | 617 | 639 |
| ATTO 620 | 619 | 643 | DY -615 | 621 | 641 |
| BODIPY ® 630/650 | 625 | 640 | ATTO 633 | 629 | 657 |
| CF ™ 633 | 630 | 650 | Seta 632 | 632 | 641 |
| Alexa Fluor ® 633 | 632 | 647 | Alexa Fluor ® 635 | 633 | 647 |
| DY-634 | 635 | 658 | Seta 633 | 637 | 647 |
| DY-630 | 636 | 657 | DY-633 | 637 | 657 |
| DY-632 | 637 | 657 | DyLight ® 633 | 638 | 658 |
| Seta 640 | 640 | 656 | CF ™ 640R | 642 | 662 |
| ATTO 647N | 644 | 669 | Quasar ® 670 | 644 | 670 |
| ATTO 647 | 645 | 669 | DY-636 | 645 | 671 |
| BODIPY ® 650/665 | 646 | 660 | Seta 646 | 646 | 656 |
| DY-635 | 647 | 671 | Square 635 | 647 | 666 |
| Cy 5 | 649 | 650/670 | Alexa Fluor ® 647 | 650 | 668 |
| CF ™ 647 | 650 | 665 | Seta 650 | 651 | 671 |
| Square 650 | 653 | 671 | DY-647 | 653 | 672 |
| DY-648 | 653 | 674 | DY-650 | 653 | 674 |
| DyLight ® 649 | 654 | 673 | DY-652 | 654 | 675 |
| DY-649 | 655 | 676 | DY-651 | 656 | 678 |

TABLE 3-continued

Commercially Available Dyes.

| Fluorophore | Abs (nm) | Em (nm) | Fluorophore | Abs (nm) | Em (nm) |
|---|---|---|---|---|---|
| Square 660 | 658 | 677 | Seta 660 | 661 | 672 |
| Alexa Fluor ® 660 | 663 | 690 | ATTO 655 | 663 | 684 |
| Seta 665 | 667 | 683 | Square 670 | 667 | 685 |
| Seta 670 | 667 | 686 | DY-675 | 674 | 699 |
| DY-677 | 673 | 694 | DY-676 | 674 | 699 |
| Alexa Fluor ® 680 | 679 | 702 | IRDye ® 700DX | 680 | 687 |
| ATTO 680 | 680 | 700 | CF ™ 680R | 680 | 701 |
| CF ™ 680 | 681 | 698 | Square 685 | 683 | 703 |
| DY-680 | 690 | 709 | DY-681 | 691 | 708 |
| DyLight ® 680 | 692 | 712 | Seta 690 | 693 | 714 |
| ATTO 700 | 700 | 719 | Alexa Fluor ® 700 | 702 | 723 |
| Seta 700 | 702 | 728 | ATTO 725 | 725 | 752 |
| ATTO 740 | 740 | 764 | Alexa Fluor ® 750 | 749 | 775 |
| Seta 750 | 750 | 779 | DyLight ® 750 | 752 | 778 |
| CF ™ 750 | 755 | 777 | CF ™ 770 | 770 | 797 |
| DyLight ® 800 | 777 | 794 | IRDye ® 800RS | 770 | 786 |
| IRDye ® 800 CW | 778 | 794 | Alexa Fluor ® 790 | 782 | 805 |
| CF ™ 790 | 784 | 806 | | | |

Various embodiments of the multiplex panel may encompass a single multiplex dye system including at least five different dyes. The set of amplification primers may be labeled with one of the at least five different dyes. The at least 5 different fluorescent dyes may be spectrally distinct. These at least five dyes may include any five of the above-listed dyes, or any other five dyes known in the art, or 6-FAM™, VIC®, NED™, PET®, and LIZ™ dyes. Other embodiments may include a single multiplex system comprising at least six different dyes. These at least six dyes may include any six of the above-listed dyes, or any other six dyes known in the art, 6-FAM™, VIC®, NED™, TAZ™, SID™, and LIZ™ dyes with the TAZ dye having a maximum emission at approximately 600 nm, and the SID dye having a maximum emission at approximately 620 nm (LIZ™ dye was used to label the size standards). The dyes may be energy transfer dyes. An energy transfer dye has a donor dye which absorbs excitation energy and transfers energy to excite an acceptor dye. The energy transfer dye may be configured to efficiently transfer energy from the donor dye to the acceptor dye. A multiplex energy transfer dye system having more than 1 dye may have the same dye as a donor dye for each of the energy transfer dye set member, while having different, spectrally distinct acceptor dyes for each member of the dye set.

Allelic Ladder. The allelic ladder serving as a reference standard and nucleic acid size marker for the amplified allele(s) from one or more STR markers of the multiplex panel may have one of many possible compositions. In some embodiments, the allelic ladder may include all known alleles for the STR markers in the analysis. In other embodiments, the allelic ladder may not include all known alleles; additional alleles can be identified by size comparison with the existing allelic ladder components. In some embodiments, the allelic ladder can incorporate size standards for the alleles of different STRs, including a subset of all the STR markers in a multiplex analysis. Alternatively, the allelic ladder may include size standards for the alleles of all the STR markers in a multiplex analysis. The allelic ladder for a multiplex analysis may be a combination of allelic ladders. In some embodiments, the allelic ladder can be DNA. In some embodiments the allelic ladder can include non-naturally occurring nucleic acid analogs, which may further include nucleotide analogs. In some embodiments, the allelic ladder may include both naturally occurring nucleotides and nucleotide analogs. In some embodiments, the allelic ladder may include non-nucleotide moieties. The different individual size standards within an allelic ladder can, in some embodiments, be labeled with a detectable label, e.g., a fluorophore. In some embodiments, the allelic ladder components are labeled with the same fluorophore. In some embodiments, the allelic ladder components are labeled with different fluorophores. The different fluorophores may be spectrally distinct. The size standards can be selected to serve as reference for a specific pair (or pairs) of oligonucleotide primers. For example if a first set of primers for marker X with a tetranucleotide repeat produces a 150 base pair amplicon corresponding to allele 7, a corresponding first allelic ladder component will serve as a size standard for the 150 base amplicons. The first set of primers for marker X may also produces a 154 base pair amplicon corresponding to allele 8 of marker X, and a corresponding second allelic ladder component will serve as a size standard for the 154 base amplicons. Thus different size standards for different size amplicons of the same marker are contemplated. The size standard for a given amplicon derived from a given allele may have a nucleic acid base sequence that is the same or different from the nucleic acid base sequence of the amplicon or allele from which the amplicon is derived. Following the construction of allelic ladders for individual loci, the ladders may be electrophoresed at the same time as the amplification products. Alternatively, the ladders may be electrophoresed separately after a preselected number of analysis runs for comparison to the analysis results. For allele analysis in electrophoresis systems, the size standard can be selected to have the same electrophoretic mobility as the amplicon of interest. Equivalent electrophoretic mobility of the size standard and the amplicon or the allele from which the amplicon is derived may be achieved by including non-nucleotide moieties in either the standard or the amplicon. Alternatively, in some embodiments, the size standard can be selected to have a different electrophoretic mobility than the amplicon of interest. With an understanding of the predicable nature of the difference in mobility between the size standard and the amplicon of interest, the identity of the amplicon may be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected to have different separation properties from the amplicon of interest. Similarly given an understanding of the predicable nature of weight/charge difference, the identity of the amplicon may be determined. The individual size standard components of the allelic ladder may be produced by expression, synthesis or semi-synthesis.

In one embodiment of allelic ladders for multiplex panels described herein, the range (from the smallest allele to the largest allele) of allelic size standards for each STR marker in the panel may be separated by a two base pair difference from the preceding and following ranges of allele size standards for the corresponding adjacent STR markers in the multiplex panel.

The range for each STR marker may also include a virtual bin at the smallest end and the largest end of the range of alleles for future use. Additionally, software processing the electrophoretic separation results may further be configured to assign virtual bins for microvariant alleles, for example, wherein only a partial repeat of the tandem repeat has occurred in the target nucleic acid.

Figure 15A:
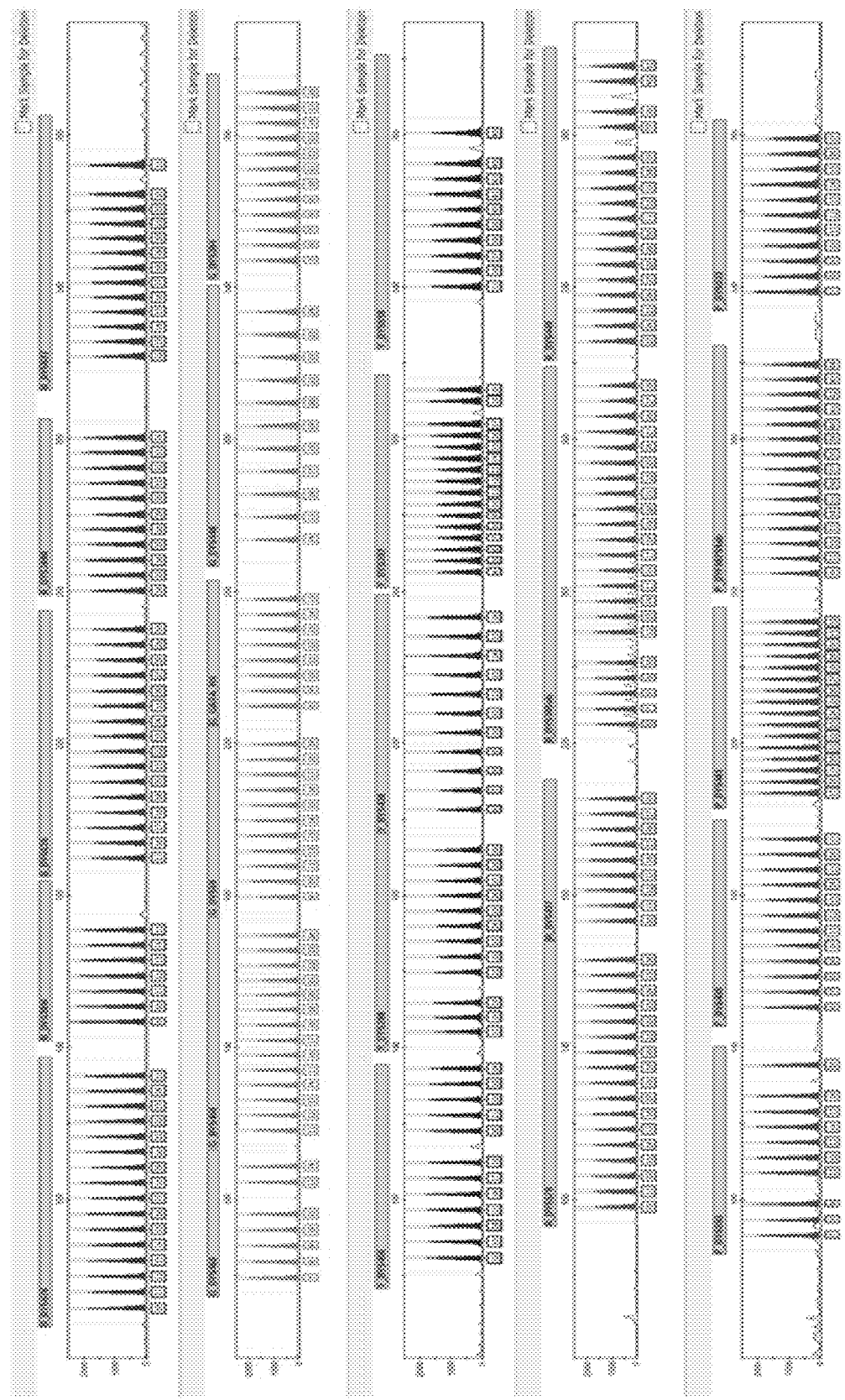
FIG. 15A is a graphical representation of one embodiment of an allelic ladder for the multiplex panel of FIG. 10 (Panel 7).

One exemplary allelic ladder is shown in FIG. 15A. The allelic ladder shown in FIG. 15A may be used to identify the alleles for the multiplex Panel 7. The first dye channel is shown in the top panel where the first marker is DYS576 with alleles 10, 11, 12, 13, 14, 15, 16, 17, 18, 19, 20, 21, 22, 23, 24 and 25 detected in a region from about 70 bp to about 135 bp; the second marker is DYS389I with alleles 9, 10, 11, 12, 13, 14, and 15 detected in a range from about 145 bp to about 175 bp; the third marker is DYS635 with alleles 15, 16, 17, 18, 19, 20, 21, 22, 23, 24, 25, 26, 27, 28, 29, and 30 detected in a range from about 190 bp to about 250 bp; the fourth marker is DYS389II with alleles 24, 25, 26, 27, 28, 29, 30, 31, 32, 33, and 34 detected in a range from about 260 bp to about 300 bp; and the fifth marker is DYS627 with alleles 12, 13, 14, 15, 16, 17, 18, 19, 20, 21, 22, 23, and 25 detected in a range from about 320 bp to about 375 bp. The second dye channel is shown in the second panel from the top of FIG. 15A where the first marker is DYS460 with alleles 7, 8, 9, 10, 11, 13, and 14 detected in a range from about 75 bp to about 110 bp; the second marker is DYS458 with alleles 11, 12, 13, 14, 15, 16, 17, 18, 19, 20, 21, 22, 23, and 24 detected in a range from about 115 bp to about 170 bp; the third marker is DYS19 with alleles 9, 10, 11, 12, 13, 14, 15, 16, 17, 18 and 19 detected in a range from about 180 bp to about 220 bp; the fourth marker is GATA-H4 with alleles 8, 9, 10, 11, 12, 13, 14, and 15 detected in a range from about 220 bp to about 260 bp; the fifth marker is DYS448 with alleles 14, 15, 16, 17, 18, 19, 20, 21, 22, 23, and 24 detected in a range from about 275 bp to about 335 bp; and the sixth marker is DYS391 with alleles 5, 6, 7, 8, 9, 10, 11, 12, 13, 14, and 15 detected in a range from about 345 bp to about 395 bp. The third dye channel is shown in the third panel from the top of FIG. 15A where the first marker is DYS456 with alleles 12, 13, 14, 15, 16, 17, 18, 20, 21, 22, 23, and 24 detected in a range from about 75 bp to about 135 bp; the second marker is DYS390 with alleles 17, 18, 19, 21, 22, 23, 24, 25, 26, 27, 28 and 29 detected in a range from about 140 bp to about 195 bp; the third marker is DYS438 with alleles 6, 7, 8, 9, 10, 11, 12, 13, 14, 15, and 16 detected in a range from about 200 bp to about 255 bp; the fourth marker is DYS392 with alleles 4, 5, 6, 7, 8, 9, 10, 11, 12, 13, 14, 15, 16, 17, 19, and 20 detected in a range from about 265 bp to about 305 bp; and the fifth marker is DYS518 with alleles 35, 36, 37, 38, 39, 40, 41, 42, 43 and 45 detected in a range from about 340 bp to about 380 bp. The fourth dye channel is shown in the fourth panel from the top of FIG. 15A, where the first marker is DYS570 with alleles 10, 11, 12, 13, 14, 15, 16, 17, 18, 19, 20, 21, 22, 23, 24, 25, and 26 are detected in a range from about 95 bp to about 165 bp; the second marker is DYS437 with alleles 10, 11, 12, 13, 14, 15, 16, 17 and 18 detected in a range from about 175 bp to about 205 bp; the third marker is DYS385ab with alleles 6, 7, 8, 9, 10, 12, 13, 14, 15, 16, 17, 18, 19, 20, 21, 22, 23, 24, 25, 26, 27, and 28 detected in a range from about 225 bp to about 305 bp; and the fourth marker is DYS449 with alleles 23, 24, 25, 26, 27, 28, 29, 30, 31, 32, 33, 34, 35, 37, 38, 40, and 41 detected in a range from about 325 bp to about 400 bp. The fifth dye channel is shown in the fifth panel from the top of FIG. 15A, where the first marker is DYS393 with alleles 7, 8, 9, 11, 12, 13, 14, 15, 16, and 18 detected in a range from about 90 bp to about 135 bp; the second marker is DYS439 with alleles 6, 7, 8, 9, 10, 11, 12, 13, 14, 15, 16 and 17 detected in a range from about 150 bp to about 195 bp; the third marker is DYS481 with alleles 17, 18, 19, 20, 21, 22, 23, 24, 25, 26, 27, 28, 29, 30, 31, and 32 detected in a range from about 205 bp to about 255 bp; the fourth marker is DYF387S1ab with alleles 30, 31, 32, 33, 34, 35, 36, 37, 38, 39, 40, 41, 42, 43, and 44 detected in a range from about 265 bp to about 320 bp, and the fifth marker is DYS533 with alleles 7, 8, 9, 10, 11, 12, 13, 14, 15, 16, and 17 detected in a range from about 340 bp to about 380 bp. The sixth dye channel containing a size standard is not shown in FIG. 15A. In this embodiment, virtual bins are provided at both the low bp and the high bp sides of the allele detection range for each marker.

In another embodiment, the allelic ladder is as above, with an additional allele 10, for DYS456, to provide a range for DYS456 with alleles 10, 12, 13, 14, 15, 16, 17, 18, 20, 21, 22, 23, and 24 detected in a range from about 70 bp to about 135 bp. The additional range for DYS456 is shown specifically in FIG. 15B.

Figure 15B:
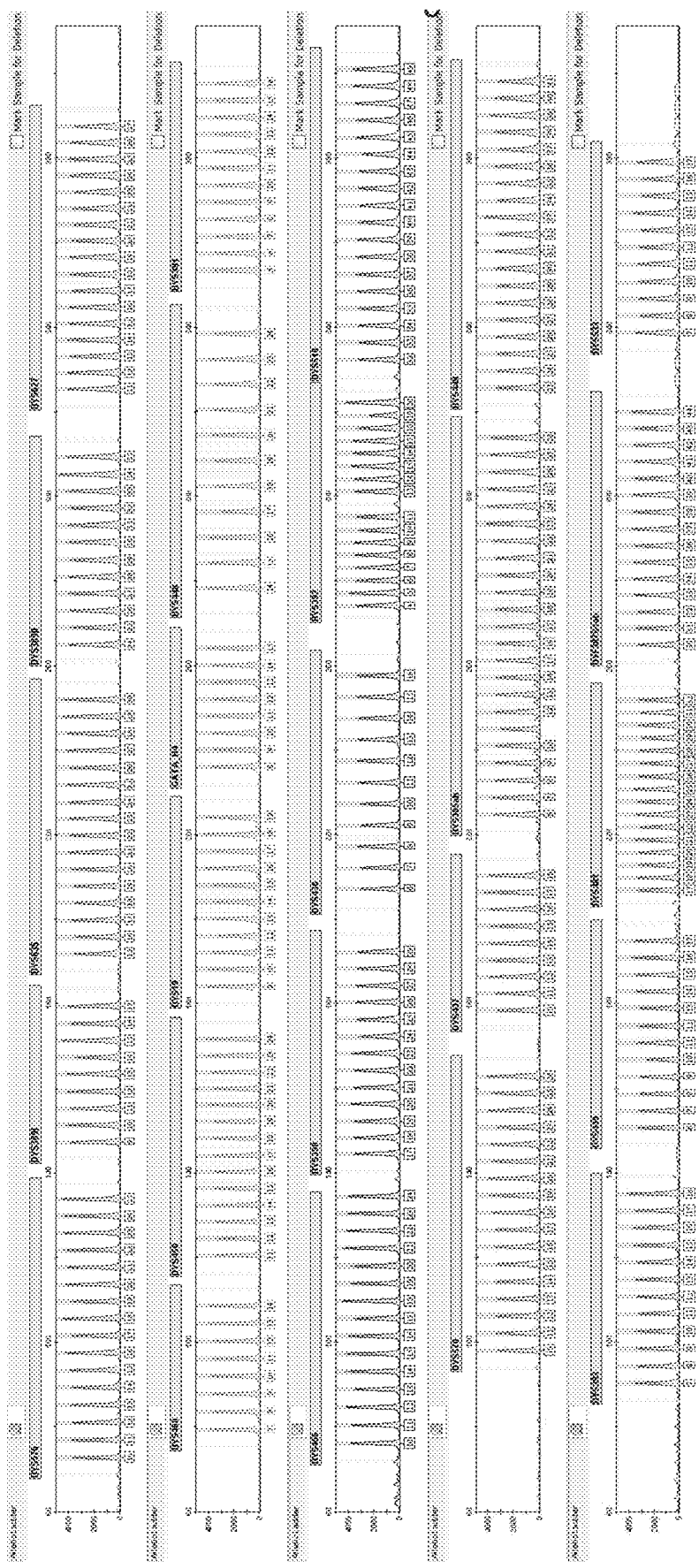
FIG. 15B is a graphical representation of another embodiment of an allelic ladder for the multiplex panel of FIG. 10 (Panel 7).

In yet another embodiment, the allelic ladder is as described for the allelic ladder of FIG. 15B, with the addition of allele 12 for DYS392.

In one aspect, the invention provides for an allelic ladder, where the allelic ladder includes at least one size standard for at least one allele of at least 11 Y-STR markers, wherein the at least one size standard for the at least one allele of the at least 11 Y-STR markers has a base pair size of less than about 220 base pairs. The allelic ladder may include a size standard for each of more than one allele of the at least 11 Y-STR markers, wherein each of the size standards has a base pair size of less than about 220 base pairs. The allelic ladder may include a size standard for one or more alleles of the at least 11 Y-STR markers where the at least 11 Y-STR markers include DYS576, DYS389I, DYS460, DYS458, DYS19, DYS456, DYS390, DYS570, DYS437, DYS393, and DYS439. The allelic ladder may further include at least one size standard for at least one allele for at least five rapidly mutating Y-STR markers. The allelic ladder may include a size standard for each of more than one allele of the at least five rapidly mutating Y-STR markers. The allelic ladder may include a size standard for each of more than one allele of the at least five rapidly mutating Y-STR markers where the at least five rapidly mutating Y-STR markers include DYF387S1ab, DYS449, DYS570, DYS576, and DYS627. The allelic ladder may include a size standard for each of more than one allele of the at least five rapidly mutating Y-STR markers where the at least five rapidly mutating Y-STR marker further include DYS518. The allelic ladder may include a size standard for each of more than one allele of the at least 11 Y-STR markers where the at least 11 Y-STR markers include DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. The allelic ladder may include a size standard for each of more than one allele of the at least 11 Y-STR markers where the at least 11 Y-STR markers include DYF387S1ab, DYS19, DYS385ab, DYS389I, DYS389II, DYS390, DYS391, DYS392, DYS393, and DYS460, DYS437, DYS438, DYS439, DYS448, DYS449, DYS456, DYS458, DYS481, DYS533, DYS570, DYS576, DYS627, DYS635, DYS643, and Y-GATA-H4. The allelic ladder may include at least one size standard for the at least one allele of the at least 11 Y-STR markers, where the at least one size standard is fluorescently labeled. The allelic ladder may include a size standard for each of one or more alleles of the at least 11 Y-STR markers, where a plurality of size standards for the one or more alleles of each of the at least 11 Y-STR markers is labeled with one of five spectrally distinct fluorescent dyes. The allelic ladder may further include a size standard labeled with a sixth dye, where the size standard provides a measure of base pair size.

The Sample. In some embodiments, the sample encompassing the target nucleic acid being analyzed is from one or more of hair, feces, blood, tissue, urine, saliva, cheek cells, vaginal cells, skin, bone, tooth, buccal sample, amniotic fluid containing placental cells, and amniotic fluid containing fetal cells and semen. In some embodiments, the sample may originate from a crime scene, a sample associated with a crime scene, a sample taken from a suspect, a reference sample or a sample taken from a human under consideration. In other embodiments, the sample may be an archeological sample, a maternity sample, a paternity sample, a missing person sample.

Methods. In some embodiments, the present teachings relate to methods for detecting and identifying alleles of a short tandem repeat (STR) sequence in a target nucleic acid. In some embodiments, the method for detecting and identifying alleles of a STR sequence includes amplifying at least one short tandem repeat sequence from a target nucleic acid by polymerase chain reaction (PCR) using locus-specific oligonucleotide primers. Following amplification, the amplification product's resulting amplified short tandem repeat sequence is compared with the amplified allelic ladder to call the allele based on matching the sample's amplification product to the allele standard found within the allelic ladder. In some embodiments, the method for detecting and identifying alleles of a short tandem repeat sequence uses PCR amplification of the target nucleic acid and employs oligonucleotide primer pairs. The methods include workflows suitable for analysis of extracted DNA, which may be used for casework samples, as well as direct amplification, which may be used for single source samples.

Methods for analyzing nucleic acids are well known to one of skill in the art as are methods for amplification by PCR. The analyses of the PCR amplification product, i.e., amplicon, includes, but is not limited to, detection, identification and in some instances, sequencing the amplification product, methods well established and known to one of skill in the art. In some embodiments, the method for detecting and identifying alleles of a short tandem repeat sequence involves comparing the amplified short tandem repeat amplification sequence to the corresponding allelic ladder by electrophoresis. Many electrophoresis methods for the separation of alleles are known to one of skill in the art and include, but are not limited to, denaturing and non-denaturing gel electrophoresis, capillary electrophoresis, and the like. Methods for sequencing the amplification product, e.g., Sanger sequencing are well established and known to one of skill in the art.

In some embodiments of the present teachings, methods are provided wherein one or more samples are analyzed for the determination of STR alleles present in the sample. In some embodiments, the method includes isolating nucleic acid from the sample and PCR amplifying the nucleic acid to generate an amplification product.

The amplification product is then compared to an allelic ladder mixture including one or more alleles per marker. Various embodiments of the present teachings relate to newly expanded groups of alleles of selected Y-STR loci. Embodiments of the claimed inventions include allelic ladders for the detection of these novel alleles of the selected Y-STR loci.

Samples of genomic DNA can be prepared for use in the methods of the present teaching using any procedures for sample preparation that are compatible with the subsequent amplification of DNA. Many such procedures are known by those skilled in the art. Some examples are DNA purification by phenol extraction (J. Sambrook et al. (1989), in Molecular Cloning: A Laboratory Manual, Second Edition, Cold Spring Harbor Laboratory Press, Cold Spring Harbor, N.Y., pp. 9.14-9.19), and partial purification by salt precipitation (S. Miller et al. (1988), Nucl. Acids Res. 16:1215) or chelex (PS Walsh et al. (1991), BioTechniques 10:506-513; CT Comey et al. (1994), J. Forensic Sci. 39:1254) and the release of unpurified material using untreated blood (J. Burckhardt (1994), PCR Methods and Applications 3:239-243; RBE McCabe (1991), PCR Methods and Applications 1:99-106; BY Nordvag (1992), BioTechniques 12:4 pp. 490-492).

Once a sample of genomic DNA is prepared, the target loci can be co-amplified in the multiplex amplification step of the present teaching. Alternatively, the sample containing genomic DNA may be directly amplified from a substrate that the sample was collected upon, including but not limited to paper, fabric or fiber substrates.

Any of a number of different amplification methods can be used to amplify the loci, such as, for example, PCR (RK Saiki et al. (1985), Science 230: 1350-1354), transcription based amplification (D Y Kwoh and T J Kwoh (1990), American Biotechnology Laboratory, October, 1990) and strand displacement amplification (SDA) (GT Walker et al. (1992), Proc. Natl. Acad. Sci., U.S.A. 89: 392-396). In some embodiments of the present teaching, multiplex amplification can be effected via PCR, in which the DNA sample is subjected to amplification using primer pairs specific to each locus in the multiplex.

The chemical components of a standard PCR generally include a solvent, DNA polymerase, deoxyribonucleoside triphosphates ("dNTPs"), oligonucleotide primers, a divalent metal ion, and a DNA sample expected to contain the target(s) for PCR amplification. Water can generally be used as the solvent for PCR, typically including a buffering agent and non-buffering salts such as KCl. The buffering agent can be any buffer known in the art, such as, but not limited to, Tris-HCl, and can be varied by routine experimentation to optimize PCR results. Persons of ordinary skill in the art are readily able to determine optimal buffering conditions. PCR buffers can be optimized depending on the particular enzyme used for amplification.

Divalent metal ions can often be advantageous to allow the polymerase to function efficiently. For example, the magnesium ion is one which allows certain DNA polymerases to function effectively. Typically $MgCl_2$ or $MgSO_4$ can be added to reaction buffers to supply the optimum magnesium ion concentration. The magnesium ion concentration required for optimal PCR amplification may depend on the specific set of primers and template used. Thus, the amount of magnesium salt added to achieve optimal amplification is often determined empirically, and is a routine practice in the art. Generally, the concentration of magnesium ion for optimal PCR can vary between about 1 and about 10 mM. A typical range of magnesium ion concentration in PCR can be between about 1.0 and about 4.0 mM, varying around a midpoint of about 2.5 mM. Alternatively, the divalent ion manganese can be used, for example in the form of manganese dioxide ($MnO_2$), titrated to a concentration appropriate for optimal polymerase activity, easily determined by one of skill in the art using standard laboratory procedures.

The dNTPs, which are the building blocks used in amplifying nucleic acid molecules, can typically be supplied in standard PCR at a concentration of, for example, about 40-200 μM each of deoxyadenosine triphosphate ("dATP"), deoxyguanosine triphosphate ("dGTP"), deoxycytidine triphosphate ("dCTP"), and deoxythymidine triphosphate ("dTTP"). Other dNTPs, such as deoxyuridine triphosphate ("dUTP"), dNTP analogs (e.g., inosine), and conjugated dNTPs can also be used, and are encompassed by the term "dNTPs" as used herein. While use of dNTPs at concentrations of about 40-200 M each can be amenable to the methods of this teaching, concentrations of dNTPs higher than about 200 μM each could be advantageous. Thus, in some embodiments of the methods of these teachings, the concentration of each dNTP is generally at least about 500 μM and can be up to about 2 mM. In some further embodiments, the concentration of each dNTP may range from about 0.5 mM to about 1 mM. Specific dNTP concentrations used for any multiplex amplification can vary depending on multiplex conditions, and can be determined empirically by one of skill in the art using standard laboratory procedures.

The enzyme that polymerizes the nucleotide triphosphates into the amplified products in PCR can be any DNA polymerase. The DNA polymerase can be, for example, any heat-resistant polymerase known in the art. Examples of some polymerases that can be used in this teaching are DNA polymerases from organisms such as *Thermus aquaticus, Thermus thermophilus, Thermococcus litoralis, Bacillus stearothermophilus, Thermotoga maritima* and *Pyrococcus* sp. The enzyme can be acquired by any of several possible methods; for example, isolated from the source bacteria, produced by recombinant DNA technology or purchased from commercial sources. Some examples of such commercially available DNA polymerases include AmpliTaq Gold® DNA polymerase; AmpliTaq Platinum® DNA polymerase; AmpliTaq® DNA Polymerase; AmpliTaq® DNA Polymerase Stoffel Fragment; rTth DNA Polymerase; and rTth DNA Polymerase, XL (all manufactured by Applied Biosystems, Foster City, Calif.). Other examples of suitable polymerases include Tne, Bst DNA polymerase large fragment from *Bacillus stearothermophilus*, Vent and Vent Exo- from *Thermococcus litoralis*, Tma from *Thermotoga maritima*, Deep Vent and Deep Vent Exo- and Pfu from *Pyrococcus* sp., and mutants, variants and derivatives of the foregoing.

Other known components of PCR can be used within the scope of the present teachings. Some examples of such components include sorbitol, detergents (e.g., Triton X-100, Nonidet P-40 (NP-40), Tween-20) and agents that disrupt mismatching of nucleotide pairs, such as, for example, dimethylsulfoxide (DMSO), and tetramethylammonium chloride (TMAC), and uracil N-glycosylase or other agents which act to prevent amplicon contamination of the PCR and/or unwanted generation of product during incubation or preparation of the PCR, before the PCR procedure begins.

PCR cycle temperatures, the number of cycles and their durations can be varied to optimize a particular reaction, as a matter of routine experimentation. Those of ordinary skill in the art will recognize the following as guidance in determining the various parameters for PCR, and will also recognize that variation of one or more conditions is within the scope of the present teachings. Temperatures and cycle times are determined for three stages in PCR: denaturation, annealing and extension. One round of denaturation, annealing and extension is referred to as a "cycle." Denaturation can generally be conducted at a temperature high enough to permit the strands of DNA to separate, yet not so high as to destroy polymerase activity. Generally, thermoresistant polymerases can be used in the reaction, which do not denature but retain some level of activity at elevated temperatures. However, heat-labile polymerases can be used if they are replenished after each denaturation step of the PCR. Typically, denaturation can be conducted above about 90° C. and below about 100° C. In some embodiments, denaturation can be conducted at a temperature of about 94-95° C. Denaturation of DNA can generally be conducted for at least about 1 to about 30 seconds. In some embodiments, denaturation can be conducted for about 1 to about 15 seconds. In other embodiments, denaturation can be conducted for up to about 1 minute or more. In addition to the denaturation of DNA, for some polymerases, such as AmpliTaq Gold®, incubation at the denaturation temperature also can serve to activate the enzyme. Therefore, it can be advantageous to allow the first denaturation step of the PCR to be longer than subsequent denaturation steps when these polymerases are used.

During the annealing phase, oligonucleotide primers anneal to the target DNA in their regions of complementarity and are substantially extended by the DNA polymerase, once the latter has bound to the primer-template duplex. In a conventional PCR, the annealing temperature can typically be at or below the melting point ($T_m$) of the least stable primer-template duplex, where $T_m$ can be estimated by any of several theoretical methods well known to practitioners of the art. For example, $T_m$ can be determined by the formula:

$$T_m = (4° \text{ C. } X \text{ number of } G \text{ and } C \text{ bases}) + (2° \text{ C. } X \text{ number of } A \text{ and } T \text{ bases}).$$

Typically, in standard PCR, the annealing temperature can be about 5-10° C. below the estimated $T_m$ of the least stable primer-template duplex. The annealing time can be between about 30 seconds and about 2 minutes. The annealing phase is typically followed by an extension phase. Extension can be conducted for a sufficient amount of time to allow the polymerase enzyme to complete primer extension into the appropriately sized amplification products.

The number of cycles in the PCR (one cycle includes denaturation, annealing and extension) determines the extent of amplification and the subsequent amount of amplification product. PCR results in an exponential amplification of DNA molecules. Thus, theoretically, after each cycle of PCR, there is twice the number of products that were present in the previous cycle, until PCR reagents are exhausted and a plateau is reached at which no further amplification products are generated. Typically, about 20-30 cycles of PCR may be performed to reach this plateau. More typically, about 25-30 cycles may be performed, although cycle number is not particularly limited. The number of cycles used may depend on the nature of the input sample. In some cases, an extracted DNA sample may require 30 cycles, while a directly amplified DNA sample may only require 26 cycles. One of skill may adjust both cycle numbers and specific details of temperature and time intervals in order to optimize the reaction conditions.

For some embodiments, it can be advantageous to incubate the reactions at a certain temperature following the last phase of the last cycle of PCR. In some embodiments, a prolonged extension phase can be selected. In other embodiments, an incubation at a low temperature (e.g., about 4° C.) can be selected.

Various methods can be used to evaluate the products of the amplified alleles in the mixture of amplification products obtained from the multiplex reaction including, for example, detection of fluorescent labeled products, detection of ions released during each extension reaction (ion semiconductor sequencing), detection of pyrophosphate release during each extension reaction, detection of radioisotope labeled products, silver staining of the amplification products, or the use of DNA intercalator dyes such as ethidium bromide (EtBr) and SYBR green cyanine dye to visualize double-stranded amplification products. Fluorescent labels suitable for attachment to primers for use in the present teachings are numerous, commercially available, and well-known in the art. With fluorescent analysis, at least one fluorescent labeled primer can be used for the amplification of each locus. Fluorescent detection may be desirable over radioactive methods of labeling and product detection, for example, because fluorescent detection does not require the use of radioactive materials, and thus avoids the regulatory and safety problems that accompany the use of radioactive materials. Fluorescent detection with labeled primers may also be selected over other non-radioactive methods of detection, such as silver staining and DNA intercalators, because fluorescent methods of detection generally reveal fewer amplification artifacts than do silver staining and DNA intercalators. This is due in part to the fact that only the amplified strands of DNA with labels attached thereto are detected in fluorescent detection, whereas both strands of every amplified product are stained and detected using the silver staining and intercalator methods of detection, which result in visualization of many non-specific amplification artifacts. Additionally, there are potential health risks associated with the use of EtBr and SYBR. EtBr is a known mutagen; SYBR, although less of a mutagen than EtBr, is generally suspended in DMSO, which can rapidly pass through skin.

Fluorescence detection may also be useful in sequencing by synthesis methods, where each nucleotide extension reaction releases a fluorescent signal that is differentiable for each of the four natural nucleotides. Nothing in this disclosure would limit one of skill from using such detection methods with the primers and of the multiplex panels of the invention, and methods described herein.

Detection of the amplified alleles is not limited, however, to fluorescence detection and may be conveniently detected via pyrosequencing or ionic semiconductor sequencing techniques. The selection of core loci in combination with additional loci selected for gene diversity and/or high mutational rate makes the multiplex assays described herein equally useful for those detection methodologies.

Improved Capabilities of the Panels in the Methods of the Invention. The Panel 6 and Panel 7 multiplex experimental results demonstrate the increased sensitivity, robustness, and discriminatory power of the multiplex assay panels designed and performed as described here. As shown in Examples 1 and 2, both Panel 6 and Panel 7 provide higher proportions of complete Y-STR profiles even at very low levels of input DNA. Examples 3, 4, and 5 show that the primer sets of Panel 6 and Panel 7 permit higher proportion of complete Y-STR profiles for decreasing amounts of male DNA in the presence of increasing amounts of female DNA, relative to a commercially available panel. Thus the primers of Panel 6 and Panel 7 offer higher specificity for male DNA compared to the Y®filer panel. Examples 6 and 7 demonstrate that the primer sets of Panel 6 and Panel 7 provide improved intracolor peak balance overall and also in the presence of increasing amounts of female DNA in the input sample. Intracolor balance is defined below, but represents a measure of robust and equivalent amplification across all alleles for which the primers are labeled with the same fluorescent dye. This measure is another mark of the specificity of the primers with respect to the desired target male DNA vs hybridization or association with inhibitors or with female DNA. Examples 8, 9, and 10 demonstrate that the primer sets and chemistry used for Panel 6 and 7 provide more significantly robust amplification of target male DNA in the presence of varying concentrations of PCR inhibitors such as humic acid or hematin, compared to the amplification seen with the Y®filer panel. These results are particularly important for forensic or crime scene samples. Example 11 shows the improved results possible using the more robust intracolor balance characteristics of Panel 6 or 7, in order to identify minor male contributor to a mixed male input DNA sample. As shown in Examples 13 and 15, Panel 7 demonstrates increased ability to differentiate between a father and son, compared to other commercially available multiplex Y-STR panels. This improved differentiation (alternatively, ability to discriminate between a father and son) affords a greater possibility of identifying a male individual specifically than previously possible. This improved discrimination also affords the ability to more positively exclude a male individual from consideration as a potential lead in criminal, forensic or other evidentiary scenarios. Example 14 demonstrates the increased ability to resolve haplotypes using Panel 7 multiplex relative to the use of Y®filer, including groups having greater ethnic variety, i.e., in more groups of non-European lineage. Therefore, the multiplex panels of primers, and the methods of use thereof, offer surprisingly robust, sensitive, and specific Y-STR profile results. These improvements are badly needed in the field of forensics, human identification and justice.

A method is provided to amplify alleles of Y-STR markers of a human male including the steps of: contacting a sample suspected to contain a DNA sample of a human male with a set of amplification primers including primers for the amplification of the alleles of at least 11 Y-STR markers; and amplifying the sample thereby forming a plurality of sets of amplicons of the at least 11 Y-STR markers where each set of the amplicons has a base pair size less than about 220 base pairs. The method may further include the step of detecting each set of amplicons whereby the alleles of the at least 11 Y-STR markers are identified. In some embodiments, the detecting step is a fluorescence detection step. In some embodiments, the detecting step is performed by separating the plurality of sets of amplicons using a mobility dependent analysis, where the plurality of sets of amplicons is fluorescently labeled. In other embodiments, the detecting step does not detect fluorescence. In embodiments, when the detecting step does not detect fluorescence, the detecting step may include ion semiconductor detection, pyrophosphate release detection, or mass spectrometry detection. In various embodiments of the method, the set of amplification primers may further include primers for the amplification of at least 5 Y-STR markers where the primers may be configured to provide each set of amplicons of the at least 5 Y-STR markers having a base pair size greater than about 220 base pairs. In various embodiments of the method, when the set of amplification primers amplifies more than 11 Y-STR markers, then the set of primers may be configured to provide all of the sets of amplicons of the more than 11 Y-STR markers having a base pair size less than about 400 base pairs. In various embodiments of the method, when the set of amplification primers amplifies more than 11 Y-STR markers, then the set of primers may be configured to provide all of the sets of amplicons of the more than 11 Y-STR markers having a base pair size less than about 410 base pairs. In various embodiments of the method, when the set of amplification primers amplifies more than 11 Y-STR markers, then the set of primers may be configured to provide all of the sets of amplicons of the more than 11 Y-STR markers having a base pair size less than about 420 base pairs. In some embodiments of the method, when the amplification primer set amplifies more than 11 Y-STR markers, then the primer set may include primers for the amplification of 25 Y-STR markers. In some embodiments, the primer set for the amplification of 25 Y-STR markers, includes at least two double copy markers. In some embodiments, the set of amplification primers may be labeled with one of at least 5 fluorescent dyes. In some other embodiments, each set of the amplicons of the at least 11 Y-STR markers may be labeled with one of at least 5 fluorescent dyes. In various embodiments of the method, the at least 5 fluorescent dyes used to label the primers and/or the amplicons may be configured to be spectrally distinct. The set of amplification primers used in the method may further include at least one amplification primer that includes a mobility modifier. In some embodiments of the method, the at least one set of amplicons may include a mobility modifier. In various embodiments of the methods, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the set of amplification primers amplifying the at least 11 Y-STR markers, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments of the method, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, the method includes a set of amplification primers for the amplification of the alleles of 27 Y-STR markers.

In another aspect, a method is provided to amplify alleles of Y-STR markers of a human male including the steps of: contacting a sample suspected to contain a DNA sample of a human male with a set of amplification primers including primers for the amplification of the alleles of at least 22 Y-STR markers, wherein at least 5 of the Y-STR markers are rapidly mutating loci; and amplifying the sample thereby forming a plurality of sets of amplicons of the at least 22 Y-STR markers. In some embodiments of the method, a set of amplification primers of the alleles of at least 23 Y-STR markers are provided, wherein at least 5 of the Y-STR markers are rapidly mutating loci. In yet other embodiments, a set of amplification primers of the alleles of 27 Y-STR markers are provided, wherein at least 5 of the Y-STR markers are rapidly mutating loci. In some embodiments, the 27 Y-STR markers include 2 Y-STR markers having double copy markers contributing to the total number of Y-STR markers. In some embodiments, each set of the amplicons of at least 11 of the at least 22 Y-STR markers has a base pair size less than about 220 base pairs. In other embodiments, each set of the amplicons of at least 11 of at least 23 Y-STR markers has a base pair size less than about 220 base pairs. In yet other embodiments, each set of the amplicons of at least 11 of 27 Y-STR markers has a base pair size less than about 220 base pairs. In various embodiments of the method, a set of amplification primers including primers for the amplification of the alleles of at least 22 Y-STR markers are provided, wherein at least 6 of the Y-STR markers are rapidly mutating loci. In various embodiments of the method, a set of amplification primers including primers for the amplification of the alleles of at least 22 Y-STR markers are provided, wherein at least 7 of the Y-STR markers are rapidly mutating loci. The method may further include the step of detecting each set of amplicons whereby the alleles of at least 22 Y-STR markers are identified. In some embodiments, the alleles of at least 23 Y-STR markers are identified. In yet other embodiments, the alleles of 27 Y-STR markers are identified. In some embodiments, the detecting step is a fluorescence detection step. In some embodiments, the detecting step is performed by separating the plurality of sets of amplicons using a mobility dependent analysis, where the plurality of sets of amplicons is fluorescently labeled. In other embodiments, the detecting step does not detect fluorescence. In embodiments, when detecting steps do not detect fluorescence, the detecting step may include ion semiconductor detection, pyrophosphate release detection, or mass spectrometry detection. In some embodiments, the at least 11 Y-STR markers having amplicons having a base pair size of less than about 220 base pairs are DYS576, DYS389I, DYS460, DYS458, DYS19, DYS456, DYS390, DYS570, DYS437, DYS393, and DYS439. In some the embodiments, the at least 5 rapidly mutating Y-STR markers are selected from the group consisting of DYF387S1ab, DYS449, DYS518, DYS570, DYS576, and DYS627. In other embodiments, the at least 5 rapidly mutating Y-STR markers are 6 rapidly mutating Y-STR markers.

A method of male individual identification, including the steps of: contacting a sample containing a nucleic acid of a human male with a set of amplification primers including primers for the amplification of the alleles of at least 11 Y-STR markers; and amplifying the sample thereby forming a plurality of sets of amplicons of the at least 11 Y-STR markers where each set of the amplicons has a base pair size less than about 220 base pairs; and detecting each set of amplicons whereby the alleles of the male individual are identified. In various embodiments of the methods, the set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the step of amplifying the at least 11 Y-STR markers, may include amplifying at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments of the method, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, the method includes a set of amplification primers for the amplification of the alleles of more than 1 Y-STR markers. In other embodiments, the plurality of sets of amplicons of the more than 11 Y-STR markers where the plurality of sets of the amplicons has a base pair size less than about 410 base pairs. In some embodiments, the detecting step is a fluorescence detection step. In some embodiments, the method further includes the step of comparing the alleles identified for a first male individual to the alleles identified for a second male individual, whereby the first male individual is differentiable from the second male individual. In some embodiments, the first male individual has a similar paternal genetic lineage as the second male individual.

Kits. In some embodiments, the present teachings are directed to kits for analyzing a short tandem repeat sequence from a nucleic acid sample that utilize the methods described above. In some embodiments, a kit for analyzing a short tandem repeat sequence in a nucleic acid sample includes at least one receptacle containing a set of primers configured to hybridize to Y-STR markers. The kit may include primers for the amplification of at least 11 Y-STR markers where the primers are configured to provide each set of amplicons of the at least 11 Y-STR markers having a base pair size less than about 220 base pairs; and optionally, a size standard. In some embodiments, the kit may further include primers for the amplification of at least 5 Y-STR markers where the primers are configured to provide each set of amplicons of the at least 5 Y-STR markers having a base pair size greater than about 220 base pairs. The kit may include an amplification primer set for 25 Y-STR markers. In various embodiments, when the set of amplification primers amplify more than 11 Y-STR markers, then the set of amplification primers may be configured to provide all of the sets of amplicons of the more than 11 Y-STR markers having a base pair size less than about 410 base pairs. In various embodiments, when the set of amplification primers amplify more than 11 Y-STR markers, then the set of amplification primers may be configured to provide all of the sets of amplicons of the more than 11 Y-STR markers having a base pair size less than about 420 base pairs. In some embodiments, the kit may include a set of amplification primers labeled with one of at least 5 fluorescent dyes. The at least 5 fluorescent dyes used to label the primers of the kit may be configured to be spectrally distinct. The kit may further include at least one amplification primer that includes a mobility modifier. In some embodiments, the kit including a set of amplification primers amplifying at least 11 Y-STR markers, may amplify DYS576, DYS389I, DYS460, DYS458, DYS19, DYS456, DYS390, DYS570, DYS437, DYS393, and DYS439. In other embodiments, the kit including a set of amplification primers amplifying the at least 11 Y-STR markers, where the primers are configured to provide each set of amplicons of the at least 11 Y-STR markers having a base pair size less than about 220 base pairs, may amplify at least 5 Y-STR markers which are rapidly mutating loci. In some embodiments, the at least 5 rapidly mutating Y-STR markers may include DYF387S1ab, DYS449, DYS570, DYS576, and DYS627. In other embodiments, the at least 5 rapidly mutating Y-STR markers may further include DYS518. In some embodiments, the kit including a set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS518, DYS533, DYS570, DYS576, DYS627, DYS635, and Y-GATA-H4. In other embodiments, the kit including a set of primers for the amplification of at least 11 Y-STR markers may be a set of primers for the amplification of DYF387S1ab, DYS19, DYS385ab, DYS389I, DYS389II, DYS390, DYS391, DYS392, DYS393, DYS460, DYS437, DYS438, DYS439, DYS448, DYS449, DYS456, DYS458, DYS481, DYS533, DYS570, DYS576, DYS627, DYS635, DYS643, and Y-GATA-H4. In some embodiments, the kit includes a size standard. In various embodiments, the kit further includes an allelic ladder.

In another aspect, a kit for co-amplifying a set of loci of at least one DNA sample may be provided, including a set of amplification primers for the amplification of at least 22 Y-STR markers where at least 5 of the Y-STR markers are rapidly mutating loci; and optionally, a size standard. In some embodiments, the size standard is an allelic ladder. In some embodiments, the at least 5 rapidly mutating Y-STR markers of the kit include DYF387S1ab, DYS449, DYS570, DYS576, and DYS627. In some embodiments, the at least 5 rapidly mutating Y-STR markers include DYS518. In some embodiments, the set of amplification primers is labeled with one of at least 5 fluorescent dyes. The set of amplification primers of the kit for the amplification of at least 22 Y-STR markers may be configured to provide at least one set of amplicons of the Y-STR markers where the at least one set of amplicons includes a mobility modifier. In some embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS570, DYS576, DYS627, DYS635, and Y-GATA-H4. In other embodiments, the at least 22 Y-STR markers may include DYF387S1ab, DYS19, DYS385ab, DYS389I, DYS389II, DYS390, DYS391, DYS392, DYS393, DYS437, DYS438, DYS439, DYS448, DYS449, DYS456, DYS458, DYS518, DYS570, DYS576, DYS627, DYS635, and Y-GATA-H4.

In some embodiments, a sufficient quantity of enzyme for amplification, amplification buffer to facilitate the amplification, a divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use may be included in the kits of the invention in any combination or selection. The amounts of the various reagents in the kits also can be varied depending upon a number of factors, such as the optimum sensitivity of the process. It is within the scope of these teachings to provide test kits for use in manual applications or test kits for use with automated sample preparation, reaction set-up, detectors or analyzers. Those in the art understand that the detection techniques employed are generally not limiting. Rather, a wide variety of detection means are within the scope of the disclosed methods and kits, provided that they allow the presence or absence of an amplicon to be determined.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

Aspects of the present teachings may be further understood in light of the following examples, which should not be construed as limiting the scope of the present teachings in any way.

EXAMPLES

Those having ordinary skill in the art will understand that many modifications, alternatives, and equivalents are possible. All such modifications, alternatives, and equivalents are intended to be encompassed herein.

The following procedures are representative of reagents and procedures that can be employed for the isolation and amplification of a target nucleic acid in a sample and the detection, identification and analysis of short tandem repeat sequences on the Y chromosome.

PCR Assay Set-Up and Reaction Conditions.

The primer sets of Panels 1-7 are prepared as described above and dye-labeled and unlabeled primers in buffer (low EDTA buffer containing 10 mM Tris-HCL, pH 8.0, and 0.1 mM EDTA, pH 8.0) are amplified in PCR reactions as follows:

1 ng input DNA, typically, is used.
Add 10 µL Master Mix which includes polymerase enzyme.
Add 5 µL primer set.
Mix thoroughly by vortexing at medium speed for 10 sec.
  Centrifuge briefly to remove any liquid from the cap of the tube.
Add 15 µL of the PCR reaction mixture to each reaction well or tube.
Centrifuge plate or tubes at 3000 rpm for about 30 sec to remove any bubbles prior to amplification.
Amplify in GeneAmp® PCR System 9700 thermocycler or Venti® 96-well Thermal Cycler, for 26-30 cycles, using the following sequence: hold at 95° C. for 1 min; denature at 94° C. for 4 sec; anneal/extend at 61° C. for 1 min; final extension at 60° C. for 10 min; and hold at 4° C. for storage or until analysis. Samples run using Yfiler® primer sets are prepared and amplified according to the AmpFlSTR® Yfiler® PCR Amplification Kit User's Guide (Part no. 4359513).

Capillary Electrophoresis Sample Preparation and Detection. The amplified samples are analyzed by methods that resolve amplification product size and/or sequence differences as would be known to one of skill in the art. For example, capillary electrophoresis can be used following the instrument manufactures directions. Briefly, 0.5 µL GeneScan™_600 LIZ™ Size Standard and 9.5 µL of Hi-Di™ Formamide are mixed for each sample to be analyzed. 10.0 µL of the Formamide/GeneScan-600 LIZ solution is dispensed into each well of a MicroAmp® Optical 96-well reaction plate to which a 1.0 µL aliquot of the PCR amplified sample or allelic ladder is added and the plate is covered. The plate is briefly centrifuged to mix the contents and collect them at the bottom of the plate. The plate is heated at 95° C. for 3 min to heat-denature the samples and then quenched immediately by placing on ice for 3 min.

Capillary Electrophoresis Methods and Analysis. Capillary electrophoresis (CE) was performed on current Applied Biosystems instruments: the Applied Biosystems 3500 xl Genetic Analyzer using the specified J6 variable binning module as described in the instrument's User's Guide. The 3500 xl Genetic Analyzer's parameters were: sample injection for 24 sec at 1.2 kV and electrophoresis at 15 kV for 1550 sec in Performance Optimized Polymer (POP-4™ polymer) with a run temperature of 60° C. as indicated in the HID36_POP4xl_G5_NT3200 protocol. Variations in instrument parameters, e.g. injection conditions, were different on other CE instruments such as the 3500, 3130xl, or 3130 Genetic Analyzers.) The data were collected using versions of the Applied Biosystems Data Collection Software specific to the different instruments, such as v.3.0 for the 3130xl and 3500 Data Collection Software v.1.0, was analyzed using GeneMapper ID-X vi.2.

Following instrument set-up according to the manufacturer's directions each sample is injected and analyzed by appropriate software, e.g., GeneMapper® ID-Xv1.2 software with the standard analysis settings. A peak amplitude of 175 RFU (relative fluorescence units) was used as the peak detection threshold.

Figure 16:
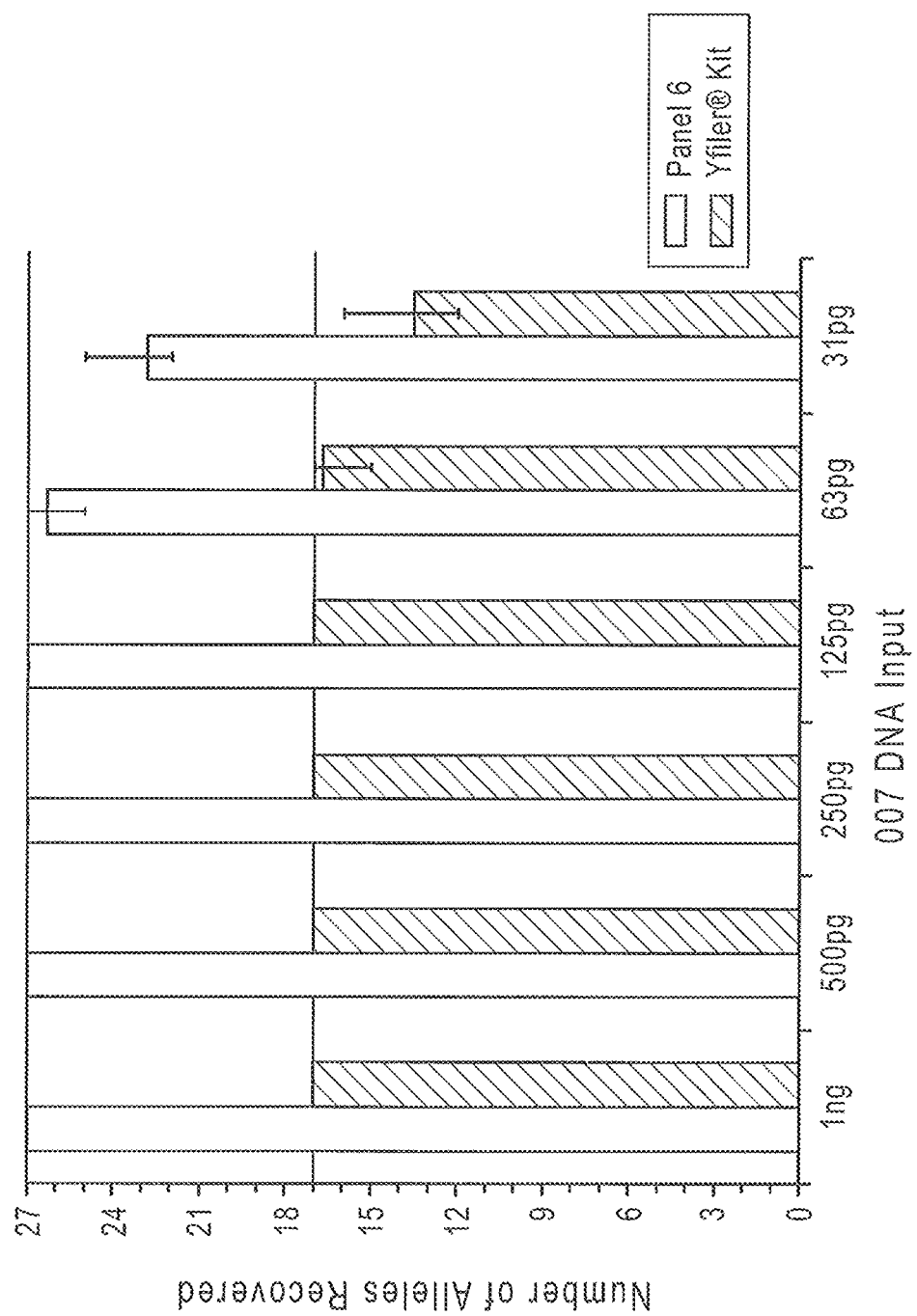
FIG. 16 is a graphical representation comparing the number of alleles recovered from PCR amplifications using Y-STR Panel 6 and Yfiler®, as decreasing amounts of target DNA are used.

Example 1: Sensitivity study. The effect of decreasing target male DNA is compared, using the Panel 6 multiplex or the Yfiler® multiplex, as shown in FIG. 16. The DNA input is varied from 1 ng, 500 pg, 250 pg, 63 pg, and 31 pg, with N=6. The Y filer multiplex begins to suffer allelic dropout at 63 pg. While there are some losses using the Panel 6 multiplex, the overall robustness of identification is higher because Panel 6 has 27 alleles vs. Yfiler®'s 17. More reliable identification is possible using Panel 6 multiplex at lower concentrations of target male DNA.

Figure 17:
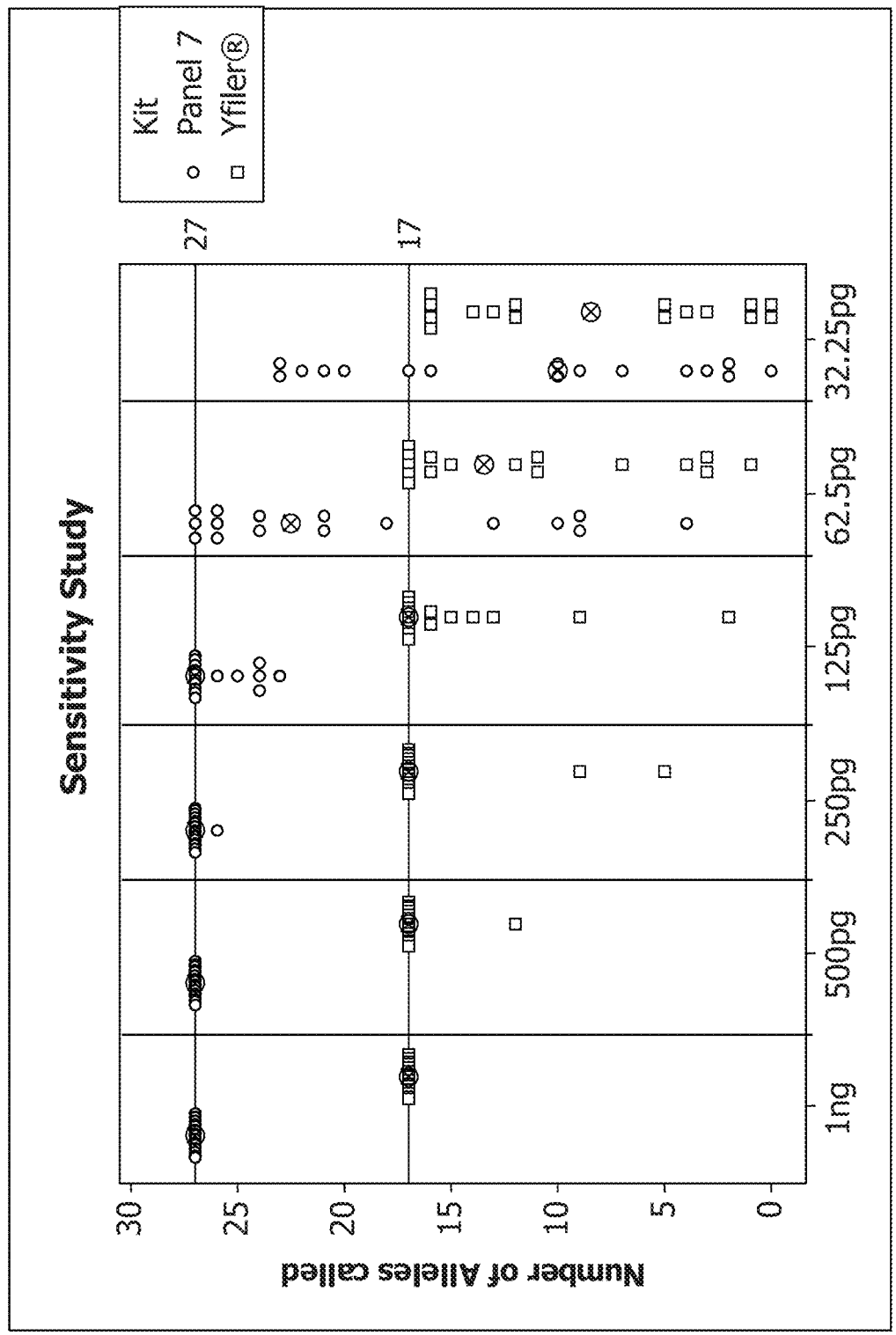
FIG. 17 is a graphical representation comparing the number of alleles recovered from PCR amplifications using Y-STR Panel 7 and Yfiler®, as decreasing amounts of target DNA are used.

Example 2: Sensitivity study. The effect of decreasing target male DNA is compared, using the Panel 7 multiplex or the Yfiler® multiplex, as shown in FIG. 17. The data shown is collected from four different test sites, each performing N-4 replications. The DNA input is varied from 1 ng, 500 pg, 250 pg, 62.5 pg, and 32.25 pg. The average number of alleles identified at each concentration for each multiplex is indicated by the crosshatched circle symbol. The Y filer multiplex begins to suffer allelic dropout at 63 pg. While there are some losses using the Panel 7 multiplex, the overall robustness of identification is higher because Panel 7 has 27 alleles vs. Yfiler®'s 17. More reliable identification is possible using Panel 7 multiplex at lower concentrations of target male DNA.

Figure 18:
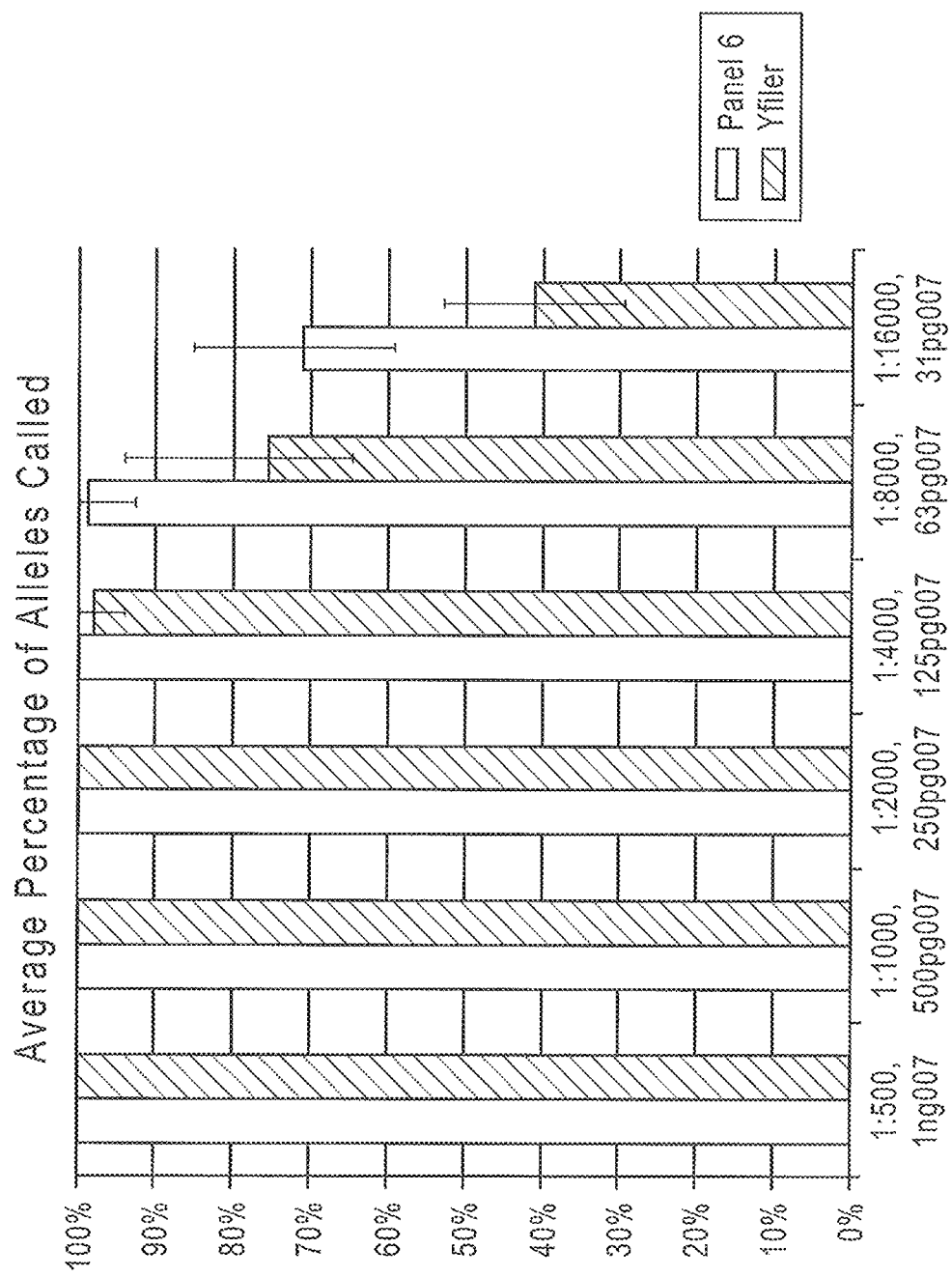
FIG. 18 is a graphical representation comparing the percentage of alleles identified using the Y-STR Panel 6 and Yfiler® multiplexes as the ratio of male to female DNA decreases, using a constant concentration of female DNA.

Example 3: The effect of using male/female DNA mixtures as input DNA is compared, using the Panel 6 multiplex or the Yfiler® multiplex, as shown in FIG. 18. As male DNA input is decreased (1 ng, 500 pg, 250 pg, 125 pg, 63 pg, to 31 pg), in the presence of constant female DNA input of 500 ng, with N=6. The Panel 6 multiplex recovers a higher percentage of alleles than the Yfiler® multiplex recovers. Even at 31 pg of male target DNA, over 70% of alleles of the Panel 6 multiplex are identified.

Figure 19:
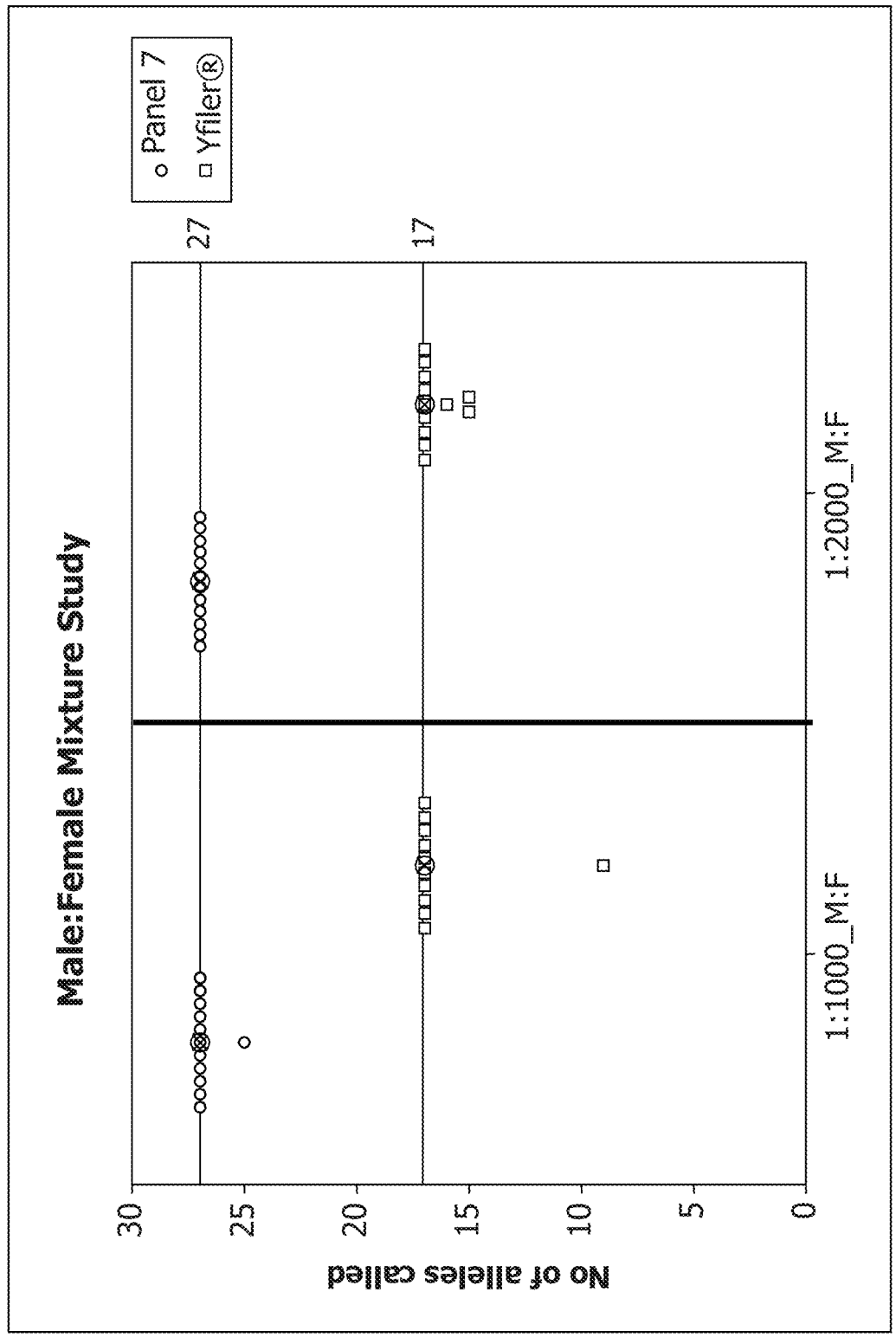
FIG. 19 is a graphical representation comparing the percentage of alleles identified using the Y-STR Panel 7 and Yfiler® multiplexes as the ratio of male to female DNA decreases, using a constant concentration of female DNA.

Example 4: The effect of using male/female DNA mixtures as input DNA is compared, using the Panel 7 multiplex or the Yfiler® multiplex, as shown in FIG. 19. The data shows results from a total of four test sites, where male DNA input is decreased from 1 ng to 0.5 ng (M007) in the presence of constant female DNA input of 1 ug (F9947), with N=3. The left panel shows the results for the 1 ng M007/1 ug F9947 and the right panel shows the results for 0.5 ng/1 ug F9947 for both Panel 7 and Yfiler® multiplexes, with averages for each multiples shown by a crosshatched circle. The Panel 7 multiplex recovers a higher percentage of alleles than the Yfiler® multiplex recovers. Even at a 1:2000 ratio of male:female, all alleles of the Panel 7 multiplex are identified.

Figure 20:
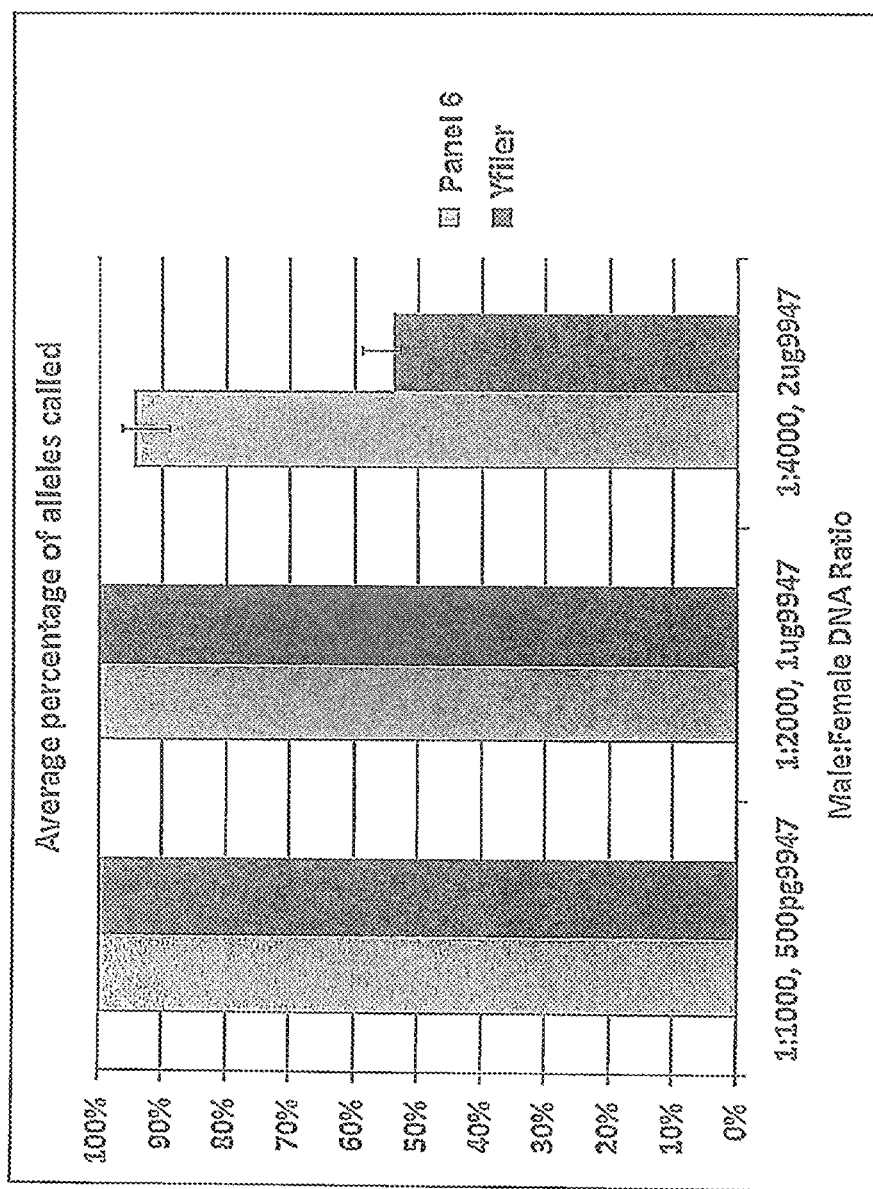
FIG. 20 is a graphical representation comparing the percentage of alleles identified using the Y-STR Panel 6 and Yfiler® multiplexes as the ratio of male to female DNA decreases, using an increasing concentration of female DNA.

Example 5: The effect of using male/female DNA mixtures as input DNA is compared, using the Panel 6 multiplex or the Yfiler® multiplex, as shown in FIG. 20. As male target DNA input is held constant at 500 pg, female DNA is increased from 500 ng, to 1 µg, to 2 µg, with N=6. At the highest concentration of female DNA, over 90% of alleles in the Panel 6 multiplex are identified whereas less than 60% of alleles are identified in the Yfiler® multiplex.

Figure 21:
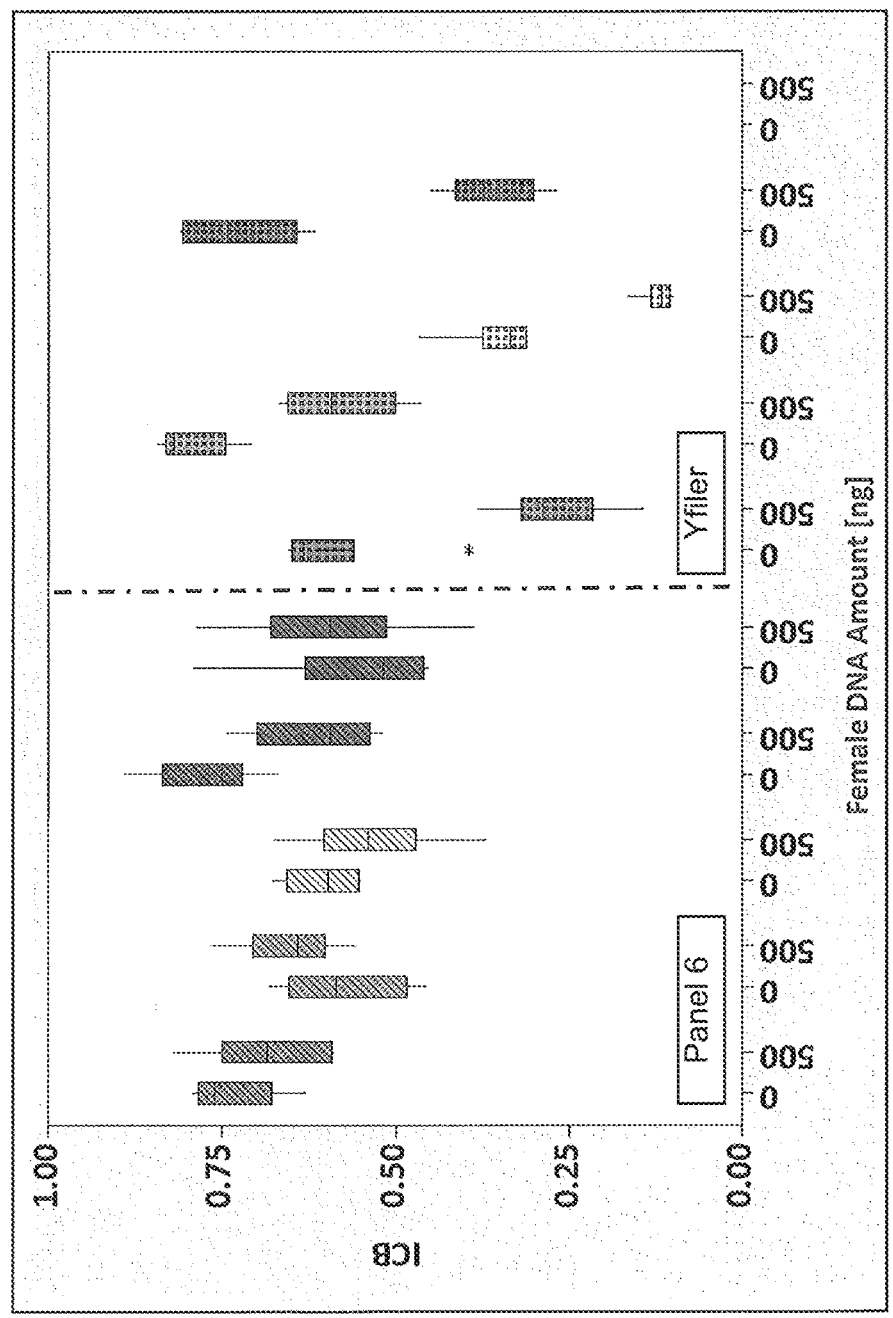
FIG. 21 is a graphical representation of the comparison of the intracolor balance when using Panel 6 multiplex or the Yfiler® multiplex.

Example 6: Intracolor balance in male/female mixtures is compared, using the Panel 6 multiplex or Yfiler® multiplex, as shown in FIG. 21. Male target DNA input is held constant (500 pg) and female DNA concentration is varied from 0.0 ng to 500 ng, for each of the five dye channels containing alleles of the multiplex, with N=6. Intracolor peak balance (ICB) is calculated by dividing the lowest peak height by the highest peak height within a color, i.e., all the markers labeled with the same fluorophore and detectable in the same wavelength region. An ICB value of 1 would mean that all the alleles labeled with the same fluorophore have completely uniform peak heights, and any improvement of the ICB ratio towards a value of 1 may offer higher accuracy in identifying the presence of a particular allele. As shown in FIG. 21, Panel 6 multiplex is significantly less affected than the Yfiler® multiplex by the presence of female DNA, having ICB values consistently greater than about 0.50. Additionally, all five dye channels behave more similarly to each other than that of the Yfiler® multiplex.

Figure 22:
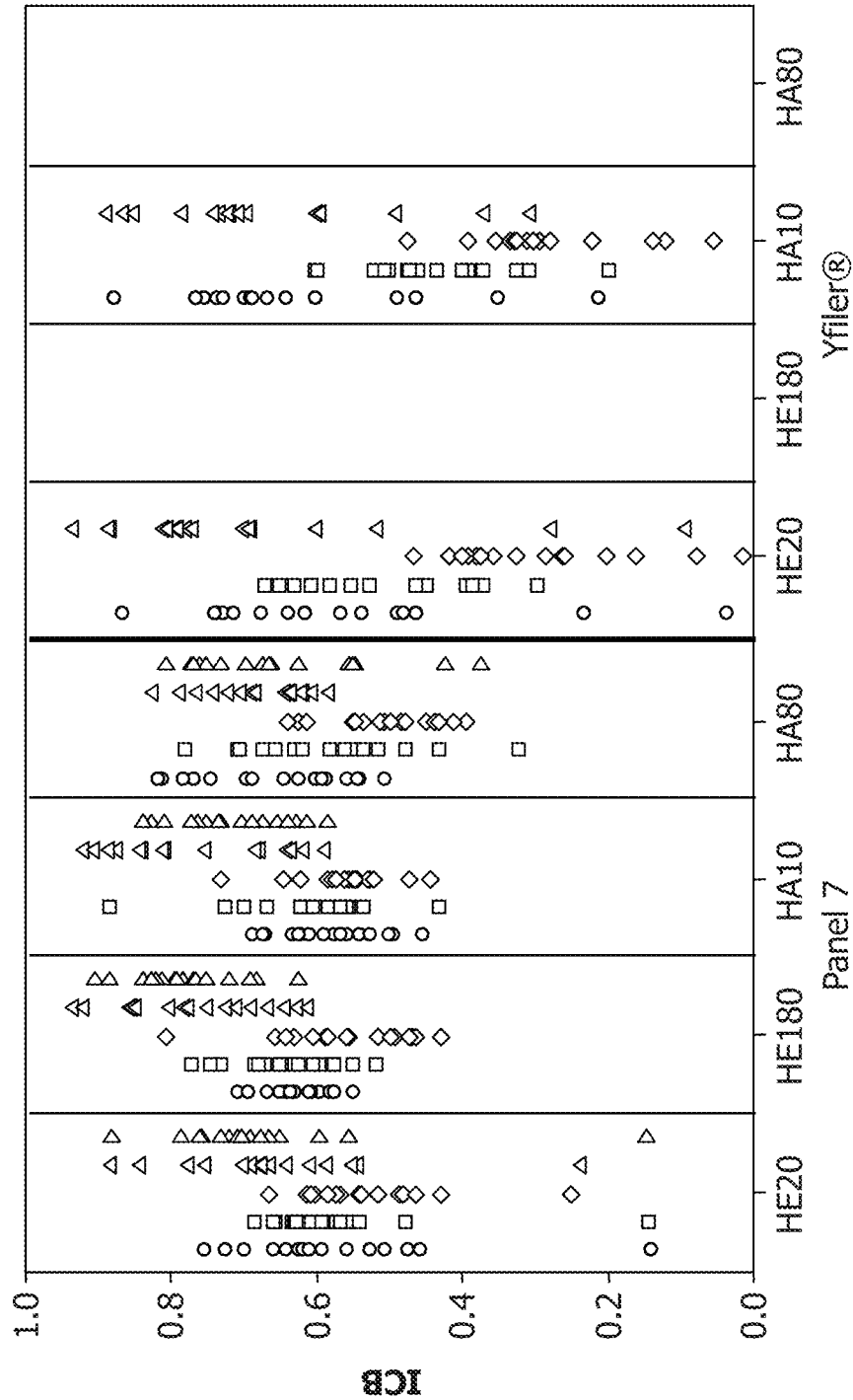
FIG. 22 is a graphical representation of the comparison of the intracolor balance when using Panel 7 multiplex or the Yfiler® multiplex, at two different ratios of male:female DNA.

Example 7: Intracolor balance in male/female mixtures is compared, using the Panel 7 multiplex or Yfiler® multiplex, as shown in FIG. 22. The two panels on the left side of the figure represents, in the first column: Male target DNA M007 at 1 ng and female DNA F9947 at 1 ug (1:1000 M:F) and in the second column: Male target DNA M007 at 500 pg and female DNA F9947 at 1 ug (1:2000 M:F), for each of the five dye channels (●, ■, ◇, ▲, and ▶) containing alleles of the Panel 7 multiplex, from a total of 4 test sites, each with N=3. The two panels on the right side of the figure represents, in the first column: Male target DNA M007 at 1 ng and female DNA F9947 at 1 ug (1:1000 M:F) and in column 2: Male target DNA M007 at 500 pg and female DNA F9947 at 1 ug (1:2000 M:F), for each of the four dye channels (●, ■, ◇, and ▲) containing alleles of the Yfiler® multiplex, from a total of 4 test sites, each with N=3. Intracolor peak balance (ICB) is calculated and defined as described in Example 6. As shown in FIG. 22, Panel 6 multiplex is significantly less affected than the Yfiler® multiplex by the presence of female DNA.

Figure 23:
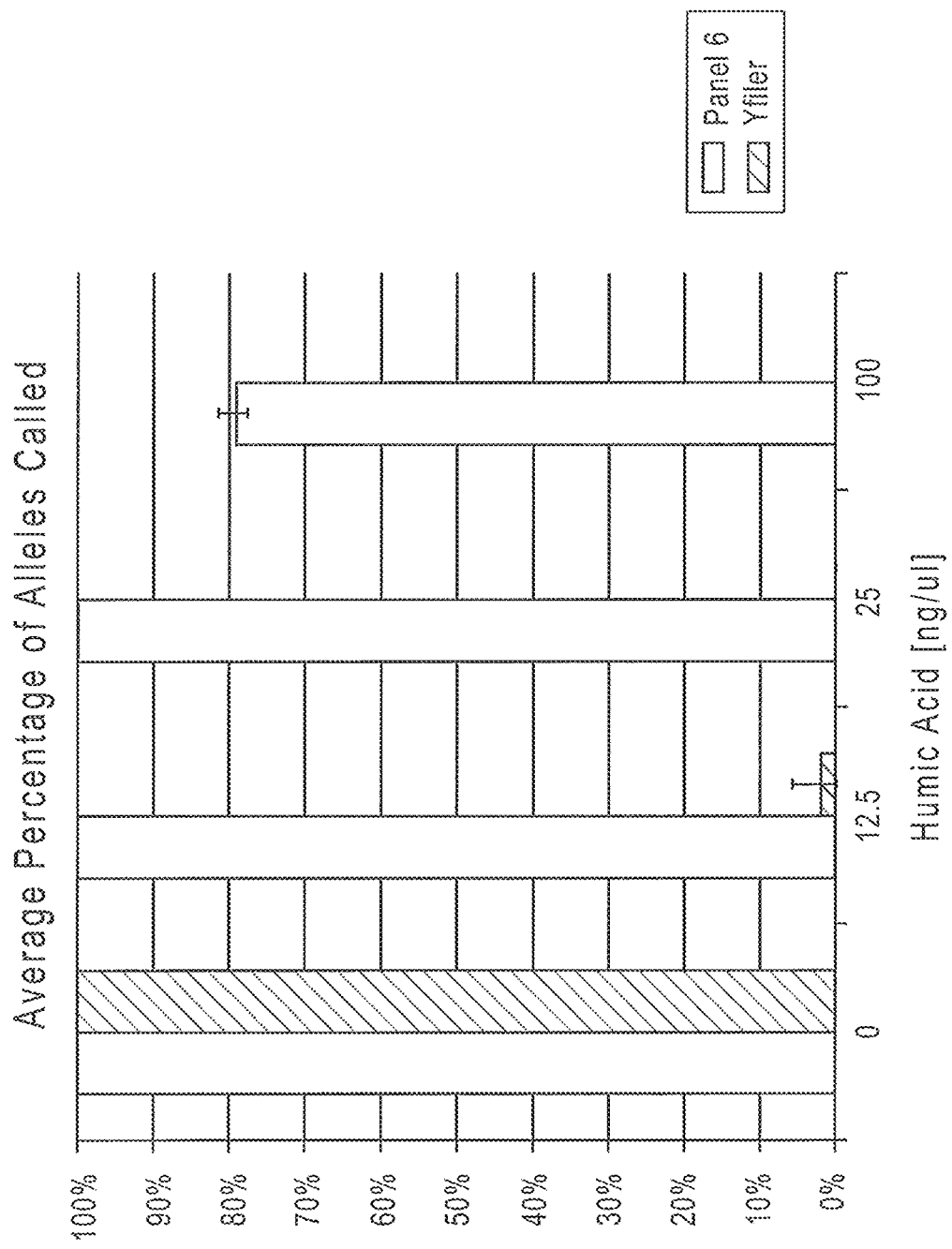
FIG. 23 is a graphical representation of the comparison of the average percentage of alleles identified using the Y-STR Panel 6 or Yfiler® multiplexes when amplifying target DNA in the presence of increasing amounts of humic acid.

Example 8: Recovery of alleles in the presence of humic acid, an inhibitor of PCR are compared, using the Panel 6 multiplex or the Yfiler® multiplex, as shown in FIG. 23. Male target DNA input is held constant at 500 pg, and the concentration of humic acid is increased from 0.0 ng/µl, 12.5 ng/µl, 25 ng/µl, and 100 ng/µl, using N=6. As the concentration of humic acid is raised to 12.5 ng/µl or higher, the recovery of alleles using the Yfiler® mulitiplex is severely inhibited. The use of the Panel 6 multiplex permits recovery of nearly 80% of the alleles even at the highest concentration of humic acid in the amplification reaction.

Figure 24:
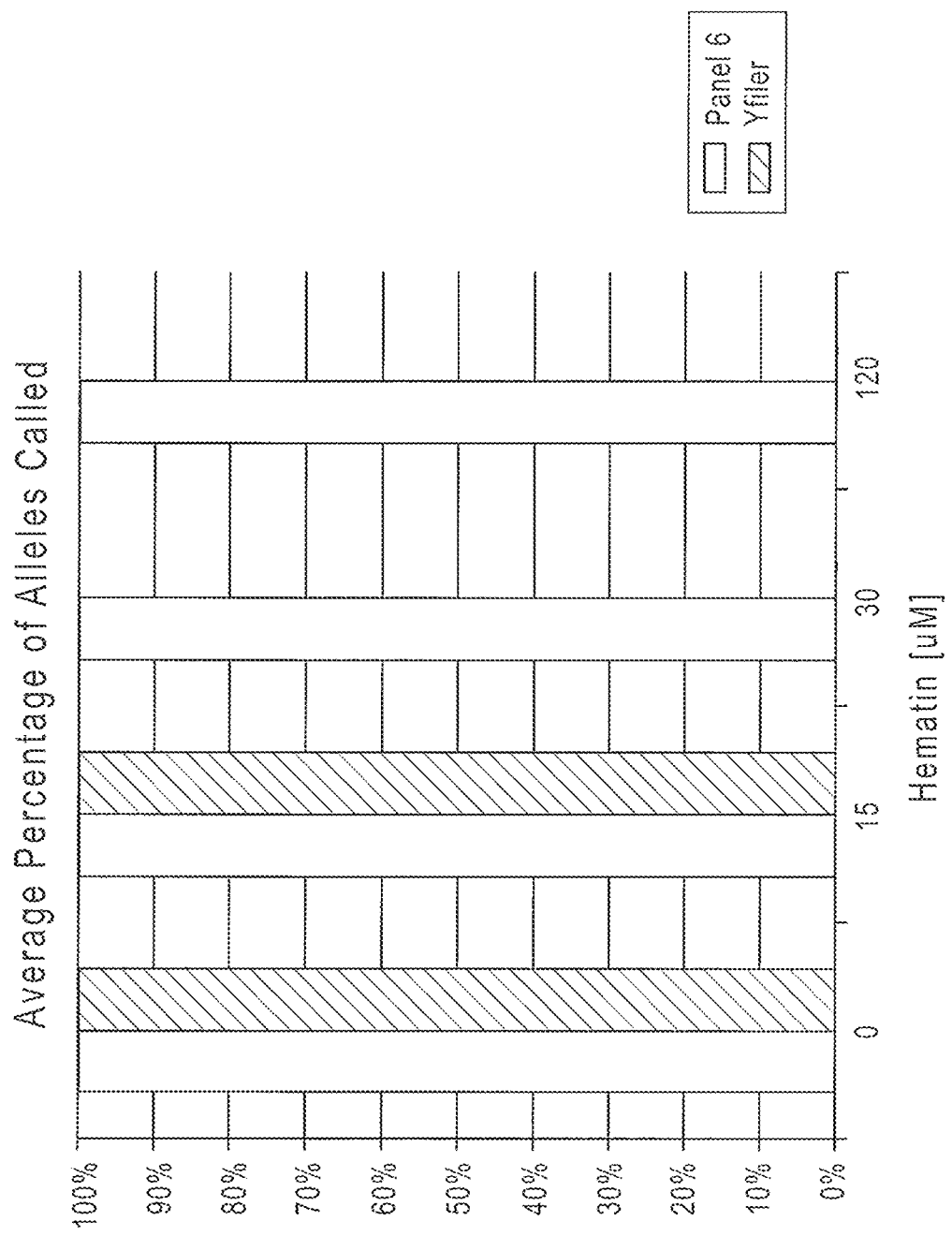
FIG. 24 is a graphical representation of the comparison of the average percentage of alleles identified using the Y-STR Panel 6 or Yfiler® multiplexes when amplifying target DNA in the presence of increasing amounts of Hematin.

Example 9: Recovery of alleles in the presence of hematin, an inhibitor of PCR are compared, using the Panel 6 multiplex or the Yfiler® multiplex, as shown in FIG. 24. Male target DNA input is held constant at 500 pg, and the concentration of hematin is increased from 0.0 µM, 15 µM, 30 µM, and 120 µM, using N=6. As the concentration of hematin is raised to 30 µM or higher, the recovery of alleles using the Yfiler® mulitiplex is blocked completely. The use of the Panel 6 multiplex permits recovery of all of the alleles even at the highest concentration of hematin in the amplification reaction.

Figure 25:
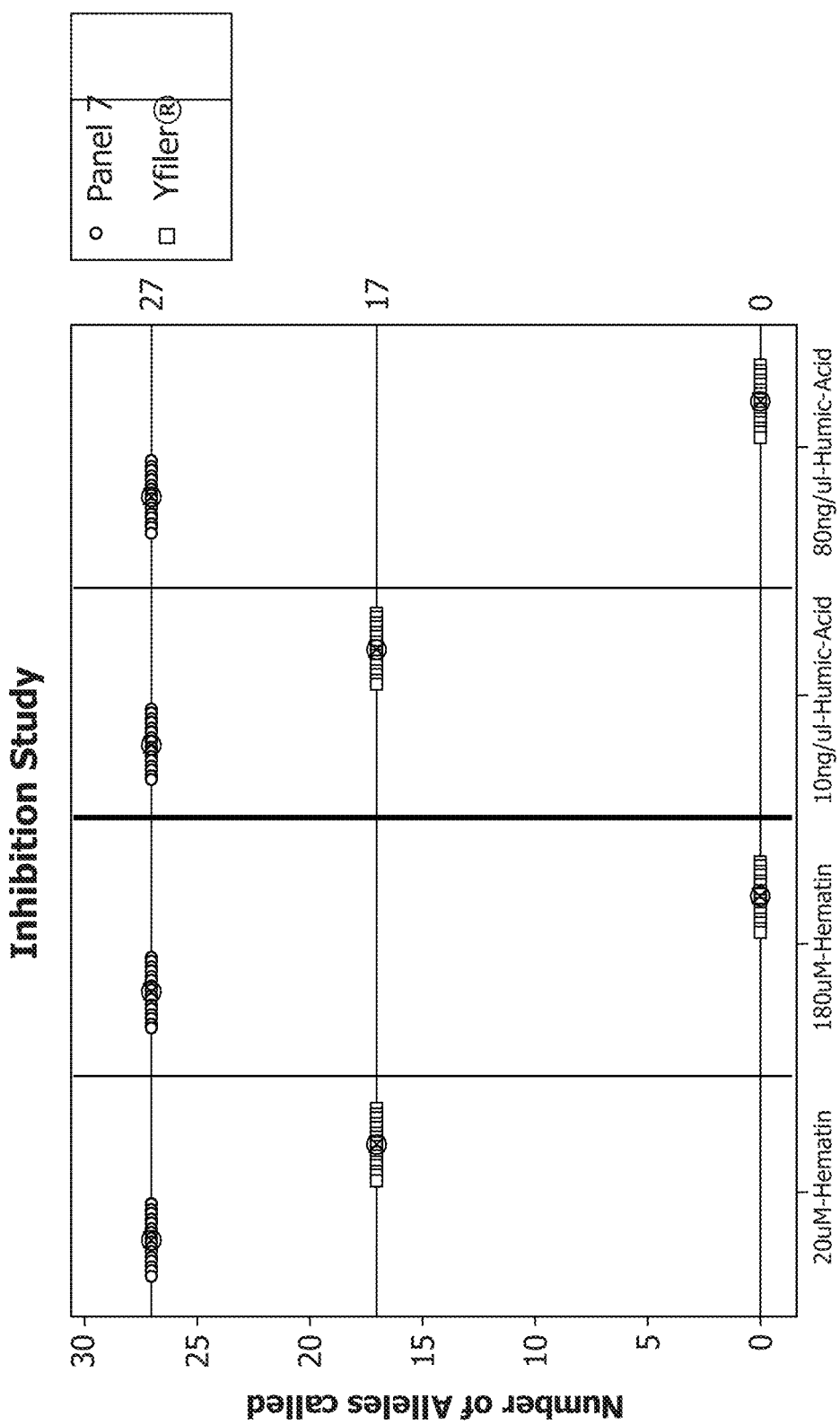
FIG. 25 is a graphical representation of the comparison of the average percentage of alleles identified using the Y-STR Panel 7 or Yfiler® multiplexes when amplifying target DNA in the presence of increasing amounts of Hematin or Humic acid.
Figure 26:
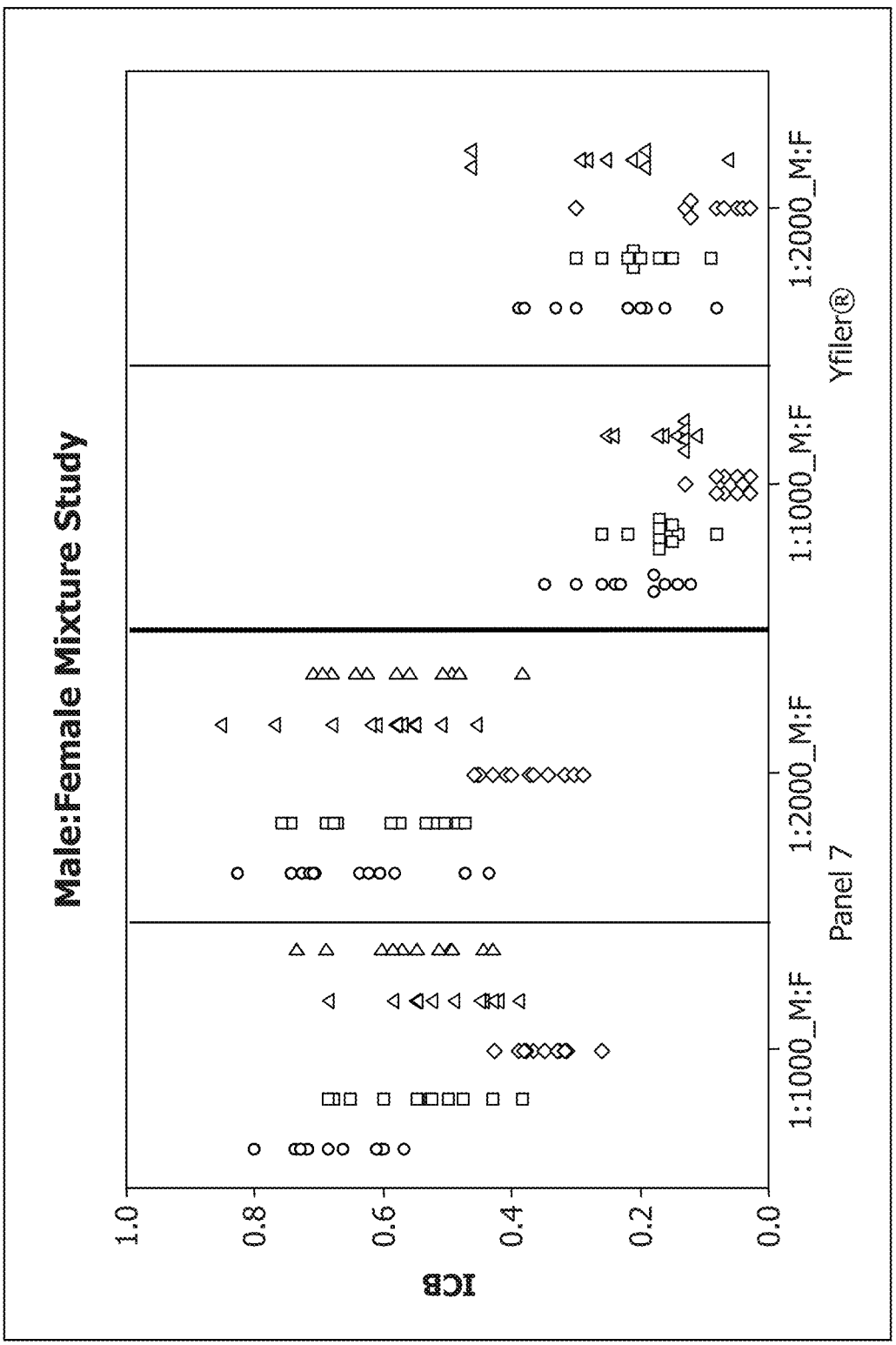
FIG. 26 is a graphical representation of the comparison of the intracolor balance for Panel 7 or Yfiler® multiplexes when analysis is performed in the presence of two different concentrations of hematin or humic acid.

Example 10: Recovery of alleles in the presence of hematin, an inhibitor of PCR, or in the presence of humic acid, are compared using the Panel 7 multiplex or the Yfiler® multiplex, as shown in FIG. 25. Male target DNA input is held constant at 1 ng, and hematin is present at 20 µM (column 1); hematin is present at 180 µM (column 2); humic acid is present at 10 ng/µl (column 3); or humic acid is present at 80 ng/µl (column 4) data from a total of four test sites each using N=4. As the concentration of hematin is raised to 180 µM or higher, the recovery of alleles using the Yfiler® multiplex is blocked completely. The use of the Panel 7 multiplex permits recovery of all of the alleles even at the highest concentration of hematin in the amplification reaction. At humic acid concentrations of 80 ng/ul, recovery of alleles using the Yfiler® multiplex is blocked completely, while the use of Panel 7 multiplex permits complete recovery. FIG. 26 shows the intracolor balance for each of the five dye channels (circle, square, diamond, ], and ▶) of this data. As can be seen for each of the two differing concentrations of hematin and humic acid, respectively, use of the Panel 7 multiplex provides more consistent results across all dye channels.

Figure 27:
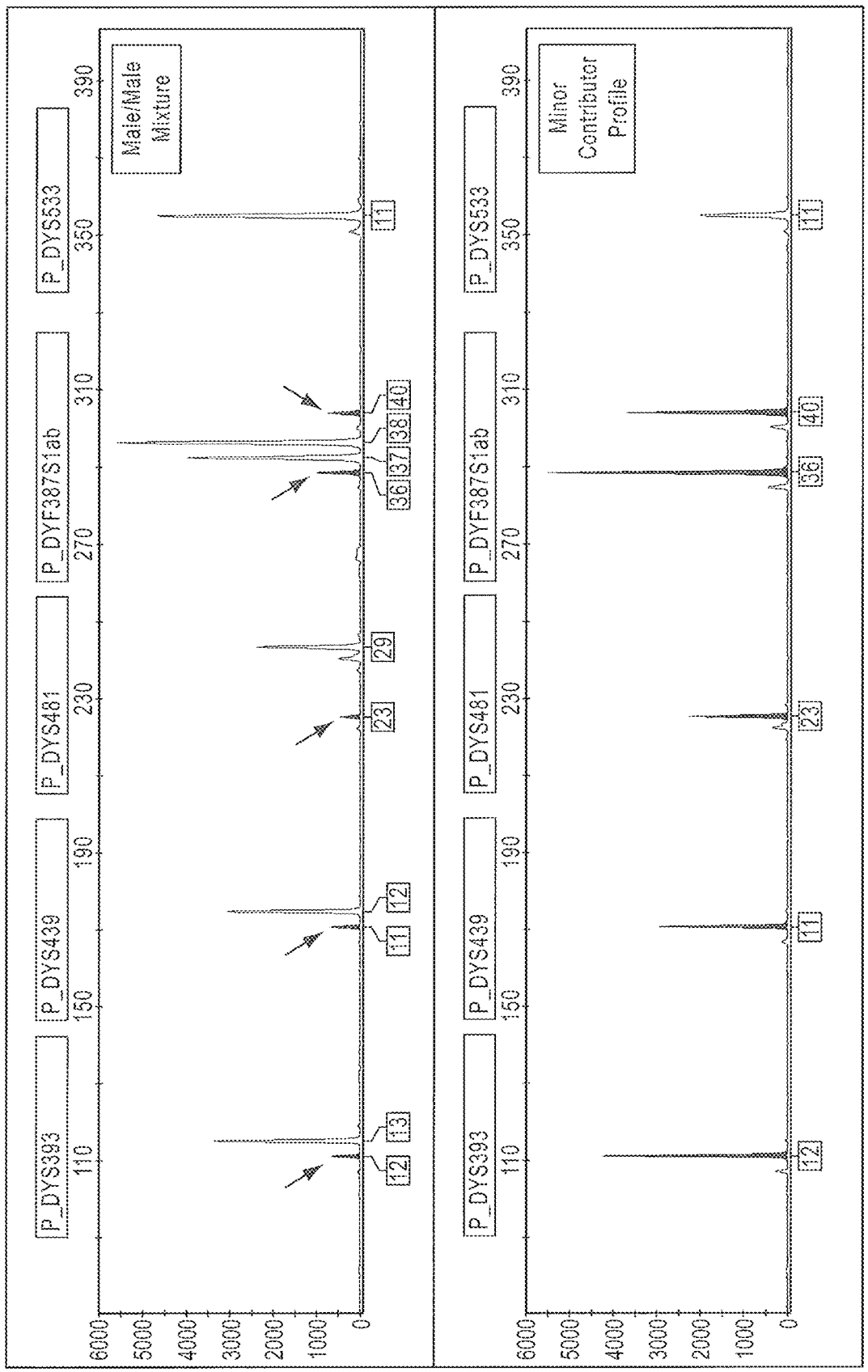
FIG. 27 is a graphical representation of an electropherogram showing the resolution of a Male/Male mixture using the Y-STR Panel 6 multiplex.

Example 11: The ability to identify a minor male contributor in a mixture of 2 male contributor target DNA samples is shown in FIG. 27. An 8:1 ratio of 437 pg:63 pg major: minor contributor is shown in the segment of the electropherogram shown. The upper trace shows the mixture, with arrows pointing to the alleles belonging to the minor male contributor. This is compared to the minor male contributor profile shown in the lower panel of FIG. 27, which was obtained without the presence of any other male DNA sample. The improved intracolor balance provided by the primers used in Panel 6 or Panel 7 yields improved uniformity of peak heights across an allele range, thus allowing improved identification of minor contributor alleles.

Figure 28:
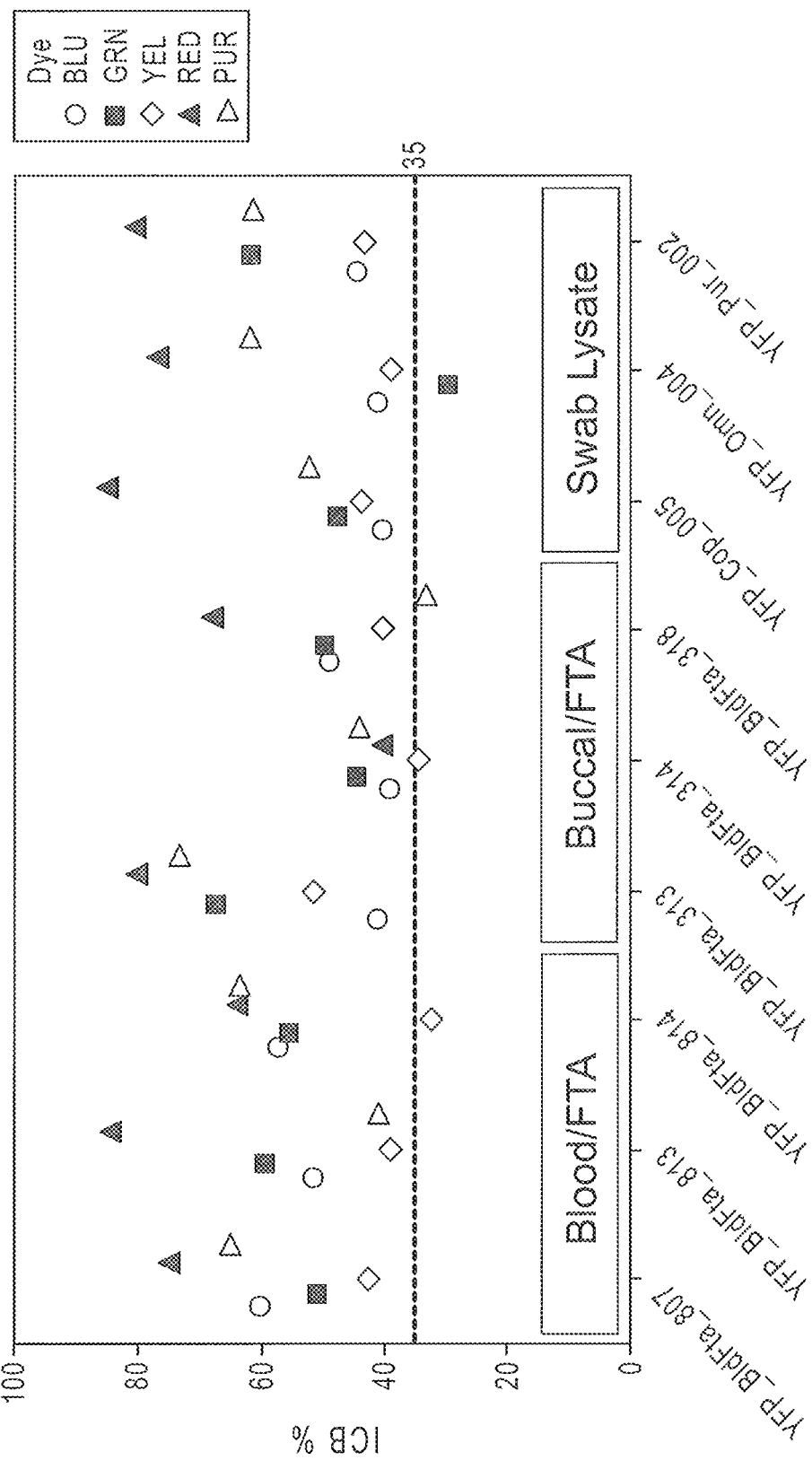
FIG. 28 is a graphical representation of the intracolor balance of electrophoretic signals provided by direct amplification of biological samples on selected substrates using the Panel 7 multiplex.
Figure 29:
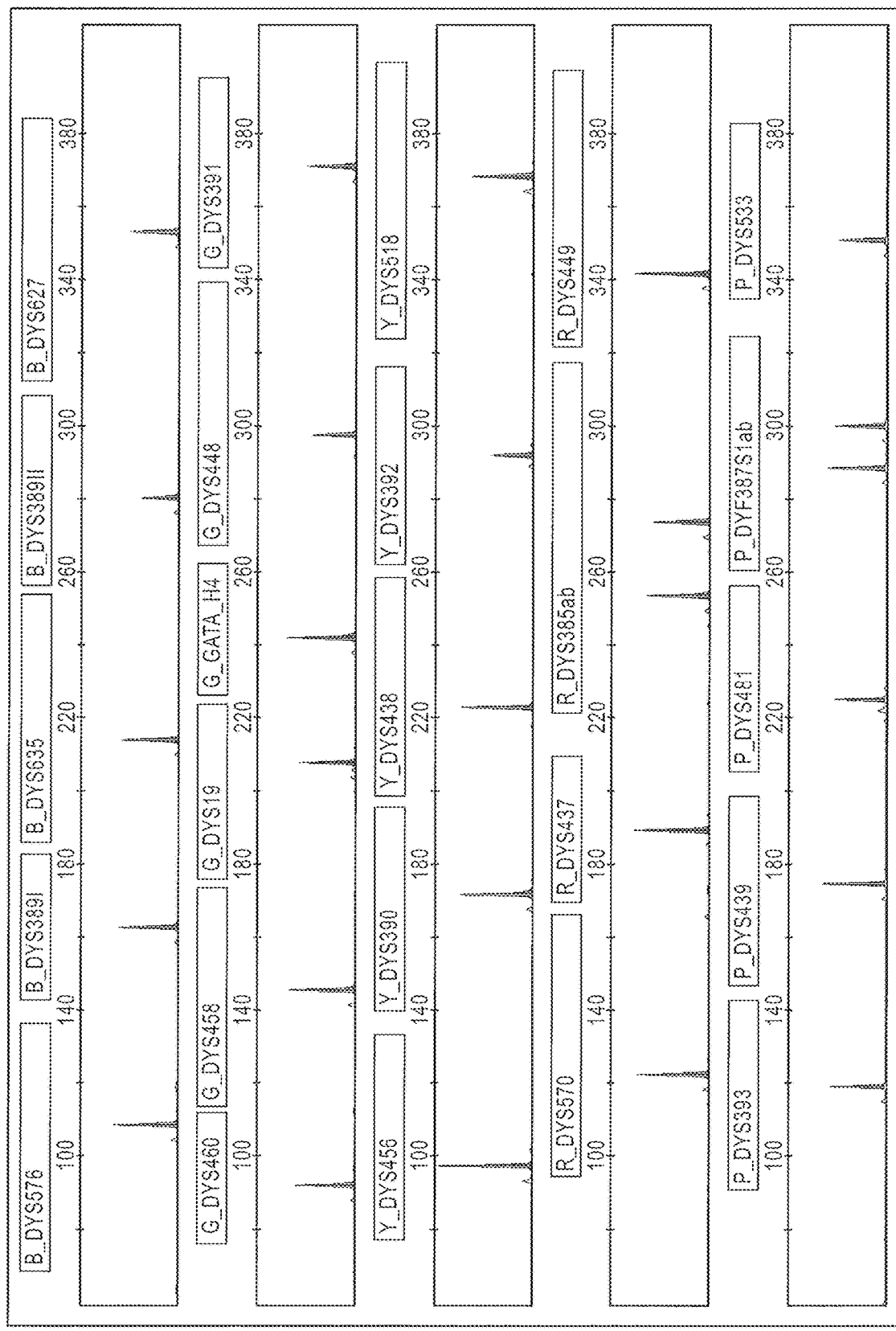
FIG. 29 is a graphical representation of an electropherogram of the amplification results of one of the directly amplified samples of FIG. 28.

Example 12: Direct Amplification. The primers directed to multiplex Panel 7 are used to directly amplify unprocessed biological samples. The sample types are blood collected on FTA paper (n=3); buccal sample on FTA paper (n=3); and swab lysate (3 different swab materials, all aged from about 6 months to about 1 year after collection). The primers used for loci in Panel 7 that are also present in Panel 6 have identical sequences, and therefore have equivalent performance. The Mastermix used for amplification is adapted for universal application. FIG. 28 shows the comparison of intracolor balance for each of the replicates of the three different sample/substrate types. The results show that the minimally required signal threshold of greater than 0.40 is achieved across all three sample/substrate types for direct amplification. FIG. 29 shows an electropherogram of the resulting Y-STR profile of one of the blood on FTA samples. For each color panel, full scale is 10,000 Rfus. It is shown that complete and unambiguous profiles are obtained with the direct amplification method.

Example 13. Father-Son Study. Fifty three father-son pairs are studied using the multiplex of Panel 7, Yfiler®, and another commercially available kit, Kit B. In Table 4, the results are presented. A number of mutations are identified, for which the total is shown in column 2, and the location of the mutation is shown in column 1. Empty cells in the table indicate where a mutation was not identified because that marker is not part of the panel. The total number of mutations/Kit represent the number of mutations identified overall for each kit. As can be seen, the Yfiler® multiplex can identify 4 mutations; Kit B can identify 5 mutations, and Panel 7 identifies 10 mutations overall. This greater resolution permits finer discrimination for males having the same genetic lineage, which may still provide random mutations despite a lack of recombination.

TABLE 4

Mutations found in the 53 father-son pairs for each multiplex panel.

| Marker | Number of mutations | Yfiler ® | Kit B | Panel 7 |
|---|---|---|---|---|
| DYF387S1[a] | 1 | | | 1 |
| DYS449[a] | 2 | | | 2 |
| DYS458 | 2 | 2 | 2 | 2 |
| DYS518[a] | 3 | | | 3 |
| DYS549 | 1 | | 1 | |
| Y-GATA-H4 | 2 | 2 | 2 | 2 |
| Total number of mutations/Kit | | 4 | 5 | 10 |

[a]This marker is a rapidly mutating Y-STR marker.

Example 14. Discrimination of Male Samples of differing genetic backgrounds. Over 700 male samples from a variety of genetic backgrounds are evaluated using Yfiler® and Panel 7 multiplex. The results are shown in TABLE 5a. While Yfiler® identifies a large percentage of individuals across a wide range of ethnic backgrounds; Panel 7 can identify a greater percentage, particularly in non-Caucasian groups.

TABLE 5a

Discrimination of Male Samples of Differing Genetic Backgrounds.

| Race | Total # mice samples* | # of unique Yfiler ® haplotypes | # of unique Panel 7 haplotypes |
|---|---|---|---|
| African American | 260 | 259 (99.6%) | 260 (100%) |
| Asian | 5 | 5 (100%) | 5 (100%) |
| Caucasian | 239 | 236 (98.7%) | 239 (100%) |
| Chinese | 1 | 1 | 1 |
| Hispanic | 195* | 193 (99.0%) | 194 (99.5%) |
| Korean | 53* | 52 (100%) | 52 (100%) |
| All | 753* | 741 (98.4%) | 750 (99.6%) |

*of potentially related individuals removed

Further screening of male samples with Yfiler® identified a set of 15 identical haplotypes. These identical haplotypes, including the potentially related individuals from TABLE 5a were reevaluated with the Panel 7 multiplex and the results are shown in TABLE 5b. Seven of the 15 identical Yfiler® haplotypes could be resolved. Four of the 15 identical Yfiler® haplotypes are potentially related; it is more difficult to resolve such haplotypes. Three of the identical Yfiler® haplotypes cannot be resolved using Panel 7, even though the individuals are potentially unrelated. However, Panel 7 multiplex can improve the rate of successfully resolving haplotype for individuals, including those of greater ethnic variety than previously seen in commercially available multiplex panels.

TABLE 5b

Discrimination of Identical Haplotypes.

| No. | Sample ID No. | Race | Panel 7 | Potentially related |
|---|---|---|---|---|
| 1 | 0590, 0976 | Caucasian, Hispanic | Full match (7/15 autosomal matches) | |
| 2 | 1153, 1175 | 2× Hispanic | Full match | yes |
| 3 | 0948, 0960 | 2× Hispanic | Full match with 6 deletions | yes |
| 4 | 0403, 0408 | 2× Caucasian | 6 mismatches | |
| 5 | 0326, 0945 | Caucasian, Hispanic | 5 mismatches | |
| 6 | 0550, 0824, 0891 | Caucasian, 2× Hispanic | 3 mismatches resulted in 3 haplotypes | |
| 7 | 0627, 0507 | 2× Caucasian | 1 mismatch at DYS481 (not a rapidly mutating Y-STR) | |
| 8 | 0892, 0920 | Hispanic, Hispanic | Full match (7/15 autosomal matches) | |
| 9 | 0497, 0601 | 2× Caucasian | 6 mismatches | |
| 10 | 0011, 0163 | 2× African American | 2 mismatches at DYS627 and DYS387S1ab | |
| 11 | 0242, 0591 | African A., Caucasian | 1 mismatch at DYS449 | |
| 12 | 0757, 0970 | 2× Hispanic | TBD | |
| 13 | 1077, 1082, 1091 | 3× Korean | Full match | yes |
| 14 | 0781, 0869 | 2× Hispanic | Full match | yes |
| 15 | 1066, 1231 | 2× Korean | Full match (12/15 autosomal matches) | |

Example 15. Father-Son Study. Ninety five father-son pairs were studied, using both the multiplex of Panel 7 and the multiplex of Y®filer. Of the ninety five pairs, nine pairs (9.5%) could be separated with the multiplex of Panel 7 compared to 6 pairs (6.3%) that could be distinguished using the multiplex of Y®filer. TABLE 6 shows the particular marker which had a detectable mutation.

TABLE 6

| Father-Son Pair | Marker with Mutation | Multiplex panel |
|---|---|---|
| 52144_AF/C1 | DYS458 | Panel 7, Y ®filer |
| 52203_AF/C1 | DYS458 | Panel 7, Y ®filer |
| | DYS518 | Panel 7 |
| 52227_AF/C1 | DYS576 | Panel 7 |
| 52294_AF/C1 | DYS448 | Panel 7, Y ®filer |
| 52318_AF/C1 | DYS448 | Panel 7, Y ®filer |

TABLE 6-continued

| Father-Son Pair | Marker with Mutation | Multiplex panel |
|---|---|---|
| 52361_AF/C1 | DYS19 | Panel 7, Y ®filer |
| 52369_AF/C1 | DYS627 | Panel 7 |
| 52142_AF/C1 | SYD389II | Panel 7, Y ®filer |
| 53160_AF/C1 | DYF387S1ab | Panel 7 |

What is claimed is:

1. A kit for co-amplification of a set of loci in a DNA sample, the kit comprising a set of amplification primers provided together in the kit, the set of amplification primers comprising primers configured for the amplification of:
   Y-STR markers DYS576, DYS389I, DYS460, DYS458, DYS19, DYS456, DYS390, DYS570, DYS437, DYS393, and DYS439,
   wherein the kit omits one or more of Y-STR markers DYS385ab, DYS389II, DYS391, DYS392, DYS438, DYS448, or Y-GATA-H4, and
   wherein the kit comprises an allelic ladder that contains allelic size standards for known alleles of the Y-STR markers DYS576, DYS389I, DYS460, DYS458, DYS19, DYS456, DYS390, DYS570, DYS437, DYS393, and DYS439,
   wherein, for each Y-STR marker, the allelic size standards cover a range from a smallest allele to a largest allele amplified by the set of amplification primers configured to amplify the Y-STR marker,
   wherein each range of allelic size standards is separated by an at least two base pair difference from a preceding range of allelic size standards for a first adjacent Y-STR marker and a proceeding range of allelic size standards for a second adjacent Y-STR marker.

2. The kit of claim 1, further comprising primers for amplifying at least 5-YSTR markers which are rapidly mutating, wherein the at least 5 rapidly mutating Y-STR markers comprise DYF387S1ab, DYS449, DYS570, DYS576, and DYS627, and optionally further comprise DYS518.

3. The kit of claim 1, further comprising dyes for labelling amplicons of the Y-STR markers with one of at least 5 dyes, wherein the at least 5 dyes are configured to be spectrally distinct.

4. The kit of claim 1, wherein the primers are configured to provide sets of amplicons having a base pair size less than about 410 base pairs.

5. The kit of claim 1, wherein the set of primers further comprise primers for the amplification of at least DYF387S1ab, DYS19, DYS389I, DYS390, DYS393, DYS460, DYS437, DYS439, DYS449, DYS456, DYS458, DYS481, DYS518, DYS533, DYS570, DYS576, and DYS627.

6. The kit of claim 1, wherein the set of primers further comprise primers for the amplification of at least DYF387S1ab, DYS19, DYS389I, DYS390, DYS393, DYS460, DYS437, DYS439, DYS449, DYS456, DYS458, DYS481, DYS533, DYS570, DYS576, DYS627, and DYS643.

7. A kit for co-amplification of a set of loci in a DNA sample, the kit comprising a set of amplification primers provided together in the kit, the set of amplification primers comprising primers for the amplification of:
   (i) Y-STR markers DYS576, DYS389I, DYS460, DYS458, DYS19, DYS456, DYS390, DYS570, DYS437, DYS393, and DYS439; and
   (ii) at least 5-YSTR markers which are rapidly mutating, wherein the at least 5 rapidly mutating Y-STR markers comprise DYF387S1ab, DYS449, DYS570, DYS576, and DYS627, and optionally further comprise DYS518,
   wherein the kit omits one or more of Y-STR markers DYS385ab, DYS389II, DYS391, DYS392, DYS438, DYS448, or Y-GATA-H4, and
   wherein the kit comprises an allelic ladder that contains allelic size standards for known alleles of the Y-STR markers DYS576, DYS389I, DYS460, DYS458, DYS19, DYS456, DYS390, DYS570, DYS437, DYS393, and DYS439,
   wherein, for each Y-STR marker, the allelic size standards cover a range from a smallest allele to a largest allele amplified by the set of amplification primers configured to amplify the Y-STR marker,
   wherein each range of allelic size standards is separated by an at least two base pair difference from a preceding range of allelic size standards for a first adjacent Y-STR marker and a proceeding range of allelic size standards for a second adjacent Y-STR marker.

8. The kit of claim 1, wherein the amplification primers in the set are labelled with one of at least 5 dyes, wherein the at least 5 dyes are configured to be spectrally distinct.

9. The kit of claim 1, wherein at least one of the amplification primers in the set comprises a mobility modifier moiety, and wherein the structure of the mobility modifier moiety of the amplification primer for each different Y-STR marker may be selected independently.

10. The kit of claim 7, wherein at least one of the amplification primers in the set comprises a mobility modifier moiety, and wherein the structure of the mobility modifier moiety of the amplification primer for each different Y-STR marker may be selected independently.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
atcatcatca tcaacatcat c                                            21

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
gatagataga tacatagata                                              20

<210> SEQ ID NO 3
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
attgcattgc attgc                                                   15

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
atcgatcgaa cgatcgatcg                                              20

<210> SEQ ID NO 5
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 5
atccatcgat ccatcgatcg atccatcc                                              28

<210> SEQ ID NO 6
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aatgaatgaa tgaatgaatg aatgaatgaa tgaatg                                     36

<210> SEQ ID NO 7
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
aatgaatgaa tgaatgaatg aatgatgaat gaatgaatg                                  39

<210> SEQ ID NO 8
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aaagaaagaa aggtaggaag gaaggaagga agaaagaaag gaagaaagaa aggaagaaag           60

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tagatagata gataggtaga                                                       20

<210> SEQ ID NO 10
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
tctgtctgtc tgtcta                                                           16

<210> SEQ ID NO 11
<211> LENGTH: 24

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
tctgtctatc tgtctgtctg tcta                                      24

<210> SEQ ID NO 12
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
tctgtctgtc tgtctgtctg tctgtctgtc tgtctatctg tctatctatc tatcta    56

<210> SEQ ID NO 13
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
tctatctgtc tgtctatcta tctatcta                                  28

<210> SEQ ID NO 14
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(48)
<223> OTHER INFORMATION: a, c, t, g, unknown or other

<400> SEQUENCE: 14
agagatnnnn nnnnnnnnnn nnnnnnnnnn nnnnnnnnnn nnnnnnnnag agat      54

<210> SEQ ID NO 15
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(26)
<223> OTHER INFORMATION: a, c, t, g, unknown or other
<220> FEATURE:
<221> NAME/KEY: modified_base
<222> LOCATION: (39)..(50)
<223> OTHER INFORMATION: a, c, t, g, unknown or other

<400> SEQUENCE: 15
ttctnnnnnn nnnnnnnnnn nnnnnnttct ttctttctnn nnnnnnnnnn ttct      54
```

```
<210> SEQ ID NO 16
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (41)..(46)
<223> OTHER INFORMATION: a, c, t, g, unknown or other
<220> FEATURE:
<221> NAME/KEY: modified_base
<222> LOCATION: (51)..(77)
<223> OTHER INFORMATION: a, c, t, g, unknown or other

<400> SEQUENCE: 16
aaagaaagaa aggaagaaag ggagaaagaa agaaagaaag nnnnnnaaag nnnnnnnnnn      60
nnnnnnnnnn nnnnnnnaag gaaggaagga agg                                  93

<210> SEQ ID NO 17
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (13)..(28)
<223> OTHER INFORMATION: a, c, t, g, unknown or other
<220> FEATURE:
<221> NAME/KEY: modified_base
<222> LOCATION: (45)..(126)
<223> OTHER INFORMATION: a, c, t, g, unknown or other

<400> SEQUENCE: 17
agaaagaaag aannnnnnnn nnnnnnnnag agagagagag aaagnnnnnn nnnnnnnnnn      60
nnnnnnnnnn nnnnnnnnnn nnnnnnnnnn nnnnnnnnnn nnnnnnnnnn nnnnnnnnnn     120
nnnnnnaagg aaggaagg                                                   138

<210> SEQ ID NO 18
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: Variation
<222> LOCATION: (49)..(56)
<223> OTHER INFORMATION: /replace=" "
<220> FEATURE:
<221> NAME/KEY: misc_feature
<222> LOCATION: (49)..(56)
<223> OTHER INFORMATION: /note="This region may or may not be present in
      its entirety"
<220> FEATURE:
<221> NAME/KEY: misc_feature
<222> LOCATION: (1)..(60)
<223> OTHER INFORMATION: /note="Variant nucleotides given in the
      sequence have no preference with respect to those in the
      annotations for variant positions"

<400> SEQUENCE: 18
tctatctatc tatctatgta tgtatctatc tatgtatgta tctatctatg tatgtatcta      60
```

```
<210> SEQ ID NO 19
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(16)
<223> OTHER INFORMATION: a, c, t, g, unknown or other

<400> SEQUENCE: 19
tagannnnnn nnnnnngatc gatcaataga tagatagata ga                    42

<210> SEQ ID NO 20
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (33)..(48)
<223> OTHER INFORMATION: a, c, t, g, unknown or other

<400> SEQUENCE: 20
aaagaaagaa aggtaggaag gaaggaagga agnnnnnnnn nnnnnnnnga aggaaggaag   60
gaaggaagga aggaaggaag gaagaaag                                     88

<210> SEQ ID NO 21
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (13)..(28)
<223> OTHER INFORMATION: a, c, t, g, unknown or other
<220> FEATURE:
<221> NAME/KEY: modified_base
<222> LOCATION: (45)..(125)
<223> OTHER INFORMATION: a, c, t, g, unknown or other

<400> SEQUENCE: 21
agaaagaaag aannnnnnnn nnnnnnnnag agagagagag aaagnnnnnn nnnnnnnnnn   60
nnnnnnnnnn nnnnnnnnnn nnnnnnnnnn nnnnnnnnnn nnnnnnnnnn nnnnnnnnnn  120
nnnnnaagga aggaagg                                                 137

<210> SEQ ID NO 22
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (49)..(60)
<223> OTHER INFORMATION: a, c, t, g, unknown or other

<400> SEQUENCE: 22
```

```
tagatagata gatagataga tagatagata gatagataga tagatagann nnnnnnnnnn        60
gatggatgaa tagatagata gataga                                             86
```